(12) United States Patent
Sigler et al.

(10) Patent No.: US 7,649,085 B2
(45) Date of Patent: *Jan. 19, 2010

(54) SAQUINAVIR CONJUGATES AND ANTIBODIES USEFUL IN IMMUNOASSAY

(75) Inventors: Gerald F. Sigler, Carmel, IN (US);
Raymond A. Hui, Indianapolis, IN (US);
Ina Deras, San Diego, CA (US);
Richard Terry Root, Fishers, IN (US);
Erasmus Huber, Finning (DE); Herbert W. Von Der Eltz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 34 days.

This patent is subject to a terminal disclaimer.

(21) Appl. No.: 11/420,502

(22) Filed: May 26, 2006

(65) Prior Publication Data

US 2006/0211107 A1  Sep. 21, 2006

Related U.S. Application Data

(60) Division of application No. 10/669,831, filed on Sep. 24, 2003, now Pat. No. 7,193,065, which is a continuation-in-part of application No. 10/192,052, filed on Jul. 10, 2002, now abandoned.

(60) Provisional application No. 60/305,192, filed on Jul. 13, 2001.

(51) Int. Cl.
| | |
|---|---|
| *C07K 17/06* | (2006.01) |
| *C07K 1/10* | (2006.01) |
| *C07K 16/00* | (2006.01) |
| *G01N 33/532* | (2006.01) |
| *C07D 277/04* | (2006.01) |

(52) U.S. Cl. .................. 530/403; 530/402; 530/388.9; 436/544; 548/146

(58) Field of Classification Search ............. 530/389.8, 530/405, 388.9; 435/7.5, 326, 345; 436/546, 436/815; 544/316
See application file for complete search history.

(56) References Cited

U.S. PATENT DOCUMENTS 6,635,745 B2 * 10/2003 Sedrani et al. .............. 530/405

(Continued)

FOREIGN PATENT DOCUMENTS

EP  1207394 A2  8/2002

(Continued)

OTHER PUBLICATIONS

Mattson et al. A practical approach to crosslinking. Molecular Biology Reports 1993, vol. 17, pp. 167-183.*
Akeb, F., "Quantification of plasma and intracellular levels of the HIV protease inhibitor ritonavir by competitive ELISA," Journal of Immunological Methods 263 (2002) 1-9.

(Continued)

*Primary Examiner*—Shafiqul Haq
(74) *Attorney, Agent, or Firm*—Marilyn Amick; Roche Diagnostics Operations, Inc.

(57) ABSTRACT

Activated haptens useful for generating immunogens to HIV protease inhibitors, immunogens useful for producing antibodies to HIV protease inhibitors, and antibodies and labeled conjugates useful in immunoassays for the HIV protease inhibitor saquinavir. The novel haptens feature an activated functionality at the central, non-terminal hydroxyl group. Also described are monoclonal antibodies specific for saquinavir having less than 10% cross-reactivity with lopinavir, nelfinavir, amprenavir, ritonavir, and indinavir, and a murine hybridoma producing said antibodies.

9 Claims, 24 Drawing Sheets

U.S. PATENT DOCUMENTS 6,992,177 B1 * 1/2006 Hui et al. .................. 530/388.9
2003/0010088 A1 1/2003 Tomisawa

FOREIGN PATENT DOCUMENTS

FR 2773994 7/1999
WO WO 03/075010 A2 9/2003

OTHER PUBLICATIONS

Valdez, H. et al., "Response to immunization with recall and neoanitgens after prolonged administration of an HIV-1 protease inhibitor-containing regimen," AIDS 2000, vol. 14, No. 1, 11-21.

Wiltshire, H. et al., "Chromatographic and Immunochemical Approaches to the Analysis of the HIV Protease Inhibitor Saquinavir in Plasma," Analytical Biochemistry 281, 105-114 (2000).

* cited by examiner

SAQUINAVIR CONJUGATES AND ANTIBODIES USEFUL IN IMMUNOASSAY

RELATED APPLICATIONS

This application divisional of U.S. Ser. No. 10/669,831, filed Sep. 24, 2003, now U.S. Pat. No. 7,193,065 which is a continuation-in-part of U.S. patent application No. 10/192,052 filed Jul. 10, 2002, now abandoned which claims priority to U.S. Provisional Application No. 60/305,192 filed Jul. 13, 2001.

FIELD OF THE INVENTION

This invention relates to novel protease inhibitor conjugates and antibodies useful in immunoassay. More specifically, this invention relates to novel activated haptens useful for generating immunogens to HIV protease inhibitors, to novel immunogens useful for producing antibodies to HIV protease inhibitors, and to novel antibodies and labeled conjugates useful in immunoassays for HIV protease inhibitors.

BACKGROUND OF THE INVENTION

HIV protease inhibitors are an important new class of drugs which have made a significant impact on the health care of AIDS patients since the first one, saquinavir, was introduced to the marketplace in 1995. Examples of other protease inhibitors include amprenavir, indinavir, nelfinavir, lopinavir, ritonavir, and atazanavir. They are especially effective in combination with other anti-HIV drugs such a reverse transcriptase inhibitors or with other HIV protease inhibitors. In spite of remarkable success with these new therapeutic regimens, there are strong indications that results would be much improved if therapeutic drug testing methods were available for monitoring the concentrations of protease inhibitors. Not all patients respond optimally to protease inhibitor combination therapies. Even those who do respond can subsequently develop drug resistance due to the notoriously high rate of mutation of the HIV virus. However, it has been shown that there is a clear relationship between plasma levels of the protease inhibitors and therapeutic efficacy based upon decreased viral load and increased CD4 cell count. One problem lies in the fact that the drugs are metabolized extensively and are subject to complex drug-drug interactions. The results are extremely complex pharmacokinetics and a strong element of unpredictability between dosage and resultant drug levels at any particular time for any particular patient. With therapeutic drug monitoring, drug dosages could be individualized to the patient, and the changes of keeping the virus in check would be much higher. But routine therapeutic drug monitoring of protease inhibitors would require the availability of simple automated tests adaptable to high throughput clinical analyzers. Currently most reports on therapeutic drug monitoring of protease inhibitors have used HPLC methods which are slow, labor-intensive, and expensive. Recently there was a report of a radioimmunoassay (RIA) method for saquinavir (Wiltshire et al., Analytical Biochemistry 281, 105-114, 2000). However, such a method would not be adaptable to high-throughput therapeutic drug monitoring and, like all RIA methods, suffers from the disadvantages of having regulatory, safety and waste disposal issues related to the radioactive isotope label used in the assay. The most desirable assay formats for therapeutic drug monitoring are non-isotopic immunoassays, and such methods have heretofore been unknown for monitoring HIV protease inhibitors.

As indicated above, HPLC has been the method of choice for monitoring HIV protease inhibitors. Two recent reports in the literature described HPLC assays for the simultaneous determination of several protease inhibitors in human plasma, Poirier et al., Therapeutic Drug Monitoring 22, 465-473, 2000 and Remmel et al., Clinical Chemistry, 46, 73-81, 2000.

Chemical and biological assays generally involve contacting the analyte of interest with a pre-determined amount of one or more assay reagents, measuring one or more properties of a resulting product (the detection product), and correlating the measured value with the amount of analyte present in the original sample, typically by using a relationship determined from standard or calibration samples containing known amounts of analyte of interest in the range expected for the sample to be tested. Typically, the detection product incorporates one or more detectable labels which are provided by one or more assay reagents. Examples of commonly used labels include functionalized microparticles, radioactive isotope labels such as $^{125}I$ and $^{32}P$, enzymes such as peroxidase and beta-galactosidase and enzyme substrate labels, fluorescent labels such as fluoresceins and rhodamines, electron-spin resonance labels such as nitroxide free radicals, immunoreactive labels such as antibodies and antigens, labels which are one member of a binding pair such as biotin-avidin and biotin-streptavidin, and electrochemiluminescent labels such as those containing a ruthenium bipyridyl moiety. Sandwich assays typically involve forming a complex in which the analyte of interest is sandwiched between one assay reagent which is ultimately used for separation, e.g., antibody, antigen, or one member of a binding pair, and a second assay reagent which provides a detectable label. Competition assays typically involve a system in which both the analyte of interest and an analog of the analyte compete for a binding site on another reagent, e.g., an antibody, wherein one of the analyte, analog or binding reagent possesses a detectable label.

Copending U.S. patent application Ser. No. 09/712,525, filed Nov. 14, 2000 having the same assignee as the present application and published as EP 1 207 394 on May 22, 2002, describes a non-isotopic immunoassay for an HIV protease inhibitor comprising incubating a sample containing the inhibitor with a receptor specific for the inhibitor or for a metabolite of said inhibitor and further with a conjugate comprising an analog of the inhibitor and a non-isotopic signal generating moiety. Signal generated as a result of binding of the inhibitor by the receptor is measured and correlated with the presence or amount of protease inhibitor in the original sample. The protease inhibitor conjugates of the present invention are especially useful in such an assay.

SUMMARY OF THE INVENTION

The present invention relates to novel activated haptens useful for generating immunogens to HIV protease inhibitors. These activated haptens have the general structure:

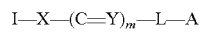

I—X—(C=Y)$_m$—L—A wherein I is an HIV protease inhibitor radical, X is O or NH, Y is O, S or NH, m is 0 or 1, L is a linker consisting of from 0 to 40 carbon atoms arranged in a straight chain or a branched chain, saturated or unsaturated, and containing up to two ring structures and 0-20 heteroatoms, with the proviso that not more than two heteroatoms may be linked in sequence, and A is an activated functionality chosen from the group consisting of active esters, isocyanates, isothiocyanates, thiols, imidoesters, anhydrides, maleimides, thiolactones, diazonium groups and aldehydes.

The present invention also relates to novel immunogens having the following structure:

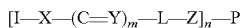

wherein I is an HIV protease inhibitor radical, X is O or NH, Y is O, S, or NH, m is 0 or 1, L is a linker comprising 0 to 40 carbon atoms arranged in a straight chain or a branched chain, saturated or unsaturated, and containing up to two ring structures and 0-20 heteroatoms, with the proviso that not more than two heteroatoms are linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

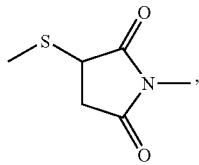

P is a polypeptide, a polysaccharide, or a synthetic polymer, and n is a number from 1 to 50 per 50 kilodaltons molecular weight of P.

The present invention also relates to novel labeled conjugates having the following structure:

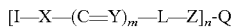

wherein I is an HIV protease inhibitor radical, X is O or NH, Y is O, S, or NH, m is 0 or 1, L is a linker comprising 0 to 40 carbon atoms arranged in a straight chain or a branched chain, saturated or unsaturated, and containing up to two ring structures and 0-20 heteroatoms, with the proviso that not more than two heteroatoms are linked in sequence, Z is a moiety selected from the group consisting of —CONH—, —NHCO—, —NHCONH—, —NHCSNH—, —OCONH—, —NHOCO—, —S—, —NH(C=NH)—, —N=N—, —NH—, and

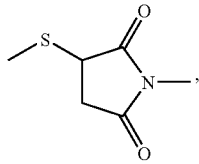

Q is a non-isotopic label, and n is a number from 1 to 50 per 50 kilodaltons molecular weight of Q.

The present invention also comprises specific monoclonal antibodies to saquinavir, nelfinavir, indinavir, amprenavir, lopinavir, and ritonavir having less than 10% cross-reactivity to other protease inhibitors. Finally, the present invention comprises antibodies generated from the immunogens of the invention as well as immunoassay methods and test kits which incorporate the antibodies and labeled conjugates of the present invention.

Figure 1:
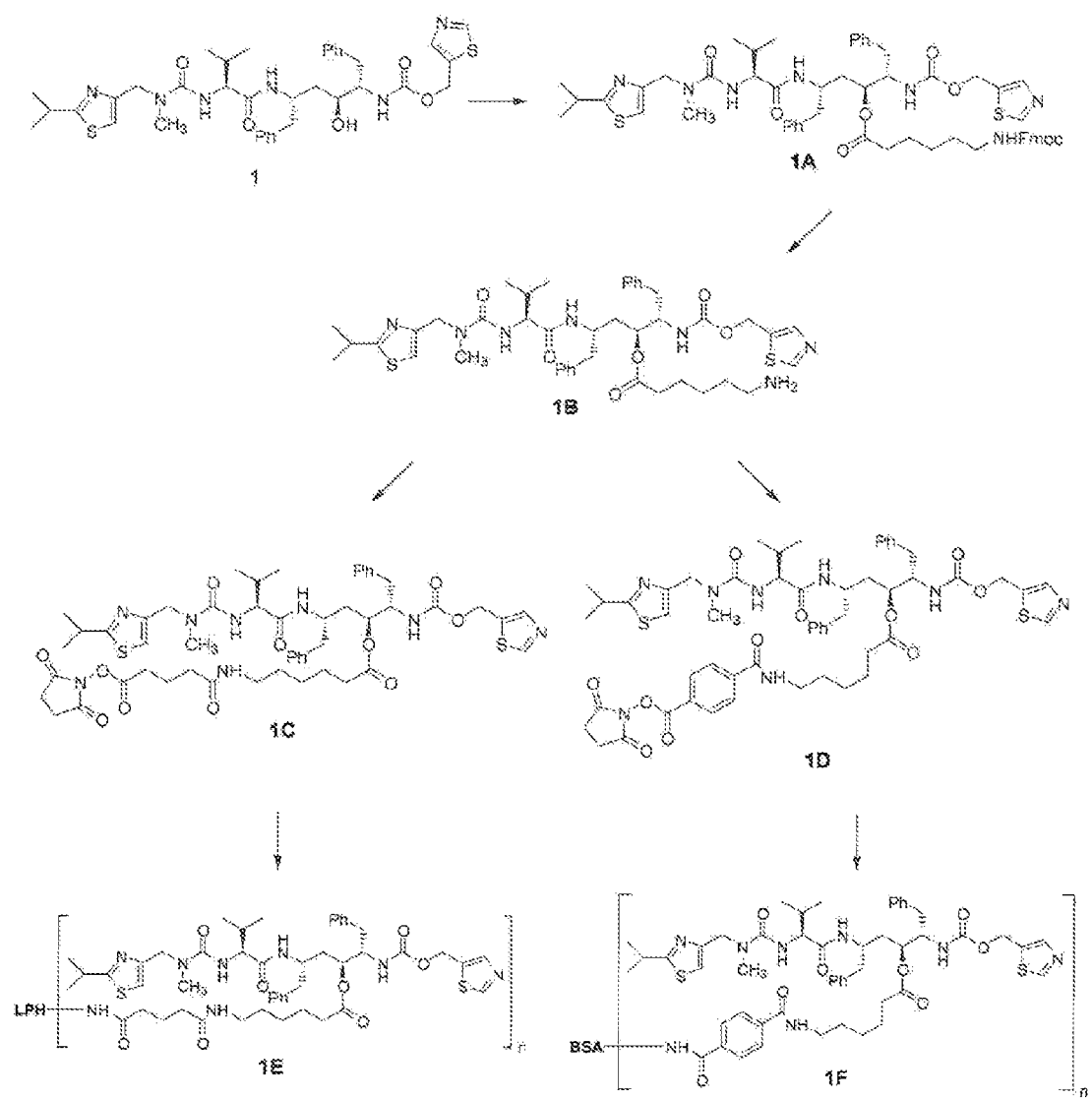
FIG. 1 illustrates a scheme for synthesis of O-acylated ritonavir activated haptens, LPH immunogen and BSA conjugate.
Figure 2:
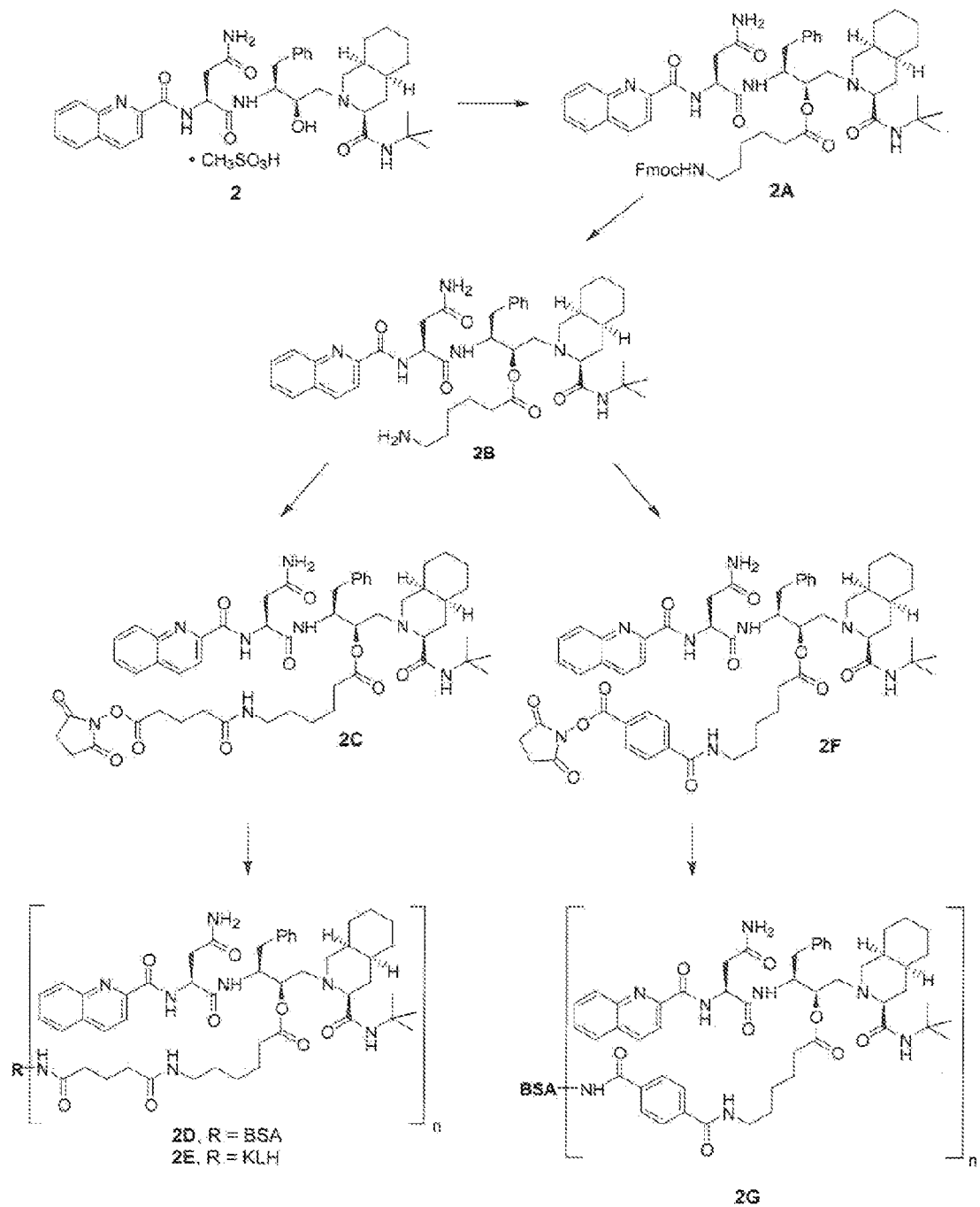
FIG. 2 illustrates a scheme for synthesis of O-acylated saquinavir activated haptens, KLH immunogen and BSA conjugates.
Figure 3:
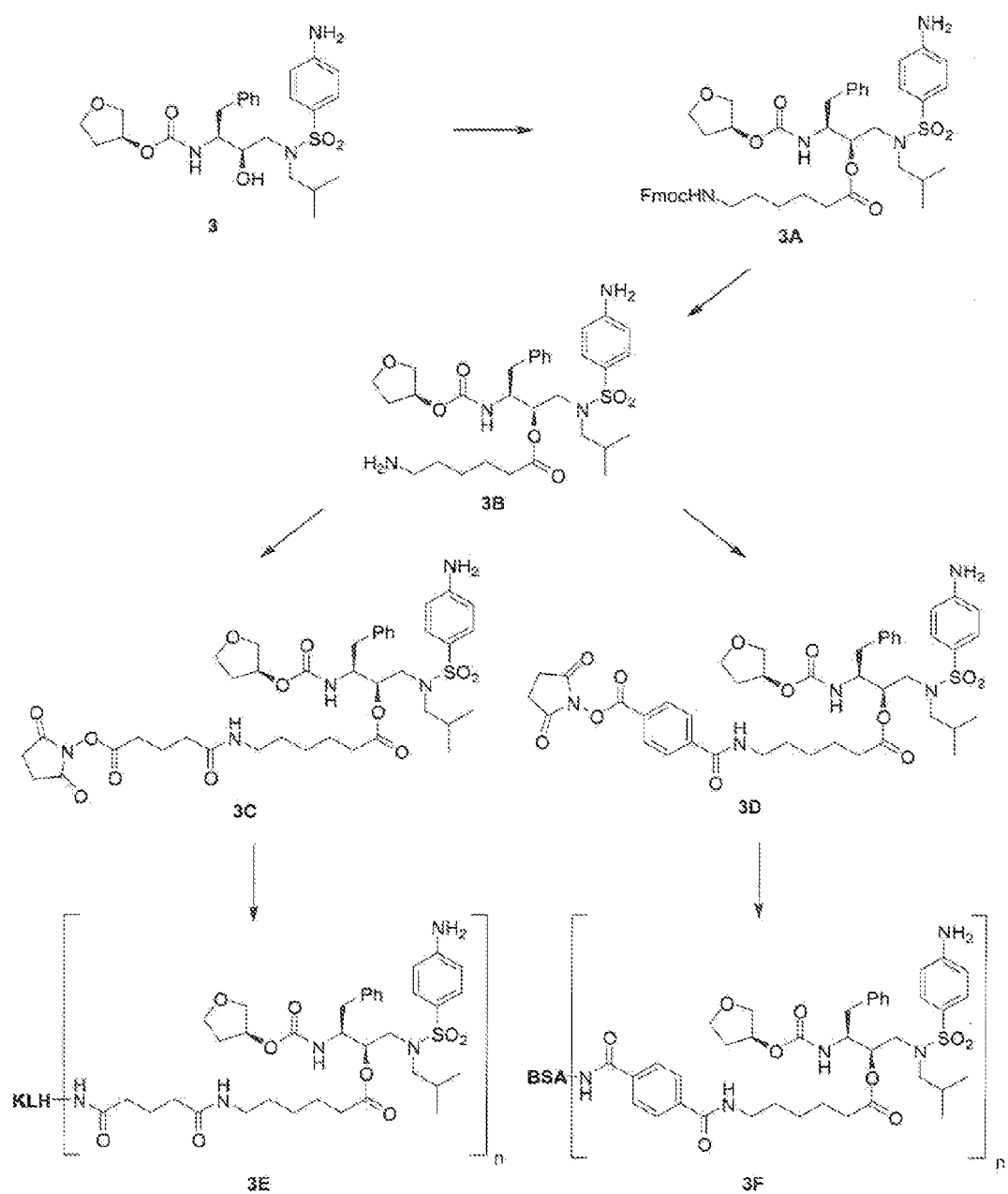
FIG. 3 illustrates a scheme for synthesis of O-acylated amprenavir activated haptens, KLH immunogen and BAS conjugate.
Figure 4:
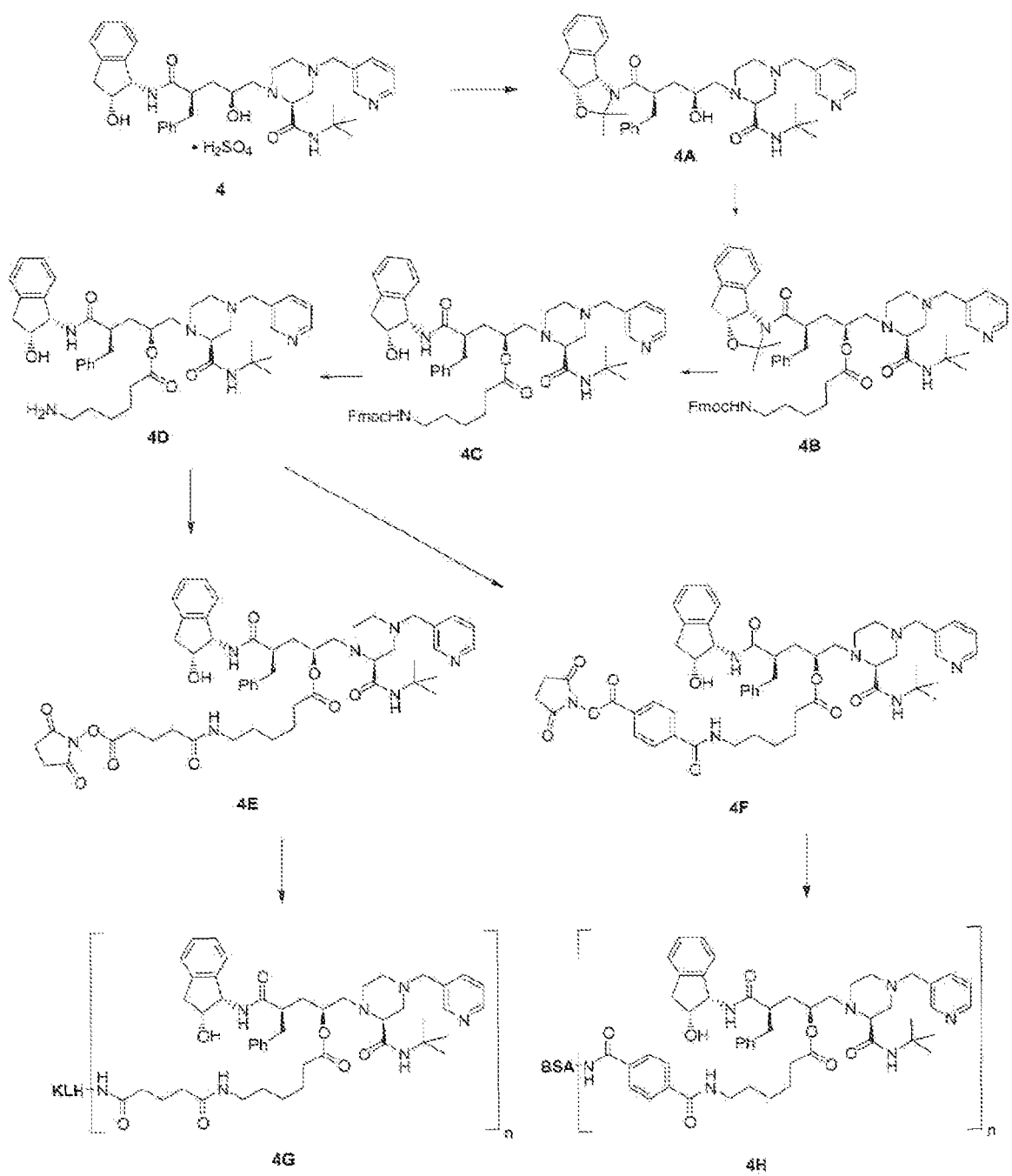
FIG. 4 illustrates a scheme for synthesis of O-acylated indinavir activated haptens, KLH immunogen and BSA conjugate.
Figure 5:
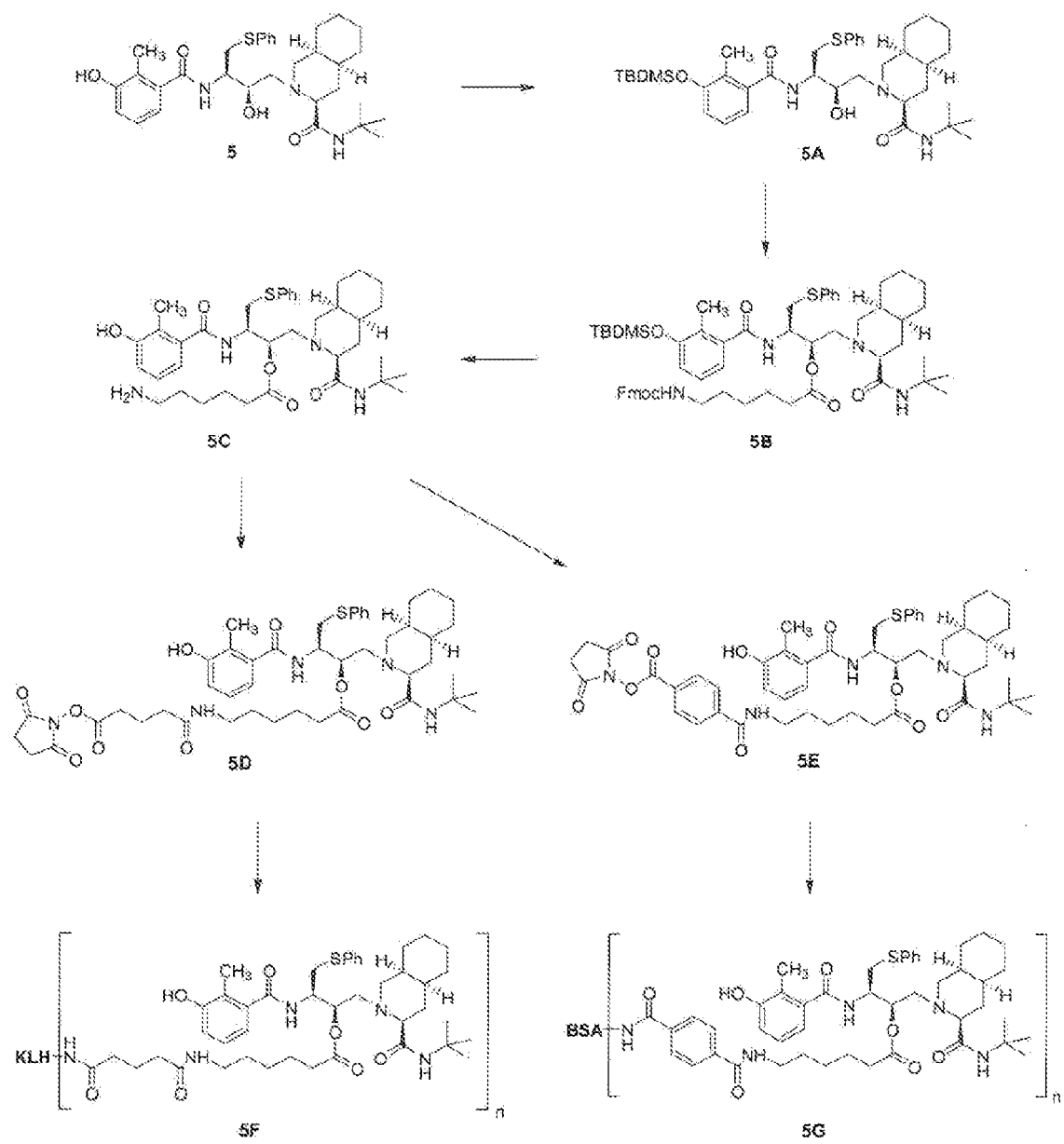
FIG. 5 illustrates a scheme for synthesis of O-acylated nelfinavir activated haptens, KLH immunogen and BSA conjugate.
Figure 6:
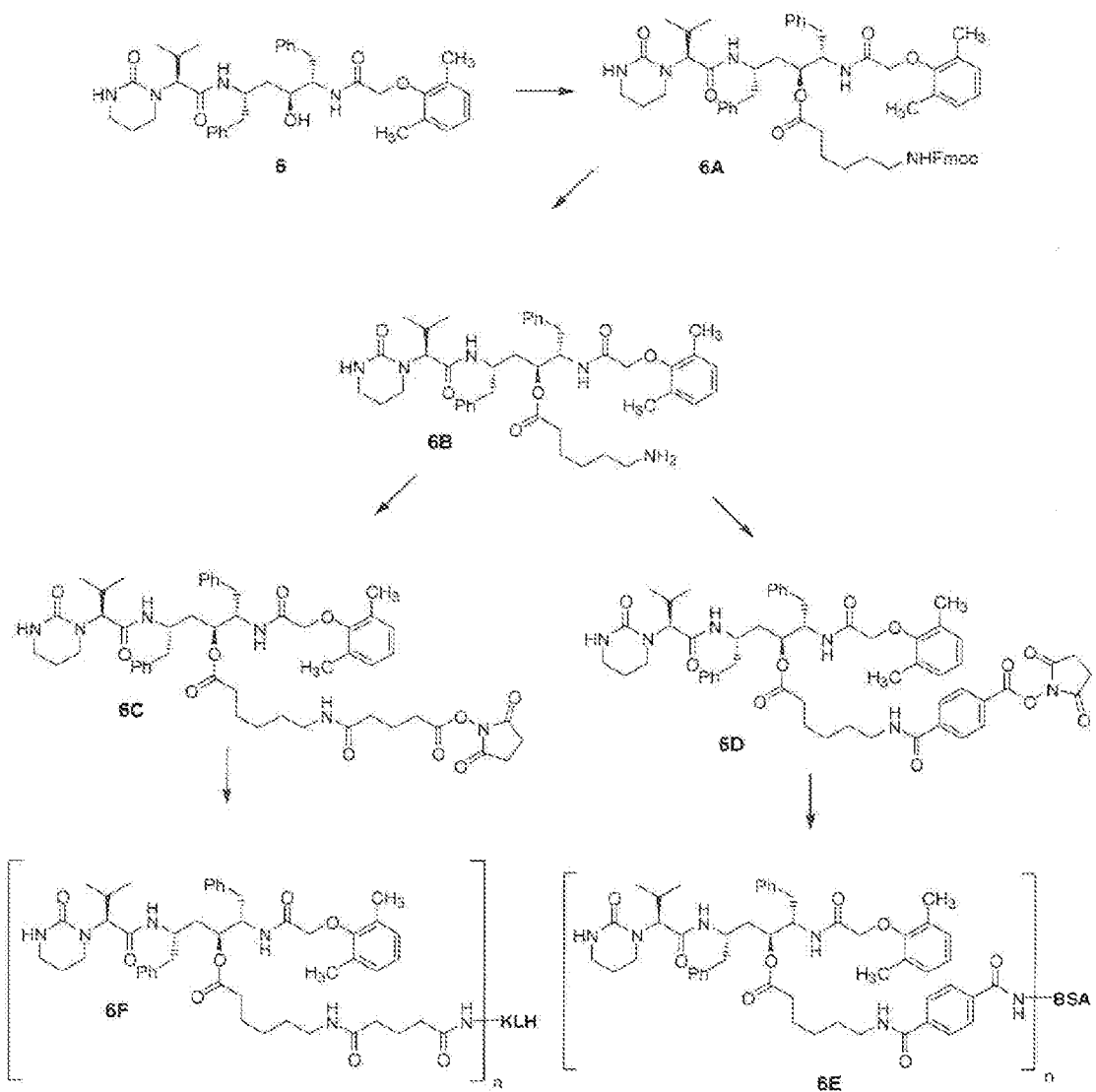
FIG. 6 illustrates a scheme for synthesis of O-acylated lopinavir activated haptens, KLH immunogen and BSA conjugate.
Figure 7:
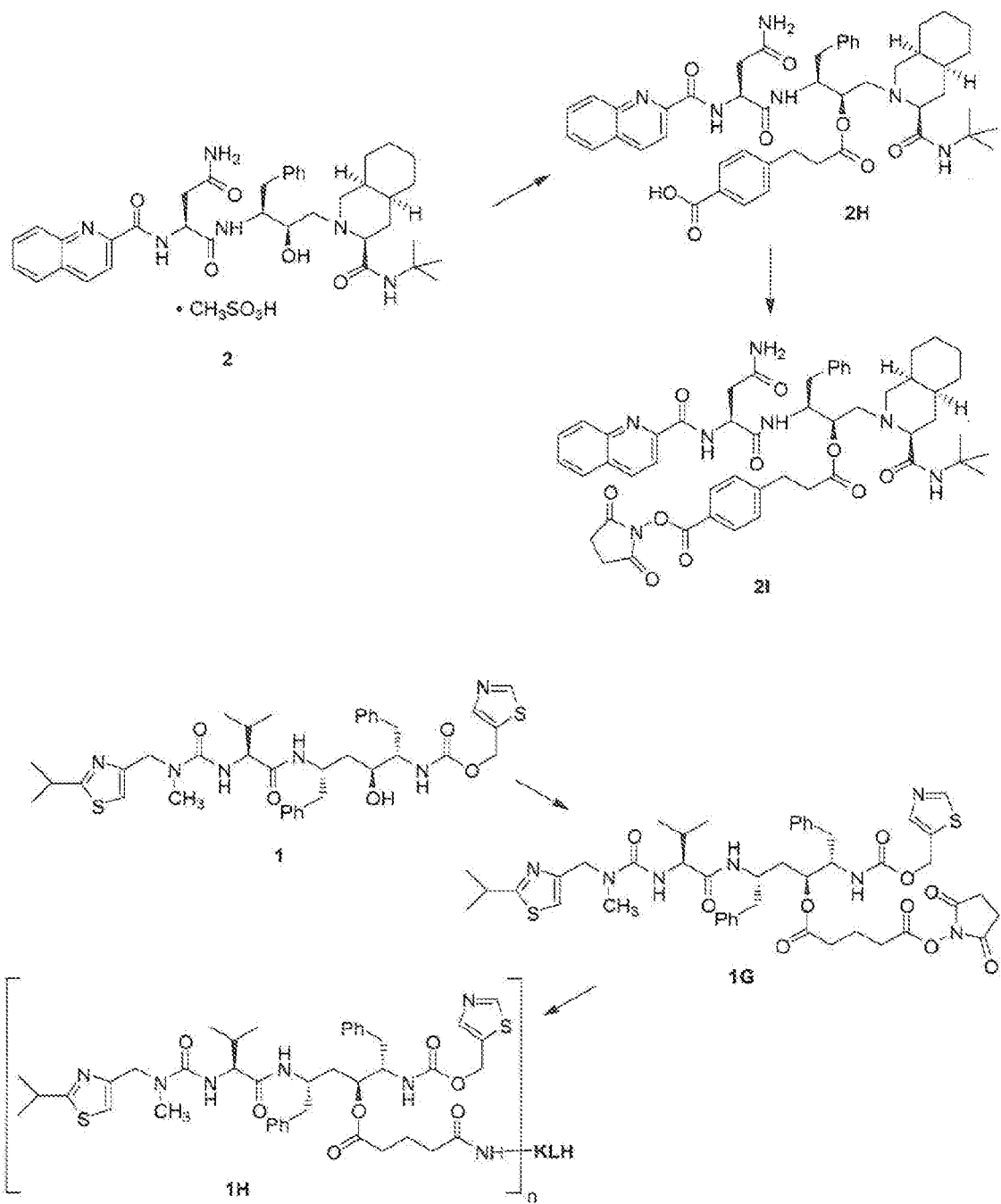
FIG. 7 illustrates a scheme for synthesis of an alternative O-acylated saquinavir and ritonavir activated haptens and an alternative ritonavir immunogen.
Figure 8:
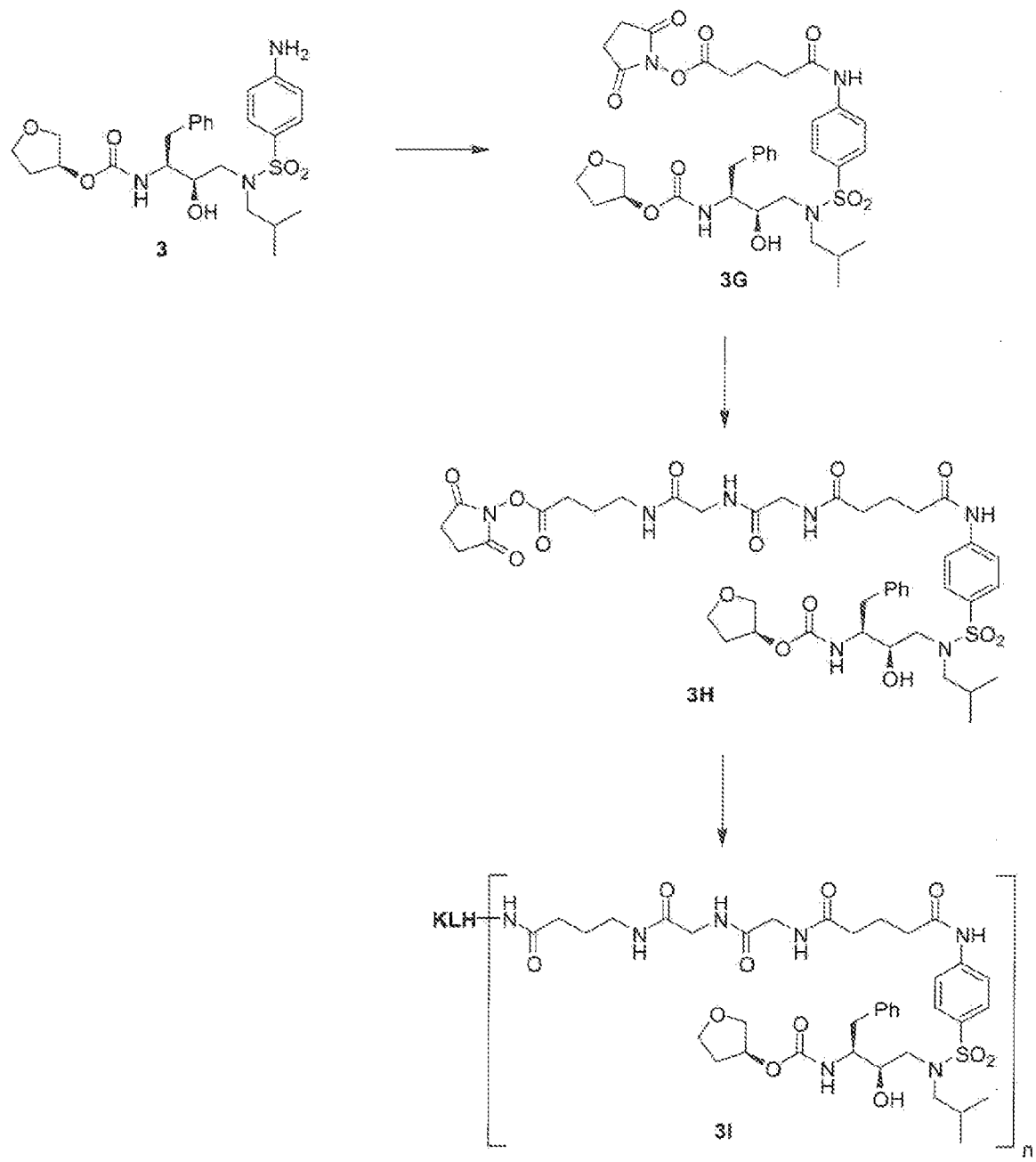
FIG. 8 illustrates a scheme for synthesis of an N-acylated amprenavir immunogen.
Figure 9:
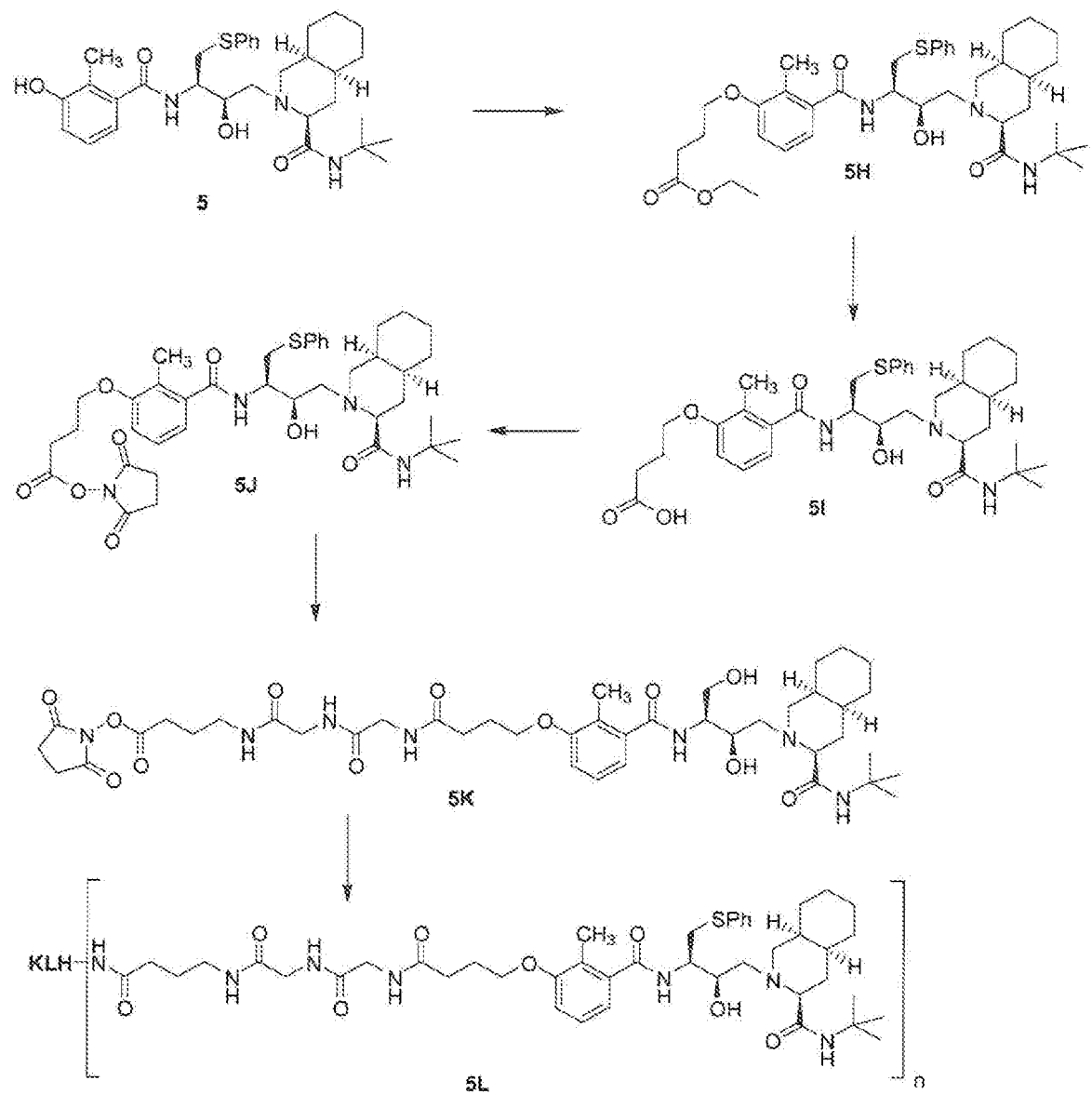
FIG. 9 illustrates a scheme for synthesis of an O-alkylated nelfinavir immunogen.
Figure 10A:
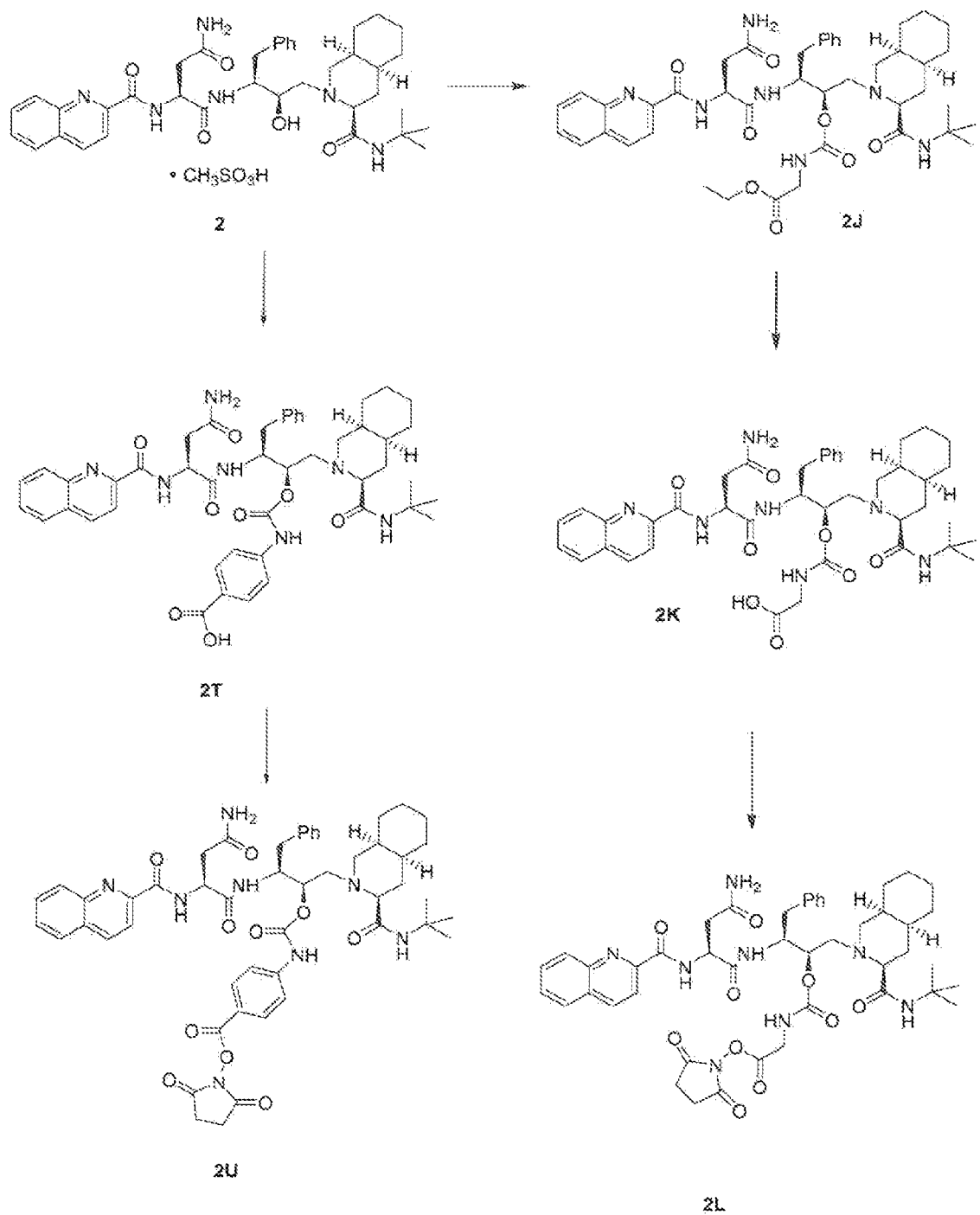
FIGS. 10(a) and 10(b) illustrate a scheme for synthesis of O-carbamylated saquinavir activated haptens.
Figure 10B:
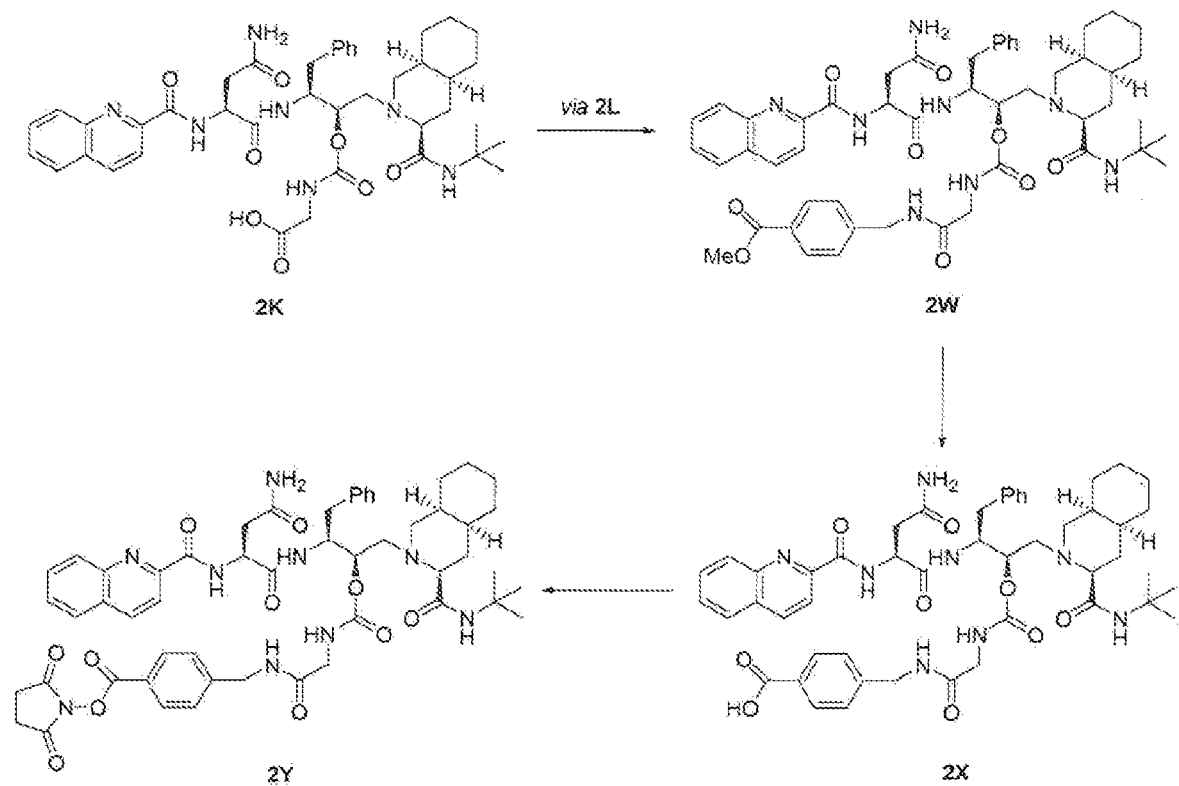
Figure 11:
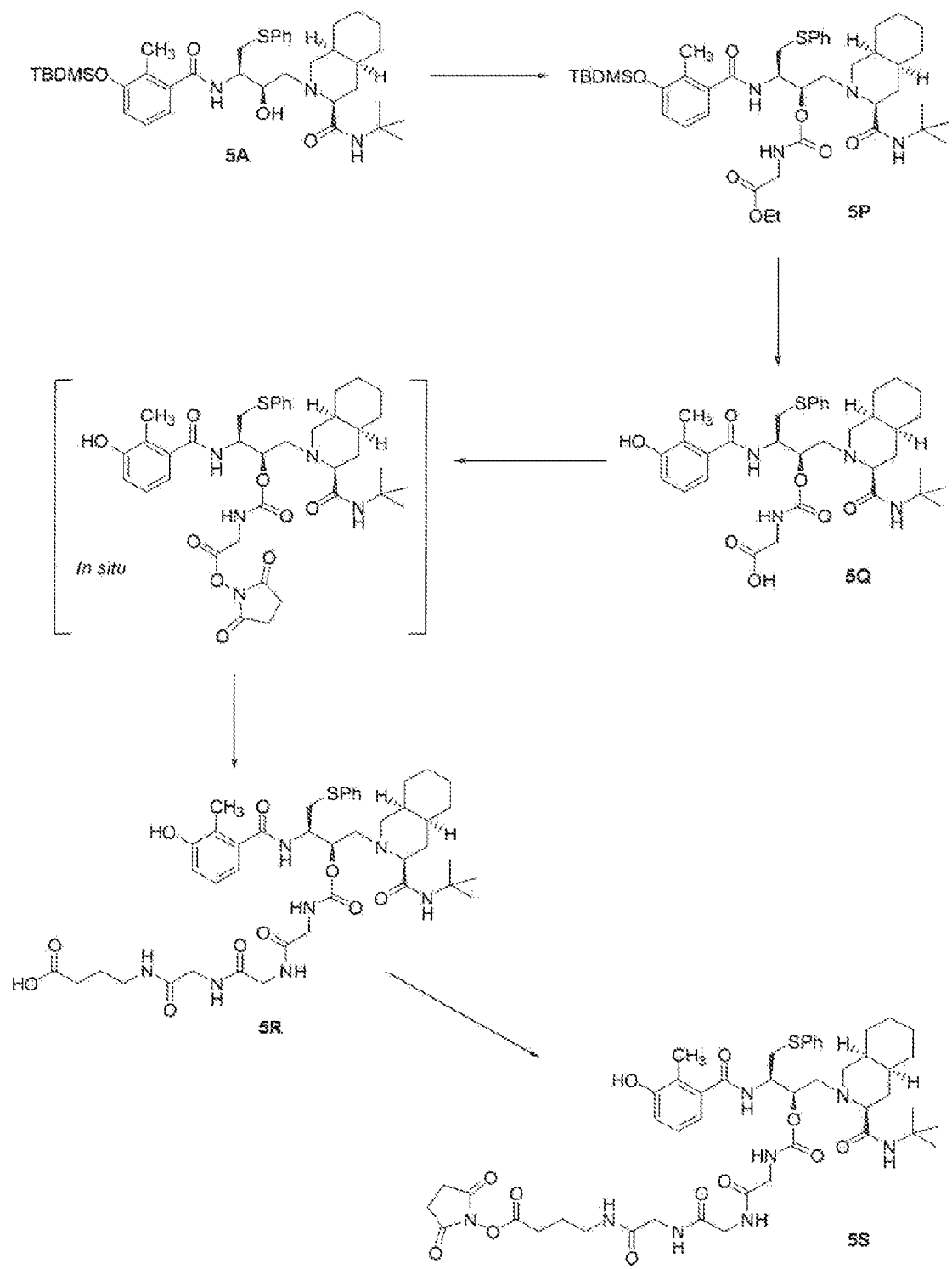
FIG. 11 illustrates a scheme for synthesis of O-carbamylated nelfinavir activated haptens.
Figure 12:
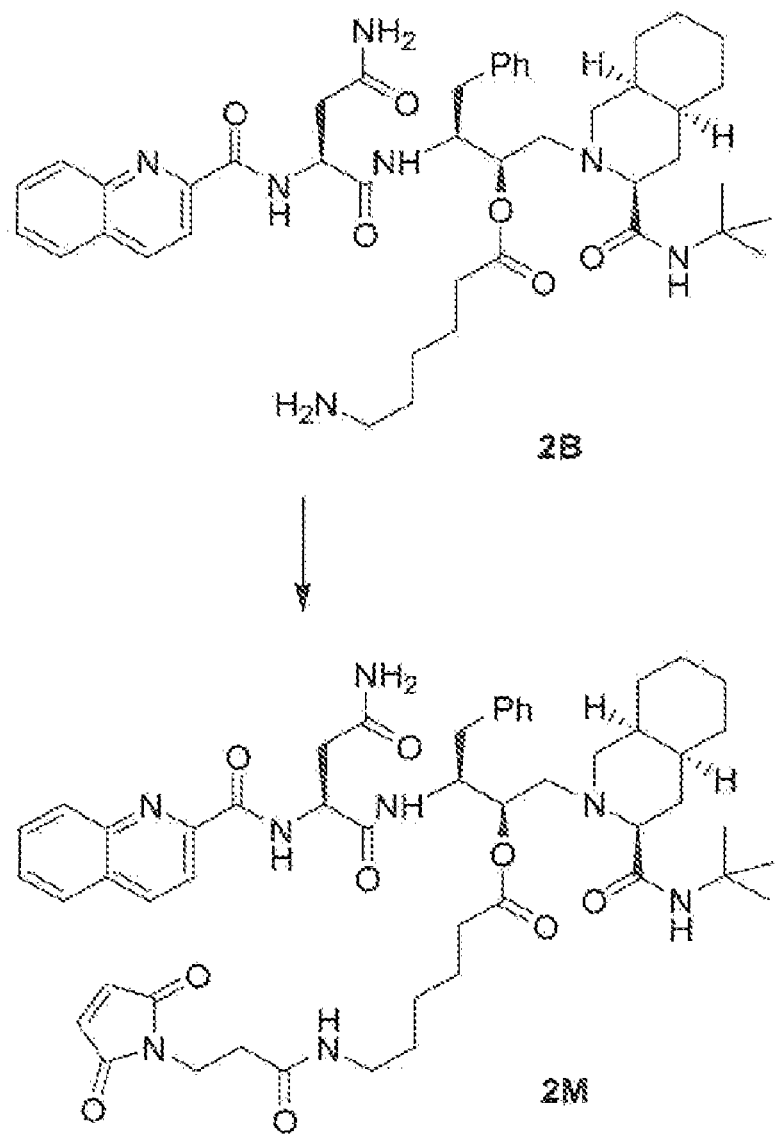
FIG. 12 illustrates a scheme for synthesis of O-acylated saquinavir maleimide activated hapten.
Figure 13:
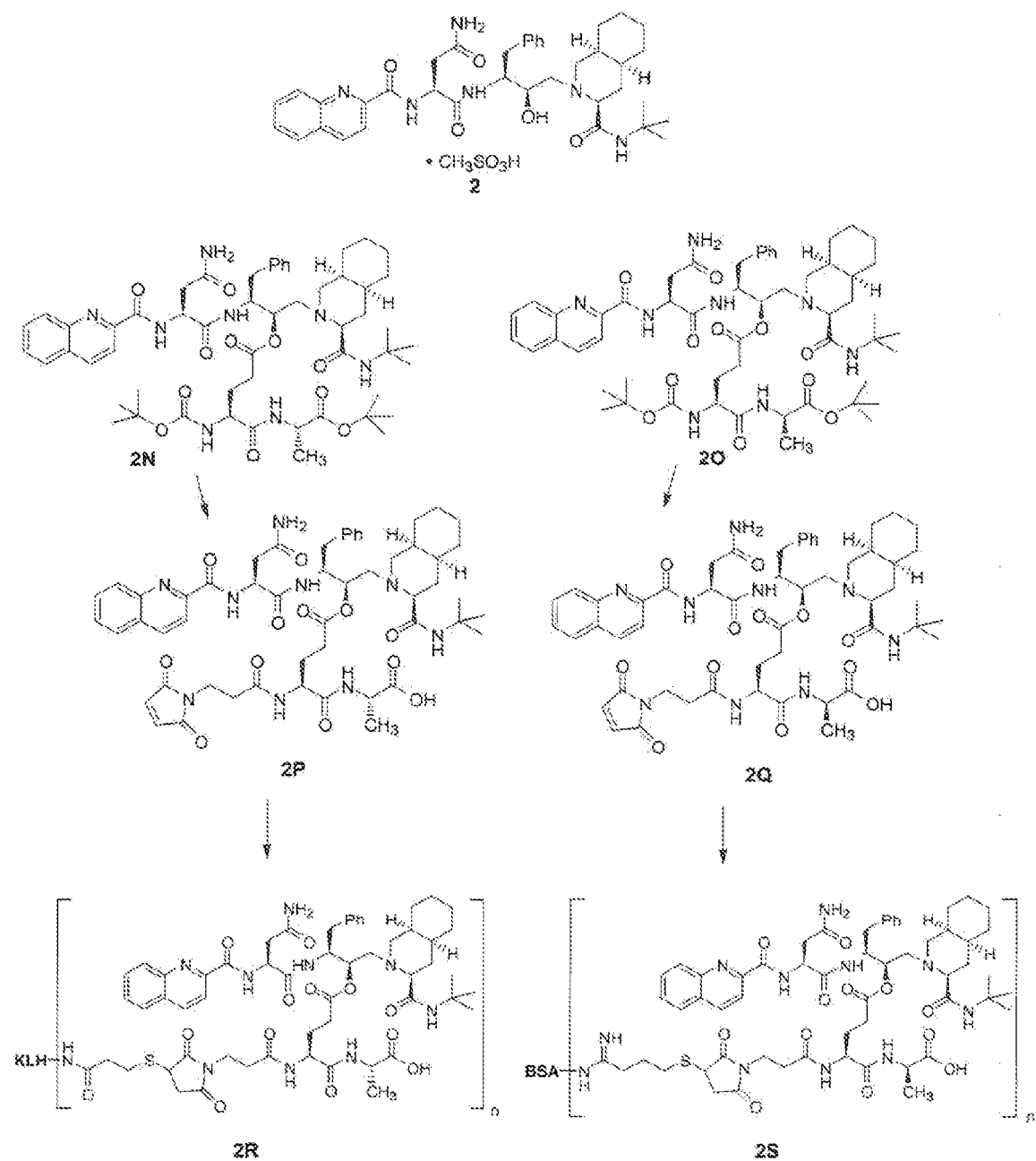
FIG. 13 illustrates a scheme for synthesis of O-acylated saquinavir activated haptens with peptide linkers and maleimide end groups. Also illustrated is a KLH immunogen and BSA conjugate derived from the latter activated haptens.
Figure 14:
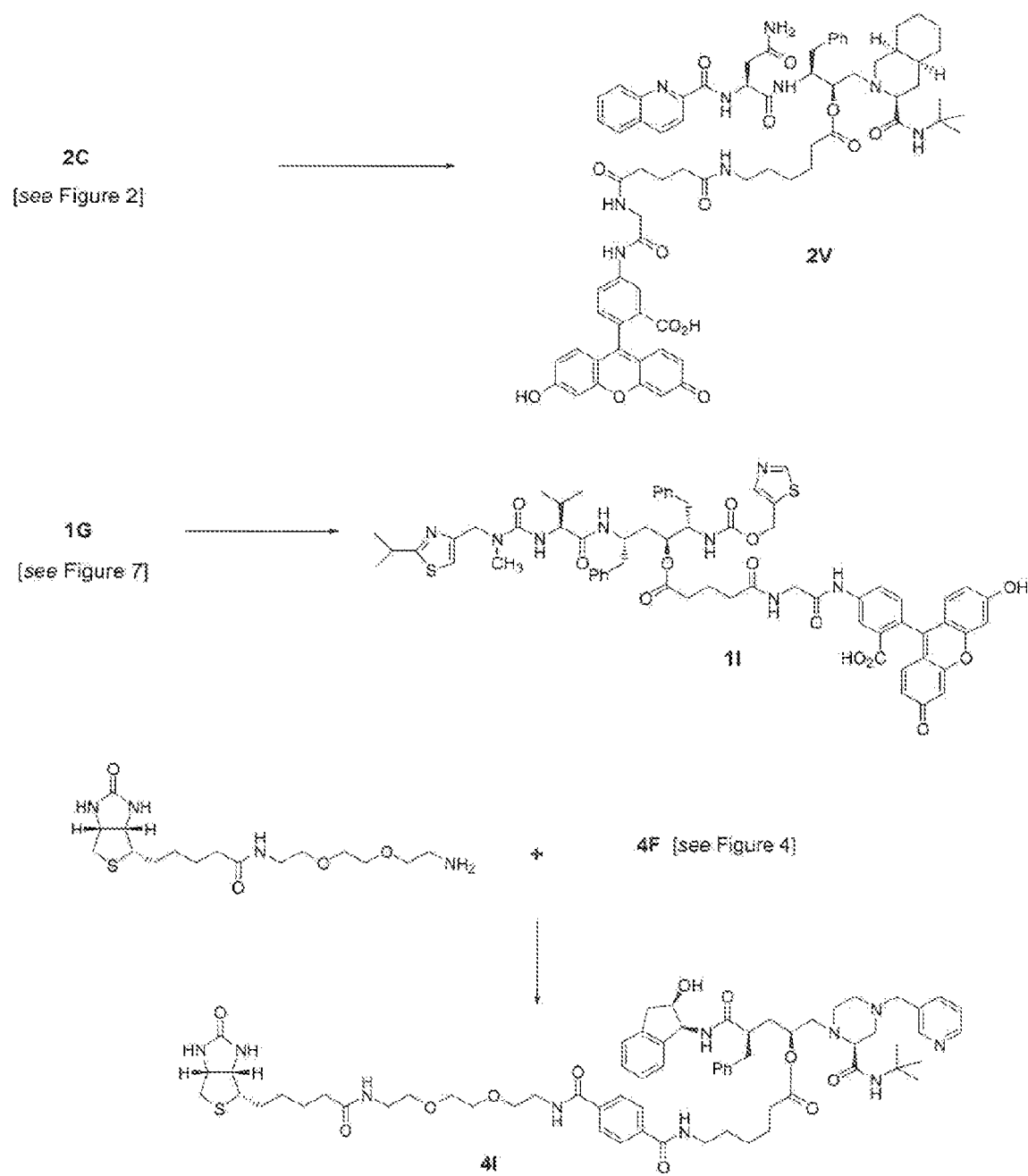
FIG. 14 illustrates a scheme for synthesis of fluorescein conjugates of saquinavir and ritonavir and a biotin conjugate of indinavir.

Throughout the specification, numbers in boldface type are used refer to chemical structures illustrated in the drawings.

DETAILED DESCRIPTION OF THE INVENTION

As used herein, analyte refers to a substance, or group of substances, whose presence of amount thereof is to be determined.

Antibody means a specific binding partner of the analyte and is any substance, or group of substances, which has a specific binding affinity for the analyte to the essential exclusion of other unrelated substances. The term includes polyclonal antibodies, monoclonal antibodies and antibody fragments.

Haptens are partial or incomplete antigens. They are protein-free substances, mostly low molecular weight substances, which are not capable of stimulating antibody formation, but which do react with antibodies. The latter are formed by coupling a hapten to a high molecular weight carrier and injecting this coupled product into humans or animals. Examples of haptens include therapeutic drugs such as digoxin and theophylline, drugs of abuse such as morphine said LSD, antibiotics such as gentamicin and vanocomycin, hormones such as estrogen and progesterone, vitamins such as vitamin B12 and folic acid, thyroxin, histamine, serotonin, adrenaline and others.

An activated hapten refers to a hapten derivative that has been provided with an available site for reaction, such as by the attachment of, or furnishing of, an activated group for synthesizing a derivative conjugate.

The term linker refers to a chemical moiety that connects a hapten to a carrier, immunogen, label, tracer or another linker. Linkers may be straight or branched, saturated or unsaturated carbon chains. They may also include one or more heteroatoms within the chain or at termini of the chains. By heteroatoms is meant atoms other than carbon which are chosen from the group consisting of oxygen, nitrogen and sulfur. The use of a linker may or may not be advantageous or needed, depending on the specific hapten and carrier pairs.

A carrier, as the term is used herein, is an immunogenic substance, commonly a protein, that can join with a hapten, thereby enabling the hapten to stimulate an immune response. Carrier substances include proteins, glycoproteins, complex polysaccharides and nucleic acids that are recognized as foreign and thereby elicit an immunologic response from the host.

The terms immunogen and immunogenic as used herein refer to substances capable of producing or generating an immune response in an organism.

The terms conjugate and derivative refer to a chemical compound or molecule made from a parent compound or molecule by one or more chemical reactions.

As used herein, a detector molecule, label or tracer is an identifying tag which, when attached to a carrier substance or molecule, can be used to detect an analyte. A label may be attached to its carrier substance directly or indirectly by means of a linking or bridging moiety. Examples of labels include enzymes such as β-galactosidase and peroxidase, fluorescent compounds such as rhodamine and fluorescein isothiocyanate (FITC), luminescent compounds such as dioxetanes and luciferin, and radioactive isotopes such as $^{125}$I.

The term active ester within the sense of the present invention encompasses activated ester groups which can react with nucleophiles such as, but not limited to, free amino groups of peptides, polyaminoacids, polysaccharides or labels under such conditions that no interfering side reactions with other reactive groups of the nucleophile-carrying substance can usefully occur.

An object of the present invention is to provide novel activated haptens that can be used to generate immunogens to HIV protease inhibitors. These activated haptens take the general structure:

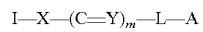

wherein I is an HIV protease inhibitor radical, X is O or NH, Y is O, S, or NH, m is 0 or 1, L is a linker consisting of from 0 to 40 carbon atoms arranged in a straight chain or a branched chain, saturated or unsaturated, and containing up to two ring structures and 0-20 heteroatoms, with the proviso that not more than two heteroatoms may be linked in sequence, and A is an activated functionality chosen from the group consisting of active esters, isocyanates, isothiocyanates, thiols, imidoesters, anhydrides, maleimides, thiolactones, diazonium groups and aldehydes.

As used herein, an HIV protease inhibitor radical is the intact drug lacking only a hydroxyl group or an amino group, XH, where X is O or NH. The X and C=Y moieties include, but are not limited to, esters (where X is O, Y is O, and m is 1), amides (where X is NH, Y is O, and m is 1), urethanes (where X is O, Y is O, m is 1, and the first atom in L adjacent to C=Y is N), ureas (where X is NH, Y is O, m is 1, and the first atom in L adjacent to C=Y is N), thioureas (where X is NH, Y is S, m is 1, and the first atom in L adjacent to C=Y is N), amidines (where X is NH, Y is NH, and m is 1), ethers (where X is O, and m is 0) and amines (where X is NR wherein R is H or lower alkyl, and m is 0). "Lower alkyl" means methyl, ethyl, propyl and isopropyl groups. Preferred activated haptens are esters or urethanes formed with the central, non-terminal hydroxyl group common to all HIV protease inhibitors. This central hydroxyl group is functionally important for the therapeutic activity of the protease inhibitors but also provides a convenient handle for derivatization and linker attachment. Moreover, generally the metabolism of the protease inhibitors takes place at terminal residues, and therefore the central hydroxyl groups are attractive sites for immunogens designed to generate antibodies which discriminate between parent drug and metabolites. As used herein, this central hydroxyl group is designated as HO$^c$. When the hydrogen of the central hydroxyl group is replaced by a (C=Y)$_m$-L-A group, the residual bonded oxygen is shown as O$^c$.

The linker L serves the purpose of providing an additional spacer between the terminal activated functionality A and the HIV protease inhibitor radical, the first spacer being the X and C=Y groups. Linker length and composition are well known to those skilled in the art to have important effects on immunogen response and conjugate performance. There are many examples of commercially available or easily synthesized linkers in the literature for attachment to hydroxyl and amino groups. For a good treatise on this subject, the reader is referred to *Bioconjugate Techniques,* G. Hermanson, Academic Press, 1996, In some cases the additional linker L is dispensed with and the C=Y moiety is directly attached to an activated functionality A. An example of a preferred linker moiety L is —(CH$_2$)$_x$—NH— where x is 1-12. Particularly preferred is x=5 in combination with C=Y where Y is O (i.e., aminocaproyl esters). Such linkers are formed by acylation of an HIV protease inhibitor with an N-protected amino acid (i.e., aminocaproic acid). The protecting group is preferably one which is removed under mildly basic or acidic conditions so as not to affect the integrity of the X—C=Y bonds or other moieties in the HIV protease inhibitor radical. An example of an N-protecting group removed under mildly basic conditions is fluorenylmethyloxcarbonyl (FMOC). An example of an N-protecting group easily removed with acid is t-butyloxycarbonyl (BOC). Many other suitable N-protecting groups are well known in the art (see "Protective Groups" in *Organic Synthesis*, 2nd, edition, T. Greene and P. Wuts, Wiley-Interscience, 1991).

The acylation reaction of HIV protease inhibitor hydroxyl or amino groups with N-protected amino acids is accomplished by using condensation reagents such as carbodiimides with or without a catalyst. A preferred combination is dicyclohexylcarbodiimide with dimethylaminopyridine as catalyst. The acylation reaction is carried out in a suitable solvent such as methylene chloride at 0-35° C. for a time which typically ranges from 0.5 to 7 days. Following isolation of the product, the N-protecting group is removed. For the preferred FMOC protecting group, this is accomplished by treatment with a solution of 10% piperidine in methylene chloride for 0.5 to 2 hours. The amino group of the resultant aminoacyl-protease inhibitor is amenable to acylation reactions with a wide variety of carboxyl activated linker extensions or labels which are well known to those skilled in the art to which the present invention belongs. Linker extension is often performed at this stage to generate terminal activated groups A such as active esters, isocynates and maleimides. For example, reaction of the aminoacyl-protease inhibitor with one end of homobifunctional N-hydroxysuccinimide esters of bis-carboxylic acids such as terephthalic acid will generate stable N-hydroxysuccinimide ester terminated linker adducts which are useful for conjugation to amines on polypeptides, polysaccharides, and labels. Linker extension can also be accomplished with heterobifunctional reagents such as maleimido alkanoic acid N-hydroxysuccinimide esters to generate terminal maleimido groups for subsequent conjugation to thiol groups on polypeptides and labels. Alternatively, an amino-terminated linker can be extended with a heterobifunctional thiolating reagent which reacts to form an amide bond at one end and a free or protected thiol at the other end. Some examples of thiolating reagents of this type which are well known in the art are 2-iminothiolane (2-IT), succinimidyl acetylthiopropionate (SATP) and succinimido 2-pyridyldithiopropionate (SPDP). The incipient thiol group is then available, after deprotection, to form thiol ethers with maleimido or bromacetylated modified immunogens or labels. Yet another alternative is to convert the amino group of the amino-terminated linker into a diazonium group and hence the substance into a diazonium salt, for example, by reaction with an alkali metal nitrite in the present of acid, which is then reactive with a suitable nucleophilic moiety, such as, but not limited to, the tyrosine residues of peptides, proteins, polyaminoacids and the like. Examples of suitable amino-terminated linkers for conversion to such diazonium salts include aromatic amines (anilines), but may also include the aminocaproates and similar substances referred to above. Such anilines may be obtained by substituting into the coupling reaction between the hydroxyl of a protease inhibitor and an N-protected amino acid, as discussed above, the corresponding amino acid wherein the amino group is comprised of an aromatic amine, that is, an aniline, with the amine suitably protected, for example, as an N-acetyl or N-trifluoracetyl group, which is then deprotected using methods well-known in the art. Other suitable amine precursors to diazonium salts will be suggested to one skilled in the art of organic synthesis.

Another favored type of heterobifunctional linker is a mixed active ester/acid chloride such as succinimido-oxycarbonyl-butyryl chloride. The more reactive acid chloride end of the linker preferentially acylates amino or hydroxyl groups on the HIV protease inhibitor to give N-hydroxysuccinimidyl ester linker adducts directly (see Examples 40 for amprenavir and 8 for ritonavir).

Yet another types of terminal activated group useful in the present invention is an aldehyde group. Aldehyde groups may be generated by coupling the hydroxyl of the protease inhibitor with an alkyl or aryl acid substituted at the omega position (the distal end) with a masked aldehyde group such as an acetal group, such as 1,3-dioxolan-2-yl or 1,3-dioxan-2-yl moieties, in a manner similar to that described previously, followed by unmasking of the group using methods well-known in the art. (See, e.g., T. Greene and P. Wuts, supra). Alternatively, alkyl or aryl carboxylic acids substituted at the omega position with a protected hydroxy, such as, for example, an acetoxy moiety, may be used in the coupling reaction, followed by deprotection of the hydroxy and mild oxidation with a reagent such as pyridinium dichromate in a suitable solvent, preferably methylene chloride, to give the corresponding aldehyde. Other methods of generating aldehyde-terminated substances will be apparent to those skilled in the art.

In certain cases, it is desirable to introduce polarity into the linker composition to improve solubility or performance characteristics in the assay of interest. Particularly useful in this regard are peptide linkers, which offer a wide diversity of possibilities for optimization and are readily accessible by solid phase peptide synthesis or by other means.

Another approach which is particularly useful for generating acylated HIV protease inhibitors with urethane, urea or thiourea bonds at the point of attachment to the protease inhibitor is to react the hydroxyl or amino group of the protease inhibitor with a linker isocyanate or a linker isothiocyanate. For example, a carboxyalkylisocyanate with or without a protecting group on the carboxyl group may be reacted directly with the target hydroxyl group on a protease inhibitor to give a protected carboxyalkylurethane or a carboxyarylurethane. The protected carboxy is preferably an ester which is removed under basic or acidic conditions. Once freed, the carboxyl group may be activated to give an active ester for subsequent conjugation or which may be directly conjugated to polypeptides, polysaccharides and labels. Alternatively, a preactivated carboxyalkylisocyanate or carboxyalkylisocyanate such as N-hydroxysuccinimidyl-isocyanatobenzoate may be reacted directly with protease inhibitor hydroxyl or amine groups to give linker-acylated protease inhibitor with an active ester terminus.

Yet another approach for generating urethane, urea and thiourea bonds at the point of attachment to the HIV protease inhibitor is to first treat the target hydroxyl or amine function with phosgene or thiophosgene to give an oxycarbonyl chloride or oxythiocarbonyl chloride. The latter intermediates react readily with amines to give urethanes, ureas or thioureas. Alternative phosgene equivalents such as carbonyldiimidazole or disuccinimidyl-carbonate will react similarly.

Another approach is also useful for generating alkylated derivatives of HIV protease inhibitors out of the central hydroxyl group. For example, a protease inhibitor (or properly protected protease inhibitor) can be reacted with a strong base under suitable conditions to deprotonate the central hydroxyl group. This can be reacted with a variety of halo alkyl reagents bearing a protected carboxylic acid or appropriately protected functionality such as an amino group protected as the phthalimide to form ether linkages. The protected carboxyl group is preferably an ester which is removed under acid or basic conditions. The free carboxylic acid group may be activated to give an active ester for subsequent conjugation to polypeptides, polysaccharides and labeling groups. The free amino group, after deprotection, can also be extended using a bi-functional linker with an activated carboxylic acid group or it can be coupled to a polypeptide by means of a urea linkage or similar group.

For generation of amidine adducts, the amine of an HIV protease inhibitor is reacted with an imidoester, many of which are known in bioconjugate chemistry as linkers (see Hermanson, ibid.).

Alternatively, protease inhibitors derivatized with linkers bearing an imidate moiety (imido ester; or iminium group) as the activated group may be obtained by, for example, using a linker carrying a suitable precursor group, for example, a terminal nitrile group, when appropriately functionalizing a protease inhibitor. For example, an $O^c$-alkylated derivative, or an $O^{35}$-alkyl derivative, for example, of nelfinavir, or $N^{ar}$alkyl derivative, for example, of amprenavir, carrying a terminal nitrile may be synthesized in a manner analogous to that described above, followed by conversion of the nitrile to an imidate group by methods known in the art, for example, by treatment with hydrogen chloride in an alcohol. See also: Hermanson, ibid; and Jerry March, *Advanced Organic Chemistry*, $3^{rd}$ Ed., John Wiley & Sons, 1985. Other methods of obtaining imido esters will be suggested to one skilled in the art.

In certain protease inhibitors with multiple hydroxy groups, i.e., indinavir and nelfinavir, or hydroxy groups and amino groups in the same protease inhibitor, i.e., amprenavir, it may be necessary to protect one of the groups in order to effect clean reaction at the other functional group. For example, the indinavir indane hydroxyl group can be protected with an isopropylidine group bridging to the adjacent amide nitrogen (see compound 4A, Example 4). For the purposes of this application the indane hydroxyl group is labeled as $HO^{in}$ to distinguish it from $HO^c$. The isopropylidine protected indinavir $HO^{in}$ by extension is designated as $O^{in}N^{in}$-isopropylidinyl.

In another example, nelfinavir aromatic hydroxyl ($HO^{ar}$ as used herein) is protected with a t-butyldimethylsily (TBDMS) group before reaction with the central hydroxyl group, $HO^c$ (see compound 5A, Example 5). Nelfinavir aromatic hydroxyl is also protected with a methoxy ethoxymethyl ether (MEM) group (see compound 5M, Example 31). Many other suitable protecting groups for alcohols and phenols are known in the art, and the reader is again referred to Greene and Wuts, ibid, for further examples.

In other cases, adjustment of the reaction conditions will allow for selection of one functional group over another, and protection will not be needed. An example of the latter approach is the selective acylation of amprenavir hydroxyl group or amino group (see Examples 3 and 40). Another example is the selective alkylation of nelfinavir phenolic hydroxyl group ($HO^{ar}$) in the presence of unprotected aliphatic central hydroxyl group ($HO^c$, see Example 36).

From the description above, it is evident that there are many variations of linker technology which will provide an activated terminal group A in the HIV protease inhibitor hapten compositions of interest. Some of these variations will not be described in more detail. Active esters are the most preferred A group. Active esters of the invention are reactive with nucleophiles, especially primary amines, at relatively low temperatures, generally 0-100° C. in a variety of aqueous and non-aqueous solvent mixtures. Typical conditions for active ester couplings with primary or secondary amines to give amides are reaction in dipolar aprotic solvents such as N,N-dimethylformamide (DMF) or dimethylsulfoxide (DMSO) with or without added water at room temperature. A buffer or a tertiary amine is often added to maintain the basic pH needed to keep the primary amine reactant in a deprotonated state. Typical active esters are p-nitrophenyl esters, N-hydroxysulfosuccinimidyl esters, N-hydroxysuccinimidyl esters, 1-hydroxybenzotriazolyl esters and pentafluorophenyl esters. Especially preferred are the N-hydroxysuccinimidyl esters because of their balance of stability, reactivity and the easy removal of side product N-hydroxysuccinimide. Other active esters are well known to those skilled in the art and may be used similarly.

An alternative activation method for protease inhibitor linkers terminated with carboxylic acids is in situ preparation of anhydrides. Particularly preferred are the mixed carbonic anhydrides formed with alkylchloroformates such as isobutylchloroformate. These mixed anhydrides are readily formed at temperatures typically ranging from −30° C. to +30° C., usually −20° C., to 0° C., by the reaction of carboxylic acid and alkylchloroformate in the presence of a tertiary amine such as triethylamine or N-methylmorpholine is solvents such as DMF or tetrahydrofuran (THF) for 5 minutes to 1 hour. The mixed anhydride is then reacted with amino groups on labels, immunogens and carriers, typically for 5 minutes to 1 hour at 0° C. to +30° C. to give stable amide conjugates. Also, symmetrical anhydrides may be formed by reaction of two equivalents of a protease inhibitor linker carboxylic acid group with carbodiimides such as dicyclohexylcarbodiimides (DCC) or ethyl-dimethylaminopropyl-carbodiimide (EDAC) in a variety of solvents such as THF, DMF or dichloromethane. The activation and coupling to amines is typically carried out under similar conditions as the mixed anhydride coupling above.

Yet another activation method for protease inhibitor linkers terminated with carboxylic acids is conversion to masked thiol groups, such as thiolactones, by coupling of the carboxylic acid group with a substance such as homocystein thiolactone. (See, e.g., U.S. Pat. No. 5,302,715.) The resulting linker-thiolactone may then be unmasked with mild base to give a terminal thiol which is then reactive with moieties like maleimido groups or bromoacetyl or iodoacetyl groups, such as on maleimido- or haloacetyl-modified peptides, polysaccharides, polyaminoacids, labels and the like, to give thio-maleimido or thio-acetyl adducts in a similar manner to that described previously.

Other useful A groups are isothiocyanate or isocyanate moieties. Isothiocyanates also react readily with nucleophiles such as primary amines to give thioureas under conditions similar to the active ester reaction described above, while isocyanates react similarly to give ureas. An added advantage of the isothiocyanate or isocyanate reaction is that it is an addition rather than a substitution, and therefore there is no side-product to be concerned about as in the case of active esters. Isocyanate equivalent, such as, for example, p-nitrophenyloxycarbonylamino moieties react similarly with primary amines to give ureas Finally, when the target nucleophile is a thiol group, maleimides are especially preferred because of their rapid formation of thio esters under very mild conditions, i.e., ambient temperature and neutral pH. Alternatively, active haloalkyl A groups such as iodoacetyl or bromoacetyl also react readily to form stable thio ethers.

Another object of the invention is to provide novel immunogens with the following structure:

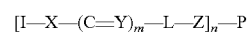

wherein I is an HIV protease inhibitor radical, X is O or NH, Y is O, S, or NH, m is 0 or 1, L is a linker consisting of from 0 to 40 carbon atoms arranged in a straight chain or a branched chain, saturated or unsaturated, and containing up to two ring structures and 0-20 heteroatoms, with the proviso that not more than two heteroatoms are linked in sequence, Z is a moiety chosen from the group consisting of —CONH—, —NHCO—, —NHCONH—, —NHCSNH—, —OCONH—, —NHOCO—, —S—, —NH(C=NH)—, —N=N—, —NH—, and

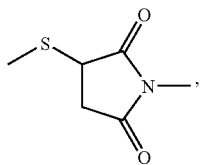

P is a polypeptide, a polysaccharide or a synthetic polymer, and n is a number from 1 to 50 per 50 kilodaltons molecular weight of P.

For immunogens, the preferred mode of the invention is to link from the central hydroxyl group common to all HIV protease inhibitors by an acylation reaction to form an ester bond (i.e., X is O, m is 1 and Y is O). A wide variety of linkers L and activated functionalities A may be used as described above. Thus an activated hapten of the type I—X—(C=Y)m-L-A is constructed and reacted with an immunogenic carrier substance. The immunogenic carrier is typically a polypeptide or a polysaccharide with a molecular weight more than 10 kD. Preferred immunogenic carriers are polypeptides with a molecular weight more than 100 kD. Examples of preferred carrier substances are keyhole limpet hemocyanin (KLH), *Limulus polyphemus* hemocyanin (LPH) and bovine thyroglobulin (BTG). The reaction between the activated hapten and amino groups on the carrier is typically carried out in a buffered mixture of water and a water miscible organic solvent such as DMSO at room temperature for 0.5 to 5 days. The pH of the buffer is typically between 6 and 8 for active esters, isocyanates, and isothiocyanates, or between 7 and 10 for imidates, and is adjusted according to the known reactivity of the carrier amino groups and the activated functionality. In the case where the terminal group A is a maleimide, the reactive groups on the carrier are thiols. These thiol groups are either native to the carrier or may be introduced using thiolating reagents such as 2-IT or SATP. The optimum pH for the conjugation of maleimides to thio groups to give thioethers is typically between 5 and 7. Following the reaction, the immunogen is dialyzed or subjected to size exclusion chromatography in order to remove unconjugated hapten and organic solvent.

An alternative method of obtaining immunogens is to react an activated hapten wherein A is aldehyde with the amino groups of a carrier protein or polypeptide to form a Schiff base, followed by reduction with mild reducing agents such as cyanoborohydride, to form a stable amine bond. Variations on this last approach will also be suggested to those skilled in the art to which the present invention belongs.

Yet another object of the present invention is to provide antibodies to HIV protease inhibitors generated from the immunogens of the invention. In order to generate antibodies, the immunogen can be prepared for injection into a host animal by rehydrating lyophilized immunogen to form a solution or suspension of the immunogen. Alternatively, the immunogen may be used as a previously prepared liquid solution or as a suspension in buffer. The immunogen solution is then combined with an adjuvant such as Freund's to form an immunogen mixture. The immunogen may be administered in a variety of sites, at several doses, one or more times, over many weeks.

Preparation of polyclonal antibodies using the immunogens of the invention may follow any of the conventional techniques known to those skilled in the art. Commonly, a host animal such as a rabbit, goat, mouse, guinea pig, or horse is injected with the immunogen mixture. Further injections are made, with serum being assessed for antibody titer until it is determined that optimal titer has been reached. The hose animal is then bled to yield a suitable volume of specific antiserum. Where desirable, purification steps may be taken to remove undesired material such as nonspecific antibodies before the antiserum is considered suitable for use in performing assays.

Monoclonal antibodies may be obtained by hydridizing mouse lymphocytes, from mice immunized as described above, and myeloma cells using a polyethylene glycol method such as the technique described in *Methods in Enzymology* 73 (*Part B*), pp. 3-46, 1981.

In the case of ELISA assays, protease inhibitor derivatives coupled to bovine serum albumin (BSA) are preferred for coating of microtiter plates.

Another object of the invention is to provide novel labeled conjugates with the following structure:

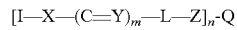

wherein I is an HIV protease inhibitor radical, X is O or NH, Y is O, S, or NH, m is 0 or 1, L is a linker consisting of from 0 to 40 carbon atoms arranged in a straight chain or a branched chain, saturated or unsaturated, and containing up to two ring structures and 0-20 heteroatoms, with the proviso that not more than two heteroatoms are linked in sequence, Z is a moiety chosen from the group consisting of —CONH—, —NHCO—, —NHCONH—, —NHCSNH—, —OCONH—, —NHOCO—, —S—, —NH(C=NH)—, N=N—, —NH—, and

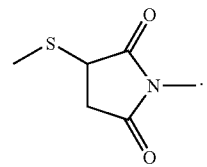

Q is a non-isotopic label, and n is a number from 1 to 50 per 50 kilodaltons molecular weight of Q.

For the synthesis of conjugates of HIV protease inhibitors and non-isotopic labels, similar procedures as for the preparation of immunogens are employed.

Alternatively, the activated haptens may be conjugated to amino or thiol groups on enzymes to prepare labels for the ELISA application. Some examples of useful enzymes for ELISA for which conjugates are well-known in the art are horseradish peroxidase (HRP), alkaline phosphatase and β-galactosidase. Conjugates of proteins including enzymes are typically prepared in a buffered mixture of water and water miscible organic solvents followed by dialysis analogous to the conditions for preparation of immunogens. In the case of latex agglutination assays, conjugates with aminated dextran carriers having molecular weights between 10 kD and 300 kD, preferably 40 kD, are especially useful. These conjugates are prepared in buffered solvent mixtures as above or in an anhydrous organic solvent such as DMSO containing a tertiary amine such as triethylamine to promote the reaction. In the case of labels of small molecular weight, i.e., less than 1 kD, reaction conditions are adjusted according to the nature of the label. One label which is particularly preferred is biotin in combination with labeled avidin or streptavidin. The versatility of (strept)avidin/biotin systems for non-isotopic detection is well known in the art of bio-conjugate chemistry (see Hermanson, ibid.). A variety of enzyme- and fluorophore-labeled conjugates of avidin and streptavidin are commercially available to detect biotin-labeled substances in a high affinity interaction. Furthermore, a variety of biotinylating agents are commercially available to react with activated functionalities A. For example, a biotin-amine derivative may be reacted with activated haptens of the invention in which A is an active ester, isocyanate or isothiocyanate to give biotin amide, urea and thiourea conjugates respectively. These coupling reactions are typically carried out in a dipolar aprotic solvent such as DMF or DMSO containing an organic base such as triethylamine at room temperature for 0.5 to 5 days. The biotin conjugates are preferentially isolated by chromatographic methods such as reversed phase HPLC.

Other preferred labels are fluorophores such as fluorescein, rhodamine, TEXAS RED fluorescent dye (Molecular Probes, Inc.), dansyl, and cyanine dyes, e.g., Cy-5, of which many activated derivatives are commercially available. Generally, these conjugates may be prepared similarly as biotin conjugates in a dipolar aprotic solvent containing a tertiary amine followed by chromatographic isolation.

It is also possible to use a reporter group as label which is indirectly coupled to a detection system. One example is biotin as described above. Another example is mycophenolic acid derivatives for inhibition of inosine monophosphate dehydrogenase as described in PCT publication WO 200101135, published Jan. 4, 2001.

It will be obvious to those skilled in the art that there are other possibilities for non-isotopic labels including electrochemiluminescent labels such as ruthenium bipyridyl derivatives, chemiluminescent labels such as acridinium esters, electrochemical mediators, and a variety of microparticles and nanoparticles which can be used for the invention after suitable introduction of suitable nucleophilic groups on the label, e.g., amines or thiols, for reaction with activated groups A on the HIV protease inhibitor activated hapten.

SPECIFIC EMBODIMENTS

In the examples that follow, numbers in boldface type refer to the corresponding structure shown in the drawings. These examples are presented for illustration only without any intent to limit the invention.

O-Acylation of Protease Inhibitors

EXAMPLE 1

Synthesis of $O^c$—(N-FMOC-aminocaproyl-ritonavir (1A)

Ritonavir (1, 0.3605 g), FMOC-aminocaproic acid (0.1944 g, Advanced ChemTech, Louisville, Ky.), dimethylaminopyridine (0.0672 g, Aldrich Chemical Co., Milwaukee, Wis.) and dicyclohexylcarbodiimide (0.1238 g, Fluka Chemical Corp., Milwaukee, Wis.) were stirred overnight in anhydrous methylene chloride (5 mL) at room temperature. The mixture was filtered, and the filtrate was evaporated to dryness under reduced pressure and directly purified by silica gel (EM Science Cat. No. 9385-9, silica gel 60, 230-400 mesh ASTM) chromatography under a positive pressure of nitrogen (3% methanol in chloroform elution) to yield $O^c$—(N-FMOC-aminocaproyl)-ritonavir (1A) as a white solid (0.5023 g, 95%), M−H 1056.2

EXAMPLE 2

Synthesis of $O^c$—(N-FMOC-aminocaproyl)-saquinavir (2A)

$O^c$—(N-FMOC-aminocaproyl)-saquinavir (2A) was prepared from saquinavir methanesulfonate (2, 0.1917 g) following the conditions described in Example 1, except more methylene chloride (75 mL) was used and the reaction was stirred for 2 days. (A. Farese-Di Giorgio et al., *Antiviral Chem. and Chemother.* 11, 97-110, 2000) (0.2354 g, 94%). M+H 1006.2

EXAMPLE 3

Synthesis of $O^c$—(N-FMOC-aminocaproyl)-amprenavir (3A)

$O^c$—(N-FMOC-aminocaproyl)-amprenavir (3A) was prepared from amprenavir (3) (0.1517 g) following the conditions described in Example 1 (0.2248 g; 89%). M+H 841

EXAMPLE 4

Synthesis of $O^c$—(N-FMOC-aminocaproyl)-$O^{in}$,$N^{in}$-isopropylidinyl-indinavir (4B)

Indinavir sulfate (4, 0.3559 g), camphorsulfonic acid (0.1401 g, Aldrich Chemical Co.), and magnesium sulfate (4 mg) were refluxed overnight in dimethoxypropane (5 mL, A. Farese-Di Giorgio et al., *Antiviral Chem. and Chemother*, 11, 97-110, 2000). The mixture was partitioned between methylene chloride and saturated aqueous sodium bicarbonate. The organic layer was evaporated to dryness under reduced pressure and directly purified by silica gel chromatography (4% methanol in chloroform elution) to yield $O^{in}$,$N^{in}$-isopropylidyl-indinavir (4A) as a colorless oil (0.2350 g; 72%). M+H 654.4.

$O^c$—(N-FMOC-aminocaproyl)-$O^{in}$,$N^{in}$-isopropylidinyl-indinavir (4B) was prepared in $O^{in}$,$N^{in}$-isopropylidyl-indinavir (4A, 0.1317 g) following the conditions described in Example 1 (0.1742 g; 87%). M+H 989.4

EXAMPLE 5

Synthesis of $O^c$—(N-FMOC-aminocaproyl)-$O^{ar}$-TBDMS-nelfinavir (5B)

Nelfinavir (5, 0.2839 g) and sodium hydride (18 mg) were stirred in DMF (3 mL) for 15 minutes. t-Butyldimethylsily (TBDMS) chloride (0.1130 g) was added and the reaction was stirred overnight. The mixture was evaporated to dryness under reduced pressure and directly purified by silica gel chromatography (3% methanol in chloroform elution) to yield $O^{ar}$-TBDMS-protected nelfinavir (5A) as a white foam (0.2857 g; 84%). M+H 682.4.

$O^c$—(N-FMOC-aminocaproyl)-$O^{ar}$-TBDMS-nelfinavir (5B) was prepared from $O^{ar}$-TBDMS protected nelfinavir

EXAMPLE 6

Synthesis of $O^c$—(N-FMOC-aminocaproyl)-lopinavir (6A)

$O^c$—(N-FMOC-aminocaproyl)-lopinavir (6A) was prepared from lopinavir (6, 0.712 g) following the conditions described in Example 1 (0.500 g; 45%). M–H 964.4

EXAMPLE 7

Synthesis of $O^c$-[3-(4'-carboxyphenyl)-propionyl]-saquinavir (2H)

3-(4'-Carboxyphenyl)-propionyl-saquinavir (2H) was prepared from saquinavir methanesulfonate (2, 0.1534 g) and 3-(4'-carboxyphenyl)-propionic acid (0.0485 g, Lancaster Synthesis Inc., Windham, N.H.) following the conditions described in Example 1 (0.1041 g; 61%). M+H 847.4. Spectral data ($^1$H-NMR) for the product was compatible was esterification at the alkyl carboxy rather than the aryl carboxy.

EXAMPLE 8

Synthesis of $O^c$-(succinimido-oxycarbonyl-butyryl)-ritonavir (1G)

Succinimido-oxycarbonyl-butyryl chloride, i.e., 5-(2,5-dioxo-1-pyrrolidinyl-oxy)-5-oxy-pentanoyl chloride, is prepared according to Antonian et al., EP 0 503 454. Ritonavir (1, 0.2163 g) and succinimido-oxycarbonyl-butyryl chloride (0.0817 g) were stirred overnight in anhydrous DMF (3 mL) at 50° C. The mixture was evaporated to dryness under reduced pressure and directly purified by silica gel chromatography (30% tetrahydrofuran in ethyl acetate elution) to yield $O^c$-(succinimido-oxycarbonyl-butyryl)-ritonavir (1G) as a white solid (0.1220 g, 44%). M+H 931.8

Deprotection of O-Acylated Protease Inhibitors

EXAMPLE 9

Synthesis of $O^c$-(aminocaproyl)-ritonavir (1B)

$O^c$—(N-FMOC-aminocaproyl)-ritonavir (1A) from Example 1 (0.2113 g) was stirred 1 hour in 10% piperidine in anhydrous methylene chloride (4 mL) at room temperature. The mixture was evaporated to dryness under reduced pressure and directly purified by silica gel chromatography (20-25% methanol in chloroform gradient elution) to yield $O^c$-(aminocaproyl)-ritonavir (1B) as a white solid (0.1525 g, 91%). M+H 834

EXAMPLE 10

Synthesis of $O^c$-(aminocaproyl)-saquinavir (2B)

$O^c$-(aminocaproyl)-saquinavir (2B) was prepared from O—(N-FMOC-aminocaproyl)-saquinavir (2A) of Example 2 (0.7547 g) following the conditions described in Example 9 (0.5253 g; 89%). M+H 784.3

EXAMPLE 11

Synthesis of $O^c$-(aminocaproyl)-amprenavir (3B)

$O^c$-(aminocaproyl)-amprenavir (3B) was prepared from O—(N-FMOC-aminocaproyl)-amprenavir (3A) of Example 3 (0.2523 g) following the conditions described in Example 9 (0.1160 g; 63%). M+H 619.3

EXAMPLE 12

Synthesis of $O^c$-(aminocaproyl)-indinavir (4D)

$O^c$—(N-FMOC-aminocaproyl)-$O^{in}$,$N^{in}$-isopropylidinyl-indinavir (4B) synthesized as in Example 4 (0.5869 g) was stirred overnight in 50% trifluoroacetic acid in anhydrous methylene chloride (6 mL) at room temperature to remove the isopropylidinyl protecting group. The mixture was evaporated to dryness under reduced pressure, the residue partitioned between methylene chloride and saturated aqueous sodium bicarbonate. The organic layer was separated, dried (sodium sulfate), and evaporated to a light yellow foam (0.5329 g). The foam was dissolved in 5% piperidine in anhydrous methylene chloride (5 mL) and stirred overnight. Solvent was removed and the off-white residue purified by silica gel chromatography (eluting with 5:1 chloroform/methanol containing 1% concentrated aqueous ammonium hydroxide) to give $O^c$-(aminocaproyl)-indinavir (4D) as a colorless oil (0.2866 g; 66% overall). M+H 727.5

In another run, $O^c$—(N-FMOC-aminocaproyl)-$O^{in}$,$N^{in}$-isopropylidinyl-indinavir (4B) from Example 4 (0.2301 g) was stirred 2 hours in 50% trifluoroacetic acid in anhydrous methylene chloride (3 mL) at room temperature to remove the isopropylidinyl protecting group. The mixture was evaporated to dryness under reduced pressure and directly purified by silica gel chromatography (5% methanol in chloroform elution) to yield $O^c$—(N-FMOC-aminocaproyl)-indinavir (4C) as a white foam (0.1603 g, 70%). M+H 949.3.

EXAMPLE 13

Synthesis of $O^c$-(aminocaproyl)-nelfinavir (5C)

$O^c$—(N-FMOC-aminocaproyl)-$O^{ar}$-TBDMS-nelfinavir (5B) from Example 5 (0.1752 g) and tetraethylammonium fluoride (0.2092 g) were stirred 2 hours in anhydrous THF (10 mL) at room temperature to remove both the TBDMS and FMOC protecting groups in one step. The mixture was evaporated to dryness under reduced pressure, redissolved in methylene chloride, washed with water then saturated aqueous sodium chloride (brine) and evaporated to dryness. The residue was purified by silica gel chromatography (elution with 2% to 10% methanol in chloroform gradient to remove front-running material, then 100% methanol to elute product) to yield $O^c$-(aminocaproyl)-nelfinavir (5C) as a white foam (0.0711 g, 75%). M+H 681.3

EXAMPLE 14

Synthesis of $O^c$-(aminocaproyl)-lopinavir (6B)

$O^c$-(aminocaproyl)-lopinavir (6B) was prepared from $O^c$—(N-FMOC-aminocaproyl)-lopinavir (6A, 0.100 g) of Example 6 following the conditions described in Example 9, except for purification by silica gel chromatography (10% methanol in chloroform containing 2% ammonium hydroxide) to yield product 6B (0.043 g; 56%). M+H 742.2

Another reaction, 0.300 g of (6A), performed in 10% piperidine in water instead of methylene chloride gave product (0.150 g; 65%) after evaporation and silica gel chromatography as described above.

Linker Extension of O-Acylated Protease Inhibitors to Generate Activated Haptens

EXAMPLE 15

Synthesis of $O^\varepsilon$-(succinimido-oxycarbonyl-butyryl-aminocaproyl)-ritonavir (1C)

$O^\varepsilon$-(aminocaproyl)-ritonavir (1B) from Example 9 (60.9 mg), triethylamine (10 µL), and succinimido-oxycarbonyl butyryl chloride (Antonian, ibid, 17.5 mg) were stirred 2 hours in anhydrous THF (6 mL) at 0° C. The mixture was evaporated to dryness under reduced pressure and directly purified by silica gel chromatography (30% THF in ethyl acetate elution) to yield $O^\varepsilon$-(succinimido-oxycarbonyl-butyryl-aminocaproyl)-ritonavir as a white solid (38.8 mg, 51%). M+H 1045.2

EXAMPLE 16

Synthesis of $O^\varepsilon$-[4'-(succinimido-oxycarbonyl)-benzoyl-aminocaproyl]-ritonavir (1D)

First, disuccinimidyl terephthalic was prepared by the method of Kopia et al., U.S. Pat. No. 5,667,764. To a stirring solution of disuccinimidyl terephthalic (21.6 mg) and triethylamine (8 µL) in anhydrous methylene chloride (8 mL) was slowly added a solution of $O^\varepsilon$-(aminocaproyl)-ritonavir (1B) from Example 9 (48.0 mg) in anhydrous methylene chloride (8 mL). The mixture was stirred 4 hours at room temperature under argon. The mixture was evaporated to dryness under reduced pressure and directly purified by silica gel chromatography (30% THF in ethyl acetate elution) to yield $O^\varepsilon$-[4'-(succinimido-oxycarbonyl)-benzoyl-aminocaproyl]-ritonavir as a white solid (41.6 mg, 67%). M+H 1079

EXAMPLE 17

Synthesis of $O^\varepsilon$-(succinimido-oxycarbonyl-butyryl-aminocaproyl-saquinavir (2C)

$O^\varepsilon$-(succinimido-oxycarbonyl-butyryl-aminocaproyl)-saquinavir (2C) was prepared from $O^\varepsilon$-(aminocaproyl)-saquinavir (2B) of Example 10 (52.8 mg) following the conditions described in Example 15, except that a gradient of 5% to 10% methanol in chloroform was used as the eluent in the silica gel chromatographic purification (48 mg; 72%). M−H 995.3

EXAMPLE 18

Synthesis of $O^\varepsilon$-[4-(succinimido-oxycarbonyl)-benzoyl-aminocaproyl]-saquinavir (2F)

$O^\varepsilon$-[4'-(succinimido-oxycarbonyl)-benzoyl-aminocaproyl]-saquinavir (2F) was prepared from $O^\varepsilon$-(aminocaproyl)-saquinavir (2B) of Example 10 (11 mg) following the conditions described in Example 16, but using 2% methanol in chloroform as the eluent in the silica gel chromatographic purification (12 mg; 83%). M+H 1029.3

EXAMPLE 19

Synthesis of $O^\varepsilon$-(succinimido-oxycarbonyl-butyryl-aminocaproyl)-amprenavir (3C)

$O^\varepsilon$-(succinimido-oxycarbonyl-butyryl-aminocaproyl)-amprenavir (3C) was prepared from $O^\varepsilon$-(aminocaproyl)-amprenavir (3B) of Example 11 (104.0 mg) following the conditions described in Example 15, but with stirring for 6 hours and the use of 5% methanol in chloroform as the eluent in the silica gel chromatographic purification (80 mg; 57%). M+Na 852.4

EXAMPLE 20

Synthesis of $O^\varepsilon$-[4'-(succinimido-oxycarbonyl)-benzoyl-aminocaproyl]-amprenavir (3D)

$O^\varepsilon$-[4'-(succinimido-oxycarbonyl)-benzoyl-aminocaproyl]-amprenavir (3D) was prepared from $O^\varepsilon$-(aminocaproyl)-amprenavir (3B) of Example 11 (86.5 mg) following the conditions described in Example 16, but using 4% methanol in chloroform as the eluent in the silica gel chromatographic purification (70.3 mg; 58%). M+Na 886.4

EXAMPLE 21

Synthesis of $O^\varepsilon$-(succinimido-oxycarbonyl-butyryl-aminocaproyl)-indinavir (4E)

$O^\varepsilon$-(succinimido-oxycarbonyl-butyryl-aminocaproyl)-indinavir (4E) was prepared from $O^\varepsilon$-(aminocaproyl)-indinavir (4D) of Example 12 (80.0 mg) following the conditions described in Example 15, but with stirring for 6 hours and with the use of a 5% rising to 17% methanol in chloroform gradient as the eluent in the silica gel chromatographic purification (37.4 mg; 36%). M+H 938.6

EXAMPLE 22

Synthesis of $O^\varepsilon$-[4'-(succinimido-oxycarbonyl)-benzoyl-aminocaproyl]-indinavir (4F)

$O^\varepsilon$-[4'-(succinimido-oxycarbonyl)-benzoyl-aminocaproyl]-indinavir (4F) was prepared from O-(aminocaproyl)-indinavir (4D) of Example 12 (90.0 mg) following the conditions described in Example 16, except that 5% methanol in chloroform was used as the eluent in the silica gel chromatographic purification (61.8 mg; 51%). M+H 972.6

EXAMPLE 23

Synthesis of $O^\varepsilon$-(succinimido-oxycarbonyl-butyryl-aminocaproyl)-nelfinavir (5D)

$O^\varepsilon$-(succinimido-oxycarbonyl-butyryl-aminocaproyl)-nelfinavir (5D) was prepared from $O^\varepsilon$-(aminocaproyl)-nelfinavir (5C) of Example 13 (60.0 mg) following the conditions described in Example 15, except that a 2% rising to 5% methanol in chloroform gradient was used as the eluent in the silica gel chromatographic purification (67.2 mg; 85%). M+H 892.5

EXAMPLE 24

Synthesis of O$^c$-[4'-(succinimido-oxycarbonyl)-benzoyl-aminocaproyl]-nelfinavir (5E)

O$^c$-[4'-(succinimido-oxycarbonyl)-benzoyl-aminocaproyl]-nelfinavir (5E) was prepared from O-(aminocaproyl)-nelfinavir (5C) of Example 13 (61.8 mg) following the conditions described in Example 16, except that 5% methanol, in chloroform was used as the eluent in the silica gel chromatographic purification (43.3 mg; 52%). M+H 926.6

EXAMPLE 25

Synthesis of O$^c$-(succinimido-oxycarbonyl-butyryl-aminocaproyl)-lopinavir (6C)

O$^c$-(succinimido-oxycarbonyl-butyryl-aminocaproyl)-lopinavir (6C) was prepared from O$^c$-(aminocaproyl)-lopinavir (6B) of Example 14 (86 mg) following the conditions described in Example 15, except for purification by silica gel chromatography (5% methanol in chloroform) (68 mg; 62%). M+H 953.4

EXAMPLE 26

Synthesis of O$^c$-[4'-(succinimido-oxycarbonyl)-benzoyl-aminocaproyl]-lopinavir (6D)

O$^c$-[4'-(succinimido-oxycarbonyl)-benzoyl-aminocaproyl]-lopinavir (6D) is prepared from O-(aminocaproyl)-lopinavir (6B) of Example 14 (80 mg) following the conditions described in Example 16, except for purification by silica gel chromatography (50% tetrahydrofuran in ethyl acetate) (35 mg; 33%). M+H 987.3

EXAMPLE 27

Synthesis of O$^c$-3-[4'-(succinimido-oxycarbonyl)-phenyl-propionyl]-saquinavir (2I)

O$^c$-3-[4'-(succinimido-oxycarbonyl)-phenyl-propionyl]-saquinavir was prepared from O$^c$-[3-(4'-carboxyphenyl)-propionyl)]-saquinavir (2H) of Example 7 following the conditions described in Example 38 (96%). M+H 944.5

EXAMPLE 28

Synthesis of N-maleimidopropionyl-L-glutamyl-(gamma-O$^c$-saquinavir)-L-alanine (2P)

Boc-L-Glu(OBzl)OSu (Bachem), 434 mg (1 mmol) is reacted with L-Ala-O'Bu. HCl, 182 mg (1 mmol) in 10 mL DMF containing triethylamine (202 mg). After stirring for 16 hours at room temperature, the reaction mixture is rotary evaporated to dryness and the residue is redissolved in methylene chloride, washed with water, dried over sodium sulfate and evaporated to dryness. The residue is redissolved in methanol, 50 mL, and transferred to a Parr flask. 10% Pd/C catalyst (Aldrich), 50 mg, is added and the flask is charged with 40 psi hydrogen gas on a Parr shaker. The mixture is shaken for 2 hours at room temperature or until no further consumption of hydrogen is noted. The Parr flask is evacuated and charged with argon gas. The mixture is filtered through Celite, and the filtrate is rotary evaporated to give crude Boc-L-Glu-L-Ala-O'Bu.

Saquinavir (335 mg), Boc-L-Glu-L-Ala-O'Bu (187 mg), dicyclohexylcarbodiimide (103 mg), hydroxybenzotriazole (67.5 mg), N-ethylmorpholine (57.5 mg), and dimethylaminopyridine (61 mg) were stirred overnight in anhydrous THF (5 mL). The reaction was diluted with ethyl acetate and filtered. The filtrate was washed with 2 M HCl, saturated aqueous sodium bicarbonate, and brine. The organic layer was evaporated to dryness under reduced pressure and directly purified by silica gel chromatography (5% methanol in methylene chloride elution) to yield N-t-butyloxycarbonyl-L-glutamyl-(gamma-O$^c$-saquinavir)-L-alanine t-butyl ester (2N) as an off-white foam (384 mg, 75%), M–H 1027

N-t-butyloxycarbonyl-L-glutamyl-(gamma-O$^c$-saquinavir)-L-alanine t-butyl ester (2N, 3.0 mg) was stirred 1 hour in 50% trifluoroacetic acid in anhydrous methylene chloride (0.05 mL) and evaporated in dryness under reduced pressure. The residue was dissolved in anhydrous methylene chloride (0.1 mL) and stirred 30 minutes with triethylamine (1 µL) and succinimidyl maleimidopropionate (synthesized by the method of Ede, Tregear and Haralambidis, *Bioconjugate Chem.* 5, 373-378, 1994; 0.9 mg). The mixture was evaporated to dryness under reduced pressure and directly purified by preparative TLC (25% methanol in chloroform development) to yield N-maleimidopropionyl-L-glutamyl-(gamma-O$^c$-saquinavir)-L-alanine (2P) as a white solid (1.7 mg, 57%). M+H 1022.3

EXAMPLE 29

Synthesis of N-maleimidopropionyl-L-Ala-L-Glu-(gamma-O$^c$-saquinavir) (2Q)

Boc-L-Ala-L-Glu-O'Bu is first synthesized using the procedure for Boc-L-Glu-L-Ala-O'Bu in Example 29 substituting L-Glu(OBzl)-O'Bu (Bachem) for L-Ala-O'Bu and Boc-L-Ala-Osu (Bachem) for Boc-L-Glu(OBzl)-Osu. Boc-L-Ala-L-Glu(gamma-Oc-saquinavir)-O'Bu (2O) was prepared from saquinavir (335 mg) and Boc-L-Ala-L-Glu-O'Bu (187 mg) following the conditions described in Example 28 for intermediate 2N (84%). M+H 1027

N-maleimidopropionyl-L-Ala-L-Glu-(gamma-O$^c$-saquinavir) (2Q) was prepared from N-t-Boc-L-Ala-L-Glu-(gamma-O$^c$-saquinavir)-O'Bu (2O, 3.0 mg) following the conditions described in Example 28 (57%). M+H 1022.3

EXAMPLE 30

Synthesis of O$^c$-(maleimido-propionyl-aminocaproyl)-saquinavir (2M)

O$^c$-(aminocaproyl)-saquinavir (2B) from Example 10 (0.1098 g), succinimidyl maleimidopropionate (0.048 g), and triethylamine (20 µL) were stirred 45 minutes in anhydrous methylene chloride (1.5 mL). The mixture was evaporated to dryness under reduced pressure and directly purified by silica gel chromatography (4% methanol in chloroform elution) to yield O$^c$-(maleimido-propionyl-aminocaproyl)-saquinavir (2M) as a colorless oil (0.0647 g, 49%). M+H 935.5

Alkylation of Protease Inhibitors at the Central Hydroxyl

EXAMPLE 31

Synthesis of O$^{ar}$-methoxyethoxymethyl-nelfinavir (5M)

To 28 mg (0.70 mmol) of NaH (60% in oil) was added 1 mL of hexane. The mixture was allowed to stir for 2-3 minutes under argon at room temperature and hexane was decanted. To the residue was added 1 mL of freshly distilled THF and 0.5 mL of anhydrous DMF followed by 50 mg (0.075 mmol) of nelfinavir mesylate as a solid in several portions. The mixture was heated at 50° C. for 45 minutes under argon and allowed to cool to room temperature. To the reaction mixture was added 12.5 µL (0.10 mmol) of 2-methoxyethoxymethyl chloride (MEM chloride) and allowed to stir at room temperature under argon for 18 hours. To the reaction mixture was added 1 mL of 50 mM potassium phosphate (pH 7.5) and the mixture was concentrated under reduced pressure. To the residue were added 25 mL of CHCl$_3$ and 15 mL of 50 mM potassium phosphate (pH 7.5). The organic layer was separated and the aqueous layer was extracted with additional 4×25 mL of CHCl$_3$. All the organic extracts were combined, dried (anhydrous Na$_2$SO$_4$) and concentrated. The crude product was purified by preparative thin layer chromatography (silica gel, EM Science Cat. No. 5717-7) using 20:1 CHCl$_3$:MeOH as eluting solvent to give 43 mg (0.065 mmol, 88%) of O$^{ar}$-methoxyethoxymethyl-nelfinavir (5M) as a white solid. M+H 656

EXAMPLE 32

Synthesis of O$^{ar}$-MEM-O$^c$-carboxymethyl-nelfinavir (5N)

To 14 mg (0.35 mmol) of NaH (60% in oil) was added 1 mL of hexane. The mixture was allowed to stir at room temperature under argon for 2-3 minutes and hexane was decanted. To the residue 2 mL of freshly distilled THF and 1 mL of anhydrous DMF was added. A solution of 23 mg (0.035 mmol) of 5M in 1 mL of freshly distilled THF was added to the reaction mixture. The reaction mixture was heated at 50° C. under argon for 1 hour and allowed to cool to room temperature. To the reaction mixture was added a solution of 6.5 µL (0.043 mmol) of t-butyl bromoacetate (Aldrich Chemical Co.) in 500 µL of freshly distilled THF, and the reaction mixture was allowed to stir at room temperature for 18 hours under argon. To the reaction mixture was added 1 mL of water and the mixture was concentrated under reduced pressure. To the residue were added 20 mL of CHCl$_3$ and 15 mL of water. The organic layer was separated and the aqueous layer was extracted with additional 4×20 mL of CHCl$_3$. All the organic extracts were combined, dried (Na$_2$SO$_4$) and concentrated. The crude product was purified by preparative thin layer chromatography (silica gel) using 20% methanol in chloroform as eluent to give 22 mg (0.031 mmol, 88%) of O$^{ar}$-MEM-O$^c$-carboxymethyl-nelfinavir (5N) as a white solid. M−H 714.

EXAMPLE 33

Synthesis of O$^{ar}$-MEM-O$^c$-(succinimido-oxycarbonyl-methyl)-nelfinavir (5O)

The activated ester (5O) is prepared from (5N) by following the procedure described in Example 38.

EXAMPLE 34

Synthesis of O$^c$-(carboxymethyl)-saquinavir (2AA)

To 65 mg (1.6 mmol) of NaH (60% in oil) was added 2 mL of hexane. The mixture was allowed to stir at room temperature under argon for 2-3 minutes and hexane was decanted. To the residue 2 mL of freshly distilled THF and 1 mL of anhydrous DMF was added. Saquinavir mesylate (2, 112 mg, 0.14 mmol) was added to the reaction mixture as a solid in several portions. The reaction mixture was heated at 50° C. for 1 hour and allowed to cool to room temperature. To the reaction mixture a solution of 30 µL (0.203 mmol) of t-butyl bromo acetate in 500 µL of freshly distilled THF was added and the reaction was allowed to stir at room temperature under argon for 18 hours. To the reaction mixture 1 mL of water was added and the mixture was concentrated under reduced pressure. To the residue 20 mL of water was added and the pH of the reaction was adjusted to 6 with 5% phosphoric acid. To the reaction mixture 25 mL of CHCl$_3$ was added. The organic layer was separated and the aqueous layer was extracted with additional 4×25 mL of CHCl$_3$. All the organic extracts were combined, dried (Na$_2$SO$_4$) and concentrated. The residue was purified by flash column chromatography (silica gel) using 20:1 CHCl$_3$:MeOH as eluent to give 68 mg (0.093 mmol, 64%) of O$^c$-(carboxy-methyl-saquinavir (2AA) as a white solid. M+H 729

EXAMPLE 35

Synthesis of O$^c$-(succinimido-oxycarbonyl-methyl)-saquinavir (2BB)

The activated ester (2BB) is prepared from (2AA) by following the procedure described in Example 38.

Derivatization of Protease Inhibitors at Positions Other than the Central Hydroxyl

EXAMPLE 36

Synthesis of ethyl O$^{ar}$-carboxypropyl-nelfinavir (5H)

Nelfinavir (5) phenol (OH$^{ar}$) was selectively alkylated as follows: nelfinavir (62.5 mg) and sodium hydride (2.8 mg) were stirred 15 minutes in anhydrous DMF (1 mL) at room temperature. Ethyl 4-bromobutyrate (27.6 mg, Fluka Chemical Corp.) was added and the mixture was stirred 3 hours at room temperature. The mixture was evaporated to dryness under reduced pressure and directly purified by silica gel chromatography (3% methanol in chloroform elution) to yield ethyl O$^{ar}$-carboxypropyl-nelfinavir (5H) as a white solid (74.7 mg, 95%). M+H 682.4

EXAMPLE 37

Synthesis of O$^{ar}$-carboxypropyl-nelfinavir (5I)

Ethyl O$^{ar}$-carboxypropyl-nelfinavir (5H) from Example 31 (0.1440 g) and lithium hydroxide (0.0960 g) were stirred overnight in 50% aqueous THF (10 mL). The reaction mixture was allowed to settle (two layers), the organic layer separated and evaporated to dryness under reduced pressure. A sample was purified by preparative RP-HPLC (C18; 45% acetonitrile-water containing 0.1% trifluoroacetic acid) to give the analytical sample. The remainder was dried to yield O$^{ar}$-carboxypropyl-nelfinavir (5I) as a white solid, shown by $^1$H-NMR spectroscopy to be fairly clean material (0.1234 g, 89%) M+H 654.3

EXAMPLE 38

Synthesis of $O^{ar}$-(succinimido-oxycarbonyl-propyl)-nelfinavir (5J)

$O^{ar}$-carboxypropyl-nelfinavir (5I) from Example 37 (0.1210 g, 0.185 mmol), N-hydroxysuccinimide (0.0426 g, 0.37 mmol, 2 mol. equiv.; Aldrich Chemical Co.) and ethyl diethylaminopropyl carbodiimide hydrochloride (0.0710 g, 0.37 mmol, 2 mol. equiv.; Sigma Chemical Co) was stirred 2 hours in 10% anhydrous DMF-methylene chloride (9 mL). The mixture was evaporated to dryness under reduced pressure and purified by silica gel chromatography (3% methanol in chloroform elution) followed by preparative RP-HPLC (C18; 45% acetonitrile-water containing 0.1% trifluoroacetic acid) to yield $O^{ar}$-(succinimido-oxycarbonyl-propoxy)-nelfinavir (5J, 0.0681 g, 49%). M+H 751.3

Another reaction performed as above but using 5I (0.2764 g) followed by silica gel chromatography (3% methanol in chloroform elution) gave crude but fairly clean product (5J, 0.3526 g) as an oil.

EXAMPLE 39

Synthesis of $O^{ar}$-(succinimido-oxycarbonyl-propylamino-$^{co}$-glycyl-glycyl-propyl)-nelfinavir (5K)

$O^{ar}$-(succinimido-oxycarbonyl-propylamino-$^{co}$-glycyl-glycyl-propyl)-nelfinavir (5K) was prepared from $O^{ar}$-(succinimido-oxycarbonyl-propoxy)-nelfinavir (5J, 0.32 g) of Example 38 following the conditions of Example 41 (0.0657 g; 32%). M+H 950.4

EXAMPLE 40

Synthesis of N-(succinimido-oxycarbonyl-butyryl)-amprenavir (3G)

Amprenavir (3, 0.1517 g) and succinimido-oxycarbonyl butyryl chloride (0.0817 g) were stirred overnight in anhydrous DMF (3 mL) at 50° C. The mixture was evaporated to dryness under reduced pressure and directly purified by silica gel chromatography (15% THF in ethyl acetate elution) to yield N-(succinimido-oxycarbonyl-butyryl)-amprenavir (3G) as a white solid (0.1395 g, 61%). M+Na 739.2. Spectral data ($^1$H-NMR) was compatible with functionalization at the aniline nitrogen.

EXAMPLE 41

Synthesis of N-(succinimidyl-oxycarbonyl-propylamino-$^{co}$-glycyl-glycyl-glutaryl)-amprenavir (3H)

(a) N-(succinimido-oxycarbonyl-propionyl)-amprenavir (3G) from Example 40 (131.5 mg) and glycyl-glycyl-4-aminobutyric acid (43.4 mg, Bachem California Inc., Calif.) were stirred 7 hours in 25% aqueous borate (pH 10) in THF (5 mL). The mixture was evaporated to dryness under reduced pressure and directly purified by preparative RP-HPLC (C18; 45% acetonitrile-water containing 0.1% trifluoroacetic acid) to yield N-(3-carboxypropylamino-$^{co}$glycyl-glycyl-glutaryl)-amprenavir as a white solid (98.2 mg, 65%). M−H 817.4

(b) N-(4-carboxypropylamino-$^{co}$glycyl-glycyl-glutaryl)-amprenavir (40.9 mg), N-hydroxysuccinimide (11.5 mg), and ethyl dimethylaminopropyl carbodiimide (19.2 mg) were stirred 5 hours in 20% anhydrous DMF in methylene chloride (2.5 mL). The mixture was evaporated to dryness under reduced pressure and directly purified by silica gel chromatography (12% methanol in chloroform elution) to yield N-(succinimidyl-oxycarbonyl-propylamino-$^{co}$-glycyl-glycyl-glutaryl)-amprenavir (3H) as a white foam (37.9 mg, 83%). M+H 938.4

Urethane Derivatization of Protease Inhibitors

EXAMPLE 42

Synthesis of ethyl $O^c$-(carboxymethylaminocarbonyl)-saquinavir (2J)

Saquinavir methanesulfonate (2, 76.7 mg), ethyl isocyanatoacetate (23.0 mg, Aldrich Chemical Co.), and triethylamine (30 μL) were stirred 5 days in anhydrous DMF (1 mL) at 50° C. The mixture was evaporated to dryness under reduced pressure and directly purified by silica gel chromatography (5% methanol in chloroform elution) to yield ethyl $O^c$-(carboxymethylaminocarbonyl)-saquinavir (2J) as a white solid (32.3 mg, 40%). M+H 800.4

EXAMPLE 43

Synthesis of $O^c$-(carboxymethylaminocarbonyl)-saquinavir (2K)

Ethyl $O^c$-(carboxymethylaminocarbonyl)-saquinavir (2J) from Example 36 (0.1600 g) and lithium hydroxide (0.0960 g) were stirred 1 hour in 50% aqueous THF (10 mL). The organic layer was isolated, dried with anhydrous sodium sulfate, and evaporated to dryness under reduced pressure to yield $O^c$-(carboxymethylaminocarbonyl)-saquinavir (2K) as a white foam (0.1403 g, 91%). M+H 772.3.

EXAMPLE 44

Synthesis of $O^c$-(succinimido-oxycarbonyl-methylaminocarbonyl)-saquinavir (2L)

$O^c$-(carboxymethylaminocarbonyl)-saquinavir (2K) of Example 43 (0.1930 g), succinimidyl tetramethyluronium tetrafluoroborate (0.1882 g, Aldrich Chemical Co.) and diisopropylethylamine (0.15 mL) were stirred overnight in anhydrous THF (10 mL). HPLC-MS showed 80% complete reaction, produce peak (2L) M+H 869.3.

EXAMPLE 45

Synthesis of $O^c$-[(4-methoxycarbonylphenyl)-methylamino-$^{co}$-glycyl-carbonyl]-saquinavir (2W)

$O^c$-(carboxymethylaminocarbonyl)-saquinavir (2K) from Example 43 (0.1929 g) and succinimidyl tetramethyluronium tetrafluoroborate (0.1505 g) were stirred overnight in anhydrous tetrahydrofuran (10 mL) containing diisopropylethylamine (0.15 mL) to give (2L) in situ. Methyl-4-aminomethylbenzoate hydrochloride (0.1008 g, Aldrich Chemical Co.) and diisopropylethylamine (0.15 mL) were added and stirred 3 hours. The mixture was evaporated to dryness under reduced pressure and directly purified by silica gel preparative TLC (50% ethyl acetate and 2% methanol in chloroform) to yield 2W as a white solid (0.1905 g, 83%). M+H 919.4

EXAMPLE 46

Synthesis of $O^c$-[(4-carboxyphenyl-methylamino-$^{co}$glycyl-carbonyl]-saquinavir (2X)

$O^c$-[(4-methoxycarbonylphenyl)-methylamino-$^{co}$-glycyl-carbonyl]-saquinavir (2W) from Example 45 (0.232 g) was dissolved in methanol (10 mL). Lithium hydroxide (0.154 g) and water (2.5 mL) were added and the reaction was stirred overnight. The reaction mixture was extracted with methylene chloride, and the organic layer was dried with anhydrous sodium sulfate and evaporated to dryness under reduced pressure. The residue was purified by silica gel chromatography (10% methanol in chloroform containing 2% acetic acid) to yield 2X as a white solid (0.100 g, 44%). M+H 772.3

EXAMPLE 47

Synthesis of $O^c$-[4-(succinimido-oxycarbonyl-phenyl)-methylamino-$^{co}$-glycyl-carbonyl]-saquinavir (2Y)

$O^c$-[(4-succinimido-oxycarbonyl-phenyl)-methylamino-$^{co}$-glycyl-carbonyl]-saquinavir (2Y) was prepared from $O^c$-[(4-carboxyphenyl)-methylamino-$^{co}$-glycyl-carbonyl]-saquinavir (2X) from Example 46 (85 mg) following the conditions described in Example 38. M+H 1002.3

EXAMPLE 48

Synthesis of $O^c$-[4'-(succinimido-oxycarbonyl)-phenyl-aminocarbonyl]-saquinavir (2U)

50 mg (65.2 μmol) of saquinavir mesylate (2) in 5 mL freshly distilled DMF and 9 μL (65.2 μmol) triethylamine were stirred for about 10 minutes at ambient temperature until a clear solution was obtained 236.1 mg (1.3 mmol) 4-isocyanatobenzoyl chloride were added and the mixture turned red instantly. After standing at room temperature for 2 hours a 1 μL sample of the solution was injected into analytical HPLC (Vydac C18 column, 300 Å, 5 μm, 4.6×250 mm; eluent A: Millipore water/0.1% trifluoroacetic acid, eluent B: acetonitrile/0.1% trifluoroacetic acid; gradient of 0% B in A, rising to 60% B in A, over 60 minutes). The chromatography profile at 226 nm showed nearly complete derivatization of the educt ($t_r$=45.1 minutes) and formation of urethane ($t_r$=48.3 min.) together with some by-products.

22 mg of crude produce was isolated from the mixture by preparative HPLC (Vydac C18 column, 300 Å, 15-20 μm, 50×250 mm; eluent A: Millipore water/0.1% trifluoroacetic acid, eluent, B: 80% acetonitrile/0.1% trifluoroacetic acid; gradient of 0% B in A, rising to 70% B in A, over 140 minutes). The appropriate fractions eluting at about 62-65% B were pooled, lyophilized and subjected to a second chromatography step (modified gradient: gradient of 0% B in A, rising to 75% B in A, over 120 minutes). 10 mg (18%) of slightly red pure product were obtained from fractions 16 and 17. MALDI-TOF MS of purified carboxylic acid intermediate 2T. M+H 834, M+Na 856

10 mg (12 μmol) of $O^c$-(4-carboxyphenylaminocarbonyl)-saquinavir (2T) was dissolved in 500 μL freshly distilled DMF and 1.7 mg (15 μmol) N-hydroxysuccinimide (NHS) and 2.9 mg (15 μmol) ethyl-dimethylaminopropyl carbodiimide (EDC) were added. The solution was stirred 5 hours at room temperature under argon, then again 1.7 mg (15 μmol) NHS and 2.9 mg 15 EDC were added. The mixture was stirred further and allowed to react 2.5 days at room temperature. HPLC showed formation of NHS ester 2U, which was not isolated but used in situ for further reactions.

EXAMPLE 49

Synthesis of ethyl $O^c$-(carboxymethylaminocarbonyl)-$O^{ar}$-TBDMS-nelfinavir (5P)

$O^{ar}$-TBDMS-Nelfinavir (5A) of Example 5 (0.102 g), ethyl isocyanatoacetate (42 μL), and triethylamine (55 μL) were stirred 3.5 days in anhydrous DMF (2 mL) at 50° C. The mixture was evaporated to dryness under reduced pressure and purified first by silica gel chromatography (2% methanol in chloroform) followed by preparative RP-HPLC (C18) (60% acetonitrile-water containing 0.1% trifluoroacetic acid/30 minutes rising to 70% acetonitrile-water containing 0.1% trifluoroacetic acid over 30 minutes) to give recovered starting material 5A (0.0503 g; 43%) followed by the product 5P (0.0623 g; 45%) after lyophilization of the appropriate fractions. M+H 811.4

EXAMPLE 50

Synthesis of $O^c$-(carboxymethylaminocarbonyl)-nelfinavir (5Q)

Ethyl $O^c$-(carboxymethylaminocarbonyl)-$O^{ar}$-TBDMS-nelfinavir (5P) of Example 49 (56.5 mg) in 3.5 mL of 1:1 tetrahydrofuran-water was treated with 50 mg of lithium hydroxide monohydrate and the reaction stirred for 4 hours. The layers were allowed to settle, the organic layer isolated, dried with sodium sulfate and evaporated. The residue was largely redissolved in acetonitrile (5 mL), filtered and purified by preparative RP-HPLC (C18) (35% acetonitrile in water containing 0.1% trifluoroacetic acid) to give the $O^{ar}$-deprotected product 5Q (24.3 mg; 52%) M+H 669.2

EXAMPLE 51

Synthesis of $O^c$-[(3-carboxypropyl)amino-$^{co}$-glycyl-glycyl-glycyl-carbonyl)-nelfinavir (5R)

$O^c$-(carboxymethylaminocarbonyl)-nelfinavir (5Q) of Example 50 (20.4 mg), succinimidyl tetramethyluronium tetrafluoroborate (12.0 mg), and diisopropylethylamine (8 μL) were stirred overnight in anhydrous THF (1.5 mL) for 5.5 hours. LC/MS showed the presence of the corresponding NHS ester together with some starting material. Glycyl-glycyl-4-aminobutyric acid (7.0 mg) was added followed by 50 mM phosphate buffer (pH 10) until a clear solution was obtained. After stirring overnight the reaction was concentrated to ~1 mL, the milky residue diluted with acetonitrile and sonicated to give a clear solution which was purified by preparative RP-HPLC (C18) (30% acetonitrile in water for 30 minutes, 30% to 45% acetonitrile in water over 30 minutes, 45% to 90% acetonitrile in water over 30 minutes, all containing 0.1% trifluoroacetic acid) to give the product 5R from the main peak after lyophilization. (12.6 mg, 48%) M+H 868.4

EXAMPLE 52

Synthesis of $O^c$-(succinimido-oxycarbonyl-propyl-amino-$^{co}$-glycyl-glycyl-glycyl-carbonyl)-nelfinavir (5S)

$O^c$-(Succinimido-oxycarbonyl-propylamino-$^{co}$-glycyl-glycyl-carbonyl)-nelfinavir (5S) is synthesized from $O^c$-[(3-carboxypropyl)amino-$^{co}$-glycyl-glycyl-glycyl-carbonyl)-nelfinavir (5R) of Example 51 following the conditions of Example 41(b). M+H 964.4

Conjugation of Protease Inhibitors to Small Molecular Weight Labels

EXAMPLE 53

Synthesis of O$^c$-(fluoresceinyl-glycinamidyl-butyryl-aminocaproyl)-saquinavir (2V)

O$^c$-(succinimido-oxycarbonyl-butyryl-aminocaproyl)-saquinavir (2C) from Example 17 (10.0 mg) and fluoresceinyl glycinamide (5.0 mg, Molecular Probes, OR) is stirred overnight in 3% triethylamine-pyridine (0.1 mL). The mixture was evaporated to dryness under reduced pressure and directly purified by preparative RP-HPLC (C18; 50% acetonitrile-water containing 0.1% trifluoroacetic acid) to yield O$^c$-(fluoresceinyl-glycinamidyl-butyryl-aminocaproyl)-saquinavir (2V; 7.6 mg, 75%). M+H 1284.6

EXAMPLE 54

Synthesis of O$^c$-(fluoresceinyl-glycinamidyl-butyryl)-ritonavir (1I)

O$^c$-(fluoresceinyl-glycinamidyl-butyryl)-ritonavir (1I) was prepared from O$^c$-(succinimido-oxycarbonyl-butyryl)-ritonavir (1G) of Example 8 following the conditions described in Example 53 (8.4 mg; 69%). M+H 1221.4

EXAMPLE 55

Synthesis of O$^c$-[4'-(1-biotinyl-amino-3,6-dioxa-octylamino)-terephthaloyl-aminocaproyl]-indinavir (4I)

5.0 mg of O$^c$-[4'-(succinimido-oxycarbonyl)-benzoyl-aminocaproyl-indinavir (4F) from Example 22 were dissolved in 5.0 mL freshly distilled DMF. 13.6 mg of 1-biotinylamino-3,6-dioxa-octaneamine (biotin-DADOO, Roche Applied Science, Cat. No. 1112074-103) and 5.6 μL triethylamine were added, and the resulting clear solution was stirred under argon overnight. HPLC control showed complete reaction after 20 hours. DMF was removed on a rotavapor (high vacuum, much less than 1 Torr pressure, water bath 30° C.). The remaining oily produce was dissolved in 0.5 mL DMSO, filtered and injected into a preparative HPLC system (Vydac C18 column, 300 Å, 15-20 μm, 50×250 mm; eluent A: Millipore water/0.1% trifluoracetic acid, eluent B: 80% acetonitrile/0.1% trifluoracetic acid; gradient of 0% B in A rising to 70% B in A over 140 minutes), the appropriate fractions containing pure product were pooled and lyophilized. Structure was confirmed by MALDI-TOF-MS (M=1231). Yield 3.5 mg (2.84 μmol, 55% of theoretical yield)

EXAMPLE 56

Synthesis of O$^c$-[4'-(1-biotinyl-amino-3,6-dioxa-octylamino)-terephthaloyl-aminocaproyl]-amprenavir (3J)

An amprenavir-biotin conjugate (3J, O$^c$-[4'-(1-biotinyl-amino-3,6-dioxa-octylamino)-terephthaloyl-aminocaproyl]-amprenavir) was synthesized using the activated hapten O'-[4'-(succinimido-oxycarbonyl)-benzoyl-aminocaproyl-amprenavir (3D) from Example 20 in the procedure described in Example 55 above. Structure was confirmed by MALDI-TOF-MS (M=1123). Yield: 1.8 mg (1.60 μmol, 31% of theoretical yield)

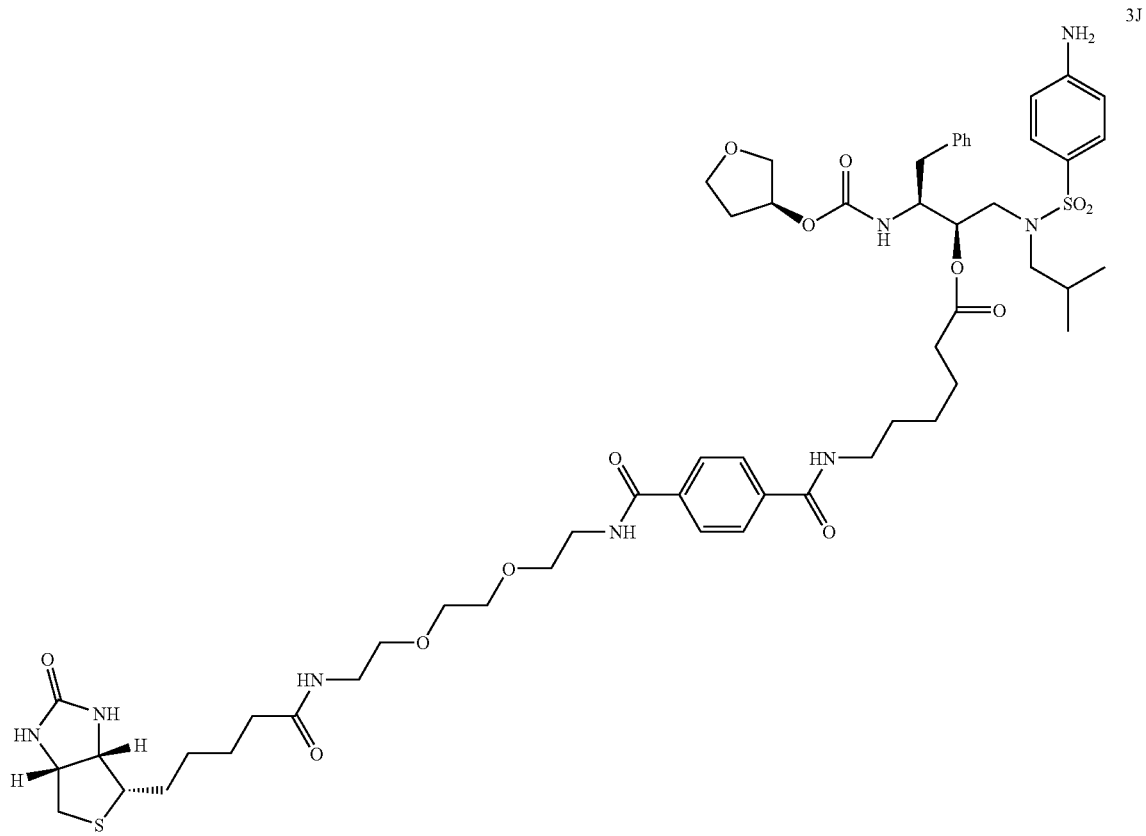

EXAMPLE 57

Synthesis of O$^c$-[4'-(1-biotinyl-amino-3,6-dioxa-octylamino)-terephthaloyl-aminocaproyl]-lopinavir (6G)

A lopinavir-biotin conjugate (6G, O$^c$-[4'-(1-biotinyl-amino-3,6-dioxa-octylamino)-terephthaloyl-aminocaproyl]-lopinavir) was synthesized using the activated hapten O$^c$-[4'-(succinimido-oxycarbonyl)-benzoyl-aminocaproyl]-lopinavir (6D) from Example 26 in the procedure described in Example 55 above. Structure was confirmed by MALDI-TOF-MS (M=1246). Yield: 0.6 mg (0.48 μmol, 10% of theoretical yield)

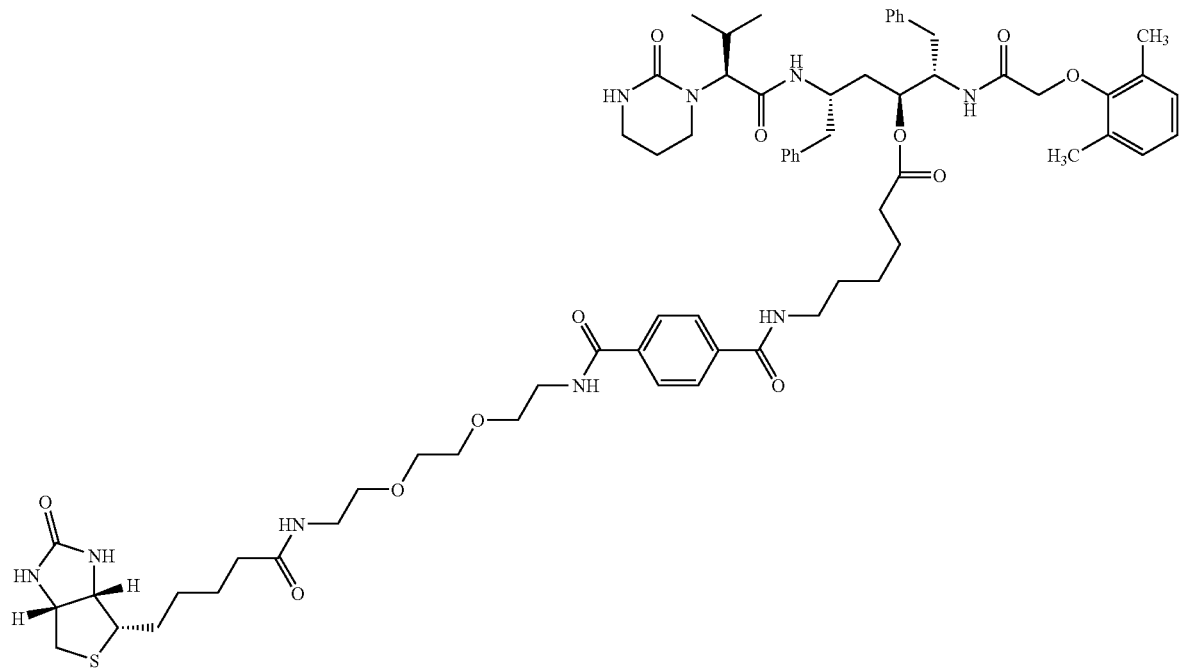

6G

EXAMPLE 58

Synthesis of O$^c$-[4'-(1-biotinyl-amino-3,6-dioxa-octylamino)-terephthaloyl-aminocaproyl]-ritonavir (1J)

A ritonavir-biotin conjugate (1J, O$^c$-[4'-(1-biotinyl-amino-3,6-dioxa-octylamino)-terephthaloyl-aminocaproyl]-ritonavir) was synthesized using the activated hapten O$^c$-[4'-(succinimido-oxycarbonyl)-benzoyl-aminocaproyl-ritonavir (1D) from Example 22 in the procedure described in Example 55 above. Structure was confirmed by MALDI-TOF-MS (M=1338). Yield: 5.4 mg (4.03 μmol, 87% of theoretical yield)

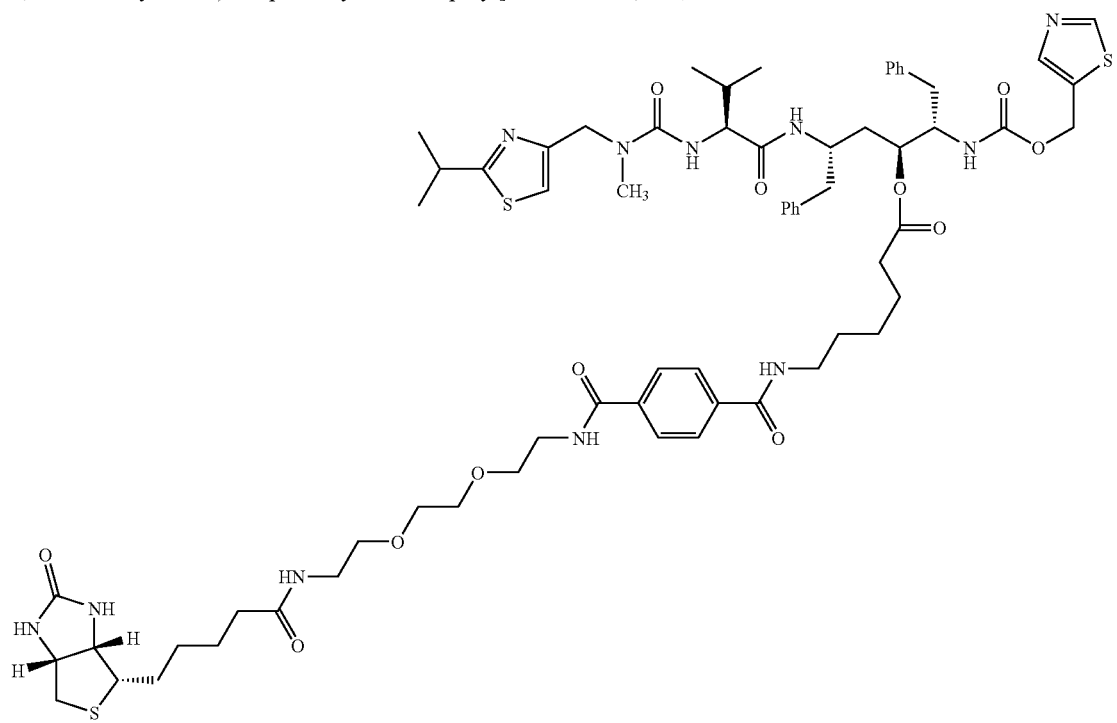

1J

Conjugation of Protease Inhibitors to Proteins

EXAMPLE 59

Synthesis of conjugate 2S of N-maleimidopropionyl-L-alanyl-L-(gamma-$O^c$-saquinavir)-glutamic acid with 2-IT modified bovine serum albumin Bovine serum albumin (30 mg) and 2-iminothiolane (2IT) hydrochloride (0.5 mg, Pierce Biotechnology Inc., IL) were allowed to stand 1 hour in the dark in 10 mM potassium phosphate, 0.1 M sodium chloride, 1 mM EDTA, pH 8.0 (3 mL). The mixture was desalted by gel filtration on a PD-10 column (Amersham-Pharmacia, NJ) eluting with 10 mM potassium phosphate, 0.1 M sodium chloride, 1 mM EDTA, pH 8.0. The appropriate fractions were collected, adjusted to pH 7.2, and N-maleimidopropionyl-L-alanyl-L-(gamma-$O^c$-saquinavir)-glutamic acid (2Q) from Example 29 (1 mg) dissolved in methanol (0.2 mL) was added. The mixture was allowed to stand 2 hours in the dark, quenched with ethyl maleimide (0.5 mg, Sigma Chemical Co.,), and desalted by gel filtration on a PD-10 column (10 mM potassium phosphate, 0.1 M sodium chloride, 1 mM EDTA, pH 8.0, elution). Protein quantification by Coomassie Blue protein assay (Bio-Rad Laboratories, Calif.; modified Bradford protein assay) showed quantitative recovery of protein at 4.3 mg/mL. UV difference spectroscopy showed the ratio of hapten to BSA to be 1:1.

EXAMPLE 60

Synthesis of conjugate 2R of N-maleimidopropionyl-L-glutamyl-(gamma-$O^c$-saquinavir)-L-alanine with SATP-modified KLH Keyhole limpet hemocyanin (CALBIOCHEM, CN Biosciences, San Diego, Calif.; slurry in 65% ammonium sulfate) was dialyzed exhaustively against 50 mM potassium phosphate buffer pH 7.5 (>8 buffer changes; dilution factor more than $10^{10}$) at room temperature (2-3 buffer changes) then at 4° C. The retentate was lyophilized almost to dryness, then reconstituted with an appropriate volume of 50 mM phosphate to give purified KLH at a relatively high concentration. Unused portions of the purified KLH were frozen and stored at −20° C. until needed.

Purified keyhole limpet hemocyanin (20 mg) and N-succinimidyl S-acetylthiopropionate (SATP, 10 mg, Pierce Biotechnology, Inc.) were allowed to stand 1 hour in 50 mM potassium phosphate, 1 mM EDTA, pH 7.5, and desalted by gel filtration on a PD-10 column (Amersham-Pharmacia) eluting with 50 mM potassium phosphate, 1 mM EDTA, pH 7.5. Derivatized protein (10 mg) was allowed to stand 2 hours in the dark in 50 mM potassium phosphate, 2.5 mM EDTA, 50 mM hydroxylamine hydrochloride, pH 7.5, and desalted by gel filtration (50 mM potassium phosphate, 5 mM EDTA, pH 7.2 elution). N-maleimidopropionyl-L-glutamyl-(gamma-$O^c$-saquinavir)-L-alanine (2P) from Example 28 (6 mg) dissolved in DMSO (1 mL) was added and the reaction was stirred 16 hours. Ethyl maleimide (0.5 mg) was added and the reaction was stirred 8 hours. The mixture was sequentially dialyzed against 30%, 20%, 10% and 0% DMSO in 50 mM potassium phosphate, pH 7.5 at room temperature, followed by dialysis against 50 mM potassium phosphate, pH 7.5 at 4° C. Protein quantification by Coomassie Blue showed quantitative recovery of protein at 1.6 mg/mL. UV difference spectroscopy showed up to 25% lysine substitution by hapten.

EXAMPLE 61

Synthesis of $O^c$-(succinimido-oxycarbonyl-butyryl-aminocaproyl)-saquinavir conjugate with BSA (2D)

Bovine serum albumin (30 mg) and $O^c$-(succinimido-oxycarbonyl-butyryl-aminocaproyl)-saquinavir (2C) from Example 17 (1 mg) were stirred 2 days in 30% DMSO in 50 mM potassium phosphate, pH 7.5 (1.5 mL), at room temperature. The mixture was sequentially dialyzed against 30%, 20%, 10% and 0% DMSO in 1 liter 50 mM potassium phosphate, pH 7.5, at room temperature, followed by dialysis against 1 liter 50 mM potassium phosphate, pH 7.5, at 4° C. Protein quantification by Coomassie Blue showed quantitative recovery of protein at 10.4 mg/mL. UV difference spectroscopy showed the ratio of hapten to BSA to be 1:1.

EXAMPLE 62

Synthesis of $O^c$-[(4'-succinimido-oxycarbonyl)-benzoyl-aminocaproyl]-saquinavir conjugate with BSA (2G)

$O^c$-[(4'-succinimido-oxycarbonyl)-benzoyl-aminocaproyl]-saquinavir BSA conjugate was prepared from bovine serum albumin (30 mg) and $O^c$-[(4'-succinimido-oxycarbonyl)-benzoyl-aminocaproyl]-saquinavir (2F) from Example 18 (1 mg) following the conditions described in Example 61. Protein quantification by Coomassie Blue showed quantitative recovery of protein at 10.4 mg/mL. UV difference spectroscopy showed the ratio of hapten to BSA to be 1:1.

EXAMPLE 63

Synthesis of $O^c$-(succinimido-oxycarbonyl-butyryl-aminocaproyl)-saquinavir conjugate with KLH (2E)

$O^c$-(succinimido-oxycarbonyl-butyryl-aminocaproyl)-saquinavir KLH conjugate was prepared from purified keyhole limpet hemocyanin (30 mg) and $O^c$(succinimido-oxycarbonyl-butyryl-aminocaproyl)-saquinavir (2C) from Example 17 (10 mg) following the general conditions described in Example 61. Protein quantification by Coomassie Blue showed quantitative recovery at protein at 10.9 mg/mL. Amine quantification by trinitrobenzenesulfonic acid (TNBS, Sigma Chemical Co.) colorimetric assay showed 60% lysine modification.

EXAMPLE 64

Synthesis of $O^c$-(succinimido-oxycarbonyl-butyryl-aminocaproyl)-ritonavir conjugate with LPH (1E)

$O^c$-(succinimido-oxycarbonyl-butyryl-aminocaproyl)-ritonavir LPH conjugate was prepared from horseshoe crab hemocyanin (LPH, 30 mg; Sigma Chemical Co.) and $O^c$-(succinimido-oxycarbonyl-butyryl-aminocaproyl)-ritonavir (1C) from Example 15 (7 mg) following the general conditions described in Example 61. Protein quantification by Coomassie Blue showed quantitative recovery of protein at 7.9 mg/mL. Amine quantification by TNBS colorimetric assay showed 26% lysine modification.

EXAMPLE 65

Synthesis of $O^c$-[4'-(succinimido-oxycarbonyl)-benzoyl-aminocaproyl]-ritonavir conjugate with BSA (1F)

$O^c$-[4'-(succinimido-oxycarbonyl)-benzoyl-aminocaproyl]-ritonavir BSA conjugate was prepared from bovine serum albumin (30 mg) and $O^c$-[4'-(succinimido-oxycarbonyl)-benzoyl-aminocaproyl]-ritonavir (1D) from Example 16 (1 mg) following the general conditions described in Example 61. Protein quantification by Coomassie Blue showed quantitative recovery of protein at 10.3 mg/mL. TNBS colorimetric assay showed the ratio of hapten to BSA to be 2:1.

EXAMPLE 66

Synthesis of $O^c$-(succinimido-oxycarbonyl-butyryl)-ritonavir conjugate with KLH (1H)

$O^c$-(succinimido-oxycarbonyl-butyryl)-ritonavir KLH conjugate was prepared from purified keyhole limpet hemocyanin (30 mg) and $O^c$-(succinimido-oxycarbonyl-butyryl)-ritonavir (1G) from Example 8 (10 mg) following the general conditions described in Example 61. Protein quantification by Coomassie Blue showed quantitative recovery of protein at 11.9 mg/mL. Amine quantification by TNBS colorimetric assay showed 60% lysine modification.

EXAMPLE 67

Synthesis of $O^c$-(succinimido-oxycarbonyl-butyryl-aminocaproyl)-amprenavir conjugate with KLH (3E)

$O^c$-(succinimido-oxycarbonyl-butyryl-aminocaproyl)-amprenavir KLH conjugate was prepared from purified keyhole limpet hemocyanin (30 mg) and $O^c$-(succinimido-oxycarbonyl-butyryl-aminocaproyl)-amprenavir (3C) from Example 19 (8 mg) following the general conditions described in Example 61. Protein quantification by Coomassie Blue showed quantitative recovery of protein at 6.8 mg/mL. Amine quantification by TNBS colorimetric assay showed 20% lysine modification.

EXAMPLE 68

Synthesis of $O^c$-[(succinimido-oxycarbonyl)-butyryl-aminocaproyl]-indinavir conjugate with KLH (4G)

$O^c$[-(4'-succinimido-oxycarbonyl-butyryl)-aminocaproyl]-indinavir KLH conjugate was prepared from purified keyhole limpet hemocyanin (30 mg) and $O^c$-[(-succinimido-oxycarbonyl-butyryl)-aminocaproyl]-indinavir (4E) from Example 21 (9 mg) following the general conditions described in Example 61. Protein quantification by Coomassie Blue showed quantitative recovery of protein at 7.4 mg/mL. Amine quantification by TNBS colorimetric assay showed 20% lysine modification.

EXAMPLE 69

Synthesis of $O^c$-[4'-(succinimido-oxycarbonyl)-benzoyl-aminocaproyl]-amprenavir conjugate with BSA (3F)

$O^c$-[4'-(succinimido-oxycarbonyl)-benzoyl-aminocaproyl]-amprenavir BSA conjugate was prepared from bovine serum albumin (30 mg) and $O^c$-[(4'-succinimido-oxycarbonyl)-benzoyl-aminocaproyl]-amprenavir (3D) from Example 20 (1 mg) following the general conditions described in Example 61. Protein quantification by Coomassie Blue showed quantitative recovery of protein at 11.5 mg/mL. UV difference spectroscopy showed the ratio of hapten to BSA to be 2:1.

EXAMPLE 70

Synthesis of $O^c$-[4'-(succinimido-oxycarbonyl-benzoyl)-aminocaproyl]-indinavir conjugate with BSA (4H)

$O^c$-[4'-(succinimido-oxycarbonyl)-benzoyl-aminocaproyl]-indinavir BSA conjugate was prepared from bovine serum albumin (30 mg) and $O^c$-[4'-(succinimido-oxycarbonyl-benzoyl)-aminocaproyl]-indinavir (4F) from Example 22 (1 mg) following the general conditions described in Example 61. Protein quantification by Coomassie Blue showed quantitative recovery of protein at 10.8 mg/mL. UV difference spectroscopy showed the ratio of hapten to BSA to be 2:1.

EXAMPLE 71

Synthesis of $O^c$-(succinimido-oxycarbonyl-butyryl-aminocaproyl)-nelfinavir conjugate with KLH (5F)

$O^c$-[(succinimido-oxycarbonyl-butyryl-aminocaproyl)-nelfinavir KLH conjugate was prepared from purified keyhole limpet hemocyanin (30 mg) and $O^c$-[(succinimido-oxycarbonyl-butyryl-aminocaproyl)-nelfinavir (5D) from Example 23 (9 mg) following the general conditions described in Example 61. Protein quantification by Coomassie Blue showed quantitative recovery of protein at 9.7 mg/mL. Amine quantification by TNBS colorimetric assay showed 36% lysine modification.

EXAMPLE 72

Synthesis of $O^c$-[4'-(succinimido-oxycarbonyl)-benzoyl-aminocaproyl]-nelfinavir conjugate with BSA (5G)

$O^c$-[4'-(succinimido-oxycarbonyl)-benzoyl-aminocaproyl]-nelfinavir BSA conjugate was prepared from bovine serum albumin (30 mg) and $O^c$-[(4'-succinimido-oxycarbonyl)-benzoyl-aminocaproyl]-nelfinavir (5E) from Example 24 (1 mg) following the general conditions described in Example 61. Protein quantification by Coomassie Blue showed quantitative recovery of protein at 10.9 mg/mL. UV difference spectroscopy showed the ratio of hapten to BSA to be 2:1.

EXAMPLE 73

Synthesis of $O^{ar}$-(succinimido-oxycarbonyl-propylamino-$^{co}$-glycyl-glycyl-propoxy)-nelfinavir conjugate with KLH (5L)

$O^{ar}$-(succinimido-oxycarbonyl-propylamine-$^{co}$-glycyl-glycyl-propoxy)-nelfinavir KLH conjugate was prepared from keyhole limpet hemocyanin (30 mg) and $O^{ar}$-(succinimido-oxycarbonyl-propylamino-$^{co}$-glycyl-glycyl-propoxy)-nelfinavir (5K, 10 mg) of Example 39 following the general conditions described in Example 61. Protein quantification by Coomassie Blue showed quantitative recovery of protein at 14.6 mg/mL. Amine quantification by TNBS colorimetric assay showed 57% lysine modification.

EXAMPLE 74

Synthesis of $O^c$-(succinimido-oxycarbonyl-butyryl-aminocaproyl)-lopinavir conjugate with KLH (6F)

$O^c$-(succinimido-oxycarbonyl-butyryl-aminocaproyl)-lopinavir KLH conjugate was prepared from keyhole limpet hemocyanin (40 mg) and $O^c$-(succinimido-oxycarbonyl-butyryl-aminocaproyl)-lopinavir (6C) from Example 25 (16 mg) in 40% dimethyl sulfoxide in 50 mM potassium phosphate, pH 7.5 (3.4 mL), in a similar manner to Example 61, followed by sequential dialysis against 40%, 30%, 20%, 10% and 0% DMSO in 50 mM potassium phosphate, pH 7.5 at room temperature, followed by dialysis against 50 mM potassium phosphate, pH 7.5 at 4° C. Protein quantification by Coomassie Blue showed quantitative recovery of protein at 6.9 mg/mL. Amine quantification showed 38% lysine modification.

EXAMPLE 75

Synthesis of $O^c$-[4'-(succinimido-oxycarbonyl)-benzoyl-aminocaproyl]-lopinavir conjugate with BSA (6E)

$O^c$-[4'-(succinimido-oxycarbonyl)-benzoyl-aminocaproyl]-lopinavir BSA conjugate was prepared from bovine serum albumin (93 mg) and $O^c$-[4'-(succinimido-oxycarbonyl)-benzoyl-aminocaproyl]-lopinavir (6D) from Example 26 (3 mg) following the general conditions described in Example 61. Protein quantification by Coomassie Blue showed quantitative recovery of protein at 11.1 mg/mL. UV difference spectroscopy showed the ratio of hapten to BSA to be 2:1.

EXAMPLE 76

Synthesis of N-(succinimido-oxycarbonyl-propylamino-$^{co}$-glycyl-glycyl-glutaryl)-amprenavir conjugate with KLH (3I)

N-(succinimidyl-oxycarbonyl-propylamino-$^{co}$-glycyl-glycyl-glutaryl)-amprenavir KLH conjugate was prepared from purified keyhole limpet hemocyanin (30 mg) and N-(succinimidyl-oxycarbonyl-propylamino-$^{co}$-glycyl-glycyl-glutaryl)-amprenavir (3H) from Example 41 (9 mg) following the general conditions described in Example 61. Protein quantification by Coomassie Blue showed quantitative recovery of protein at 8.7 mg/mL. Amine quantification by TNBS colorimetric assay showed 40% lysine modification.

Development of Antibodies to Protease Inhibitors

EXAMPLE 77

Antibody Response to Saquinavir KLH Immunogen

Saquinavir-KLH (2E) was used to immunize mice of both the C57 Black and Swiss Webster strains. The doses and routes of immunization were the same for both strains of mice. The immunization schedule is given in Table 1.

TABLE 1

Immunization Schedule.

| Date | Dose/Route | Adjuvant |
| --- | --- | --- |
| Day 0 | 75 µg FP & IP | Complete Freund's |
| Day 25 | 100 µg FP & IP | Incomplete Freund's |
| Day 53 | 100 µg IP | Incomplete Freund's |

FP = Foot pad;
IP = Intraperitoneal

Blood samples were taken from each mouse by retro-orbital bleeds thirteen days after the last immunization. The blood was immediately centrifuged and the serum drawn off and stored in a micro-vial after being diluted 10 times with phosphate buffered saline with 0.02% thimerosal preservative.

The next day an ELISA was conducted to establish the titers of antibody present. The ELISA consisted of microtiter plates coated with different saquinavir-BSA conjugates, all at 1 µg/mL in biocarbonate buffer (0.1 M, pH 9.6, 100 µL/well, 4° C. overnight). After coating the plates were emptied and 200 µL of post coat solution consisting of Tris buffer, 1% gelatin hydrolysate, 2% sucrose and 0.17% TWEEN-20 emulsifying agent (ICI Americas, Inc.) was added. This was incubated at 37° C. for 1 hour to block any uncoated regions of the wells. The sera were tested by carrying out a pre-dilution to 1000, then serial dilutions down each column at a 1:3 ratio. The volume of diluted serum in each well was 100 µl, which was allowed to incubate at 37° C. in a humidified container for 1 hour and 20 minutes. The plates were then washed with phosphate buffered saline, and 100 µL of goat anti-mouse IgG-HRP (horseradish peroxidase) conjugate (Zymed, Inc., diluted 1:5000 in PBS) was added to each well. The plates were again incubated for 2 hours under the same conditions, then washed again. Development consisted of addition of 100 µL of K-BLUE SUBSTRATE (Neogen Corporation) to each well, and incubation at room temperature in the dark for 30 minutes. Development was stopped by the addition of 100 µL of 1N HCl to each well. The optical densities of each plate were read with a microplate reader at 450 nm and captured to a computer.

Figure 15:
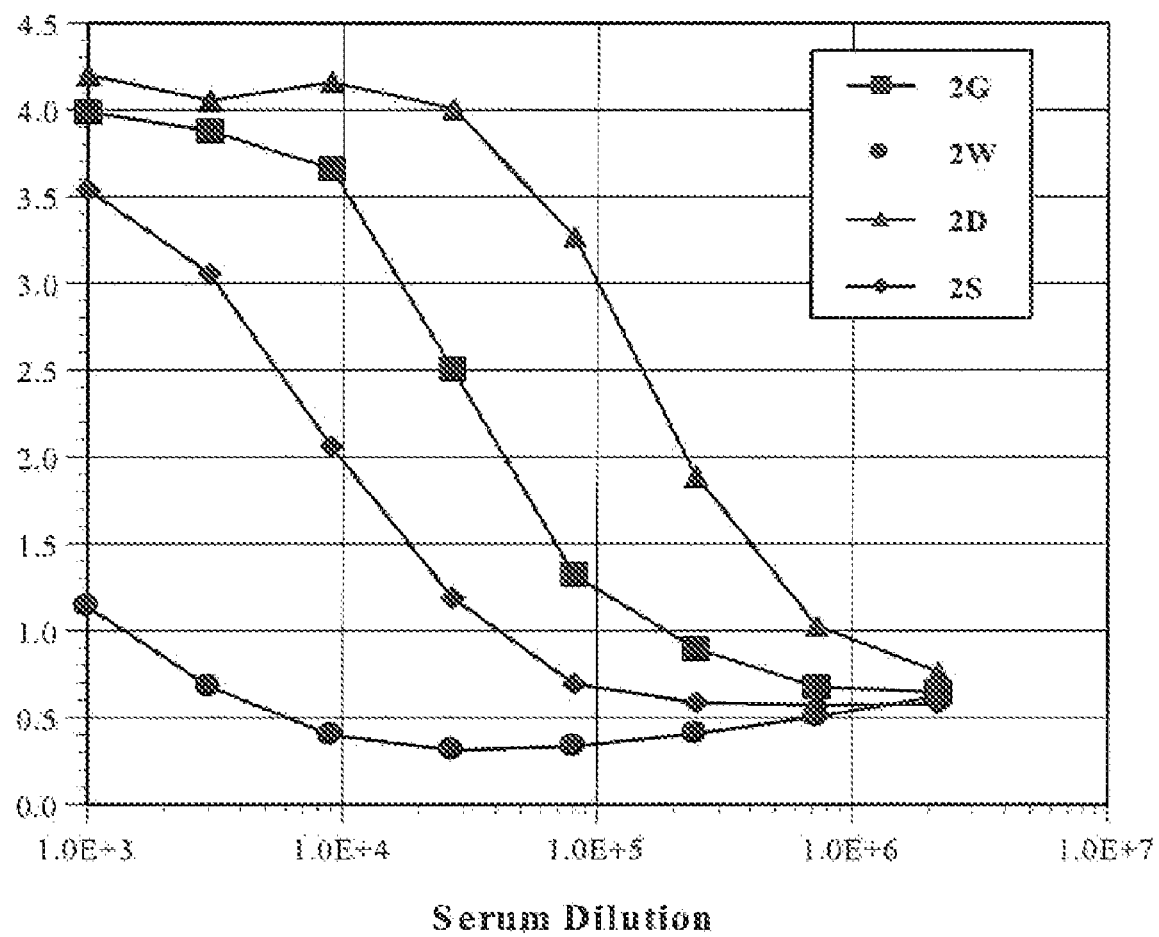
FIG. 15 is a chart showing antibody titers generated in Example 77 using conjugates 2G, 2W, 2D and 2S.
Figure 16:
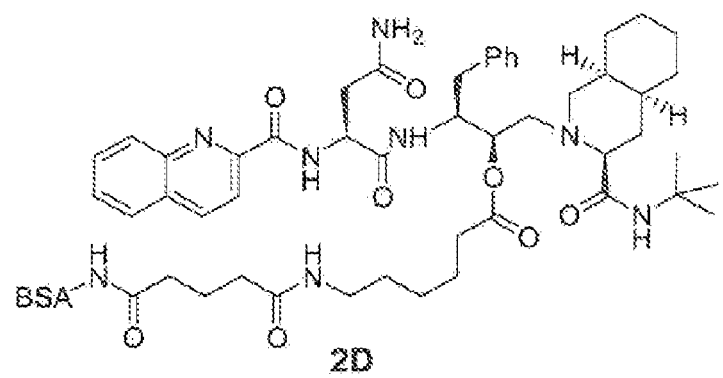
FIG. 16 illustrates the structures of the conjugates used in Example 77.
Figure 16:
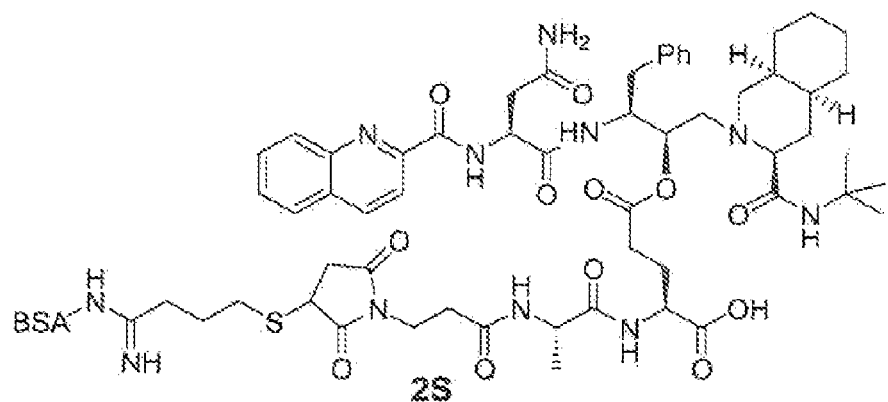
Figure 16:
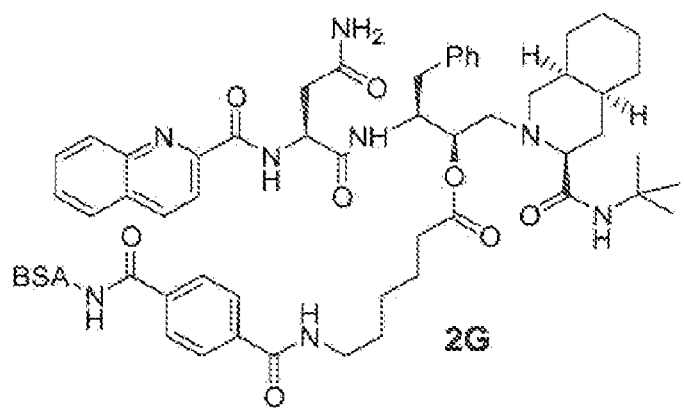
Figure 16:
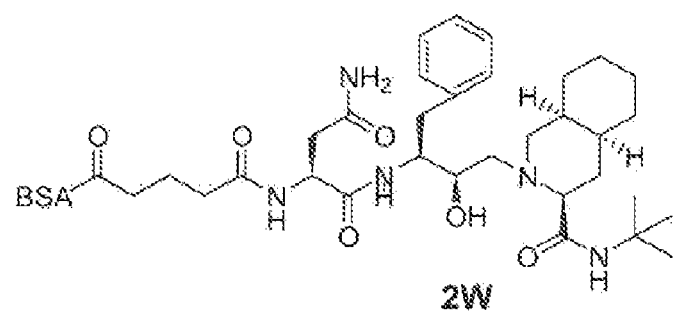

The serum titers when examined with respect to saquinavir-BSA conjugate 2D with the same linker structure and position as the immunogen were substantially higher than for the other conjugates, indicating there was some linker recognition in the polyclonal antibody population. As illustrated in FIG. 15, titers decreased as the structure and position of the linker differed from the immunogen. FIG. 15 is a graph of titers of mouse #333 serum using saquinavir conjugates 2G, 2W, 2D and 2S. (Note: Preparation of conjugate 2W is described in previously cited copending application EP 1 207 394 A2 as Example V.) The optical density of 450 nm read at 30 minutes is plotted on the Y-axis and serum dilutions are plotted on the X-axis.

From these analyses, it was clear that the saquinavir-KLH conjugate was suitable for use in raising polyclonal antibodies and could also therefore by used for the development of monoclonal antibodies.

EXAMPLE 78

Development of Monoclonal Antibodies to Saquinavir

Female Swiss-Webster mice, at least 3 months of age, were used for immunizations. The KLH immunogen 2E was emulsified in 50% Complete Freund's Adjuvant, 50% saline, at a final concentration of 0.75 mg/ml. Each mouse was injected twice with 10 μL subcutaneously in the rear thigh region, and with 90 μl in the peritoneal space. Twenty five days later, similar injections were given in the same routes, using Freund's Incomplete Adjuvant and a concentration of 1 mg/ml, total volume per mouse was 0.1 ml. Thirteen days later each mouse was bled retro-orbitally to obtain a serum sample for analysis. A third immunization was administered 49 days later, identical to the second formulation. The mouse selected for use in fusion was given a booster immunization thirteen days later identical to that of the second and third injections. Four days later, the mouse was used for cell fusion to develop monoclonal antibody secreting hybridomas.

The conjugate 2D featuring the linker homologous to the immunogen showed the greatest efficacy of binding of serum antibodies. The binding was directly related to the degree of homology of the conjugate linker to that of the immunogen. Efficacy of binding was found to be, from the strongest to the weakest, 2D>2G>2S>2W. Based on the observations made in analyzing the serum antibodies above, it was decided to devise a strategy for screening of monoclonal antibodies in the fusion phase of the work in which the effect of linker homology could be distinguished and only those clones showing little or no linker preference would be selected.

The strategy featured two tactics. First, antibody binding would be tested using a linker shown by the above analysis to provide less than maximal binding of the sera antibodies. Second, a second well coated with the same conjugate, in which 400 ng/mL of free drug was included, would be employed to estimate the competitive effect of the drug on binding. The result would allow the selection of only those monoclonals which competitively bound the free drug (i.e., without any linker attached).

The mouse selected for fusion was killed via exsanguination. The popliteal, inguinal, suclavial and deep inguinal lymph nodes and spleen were harvested and pooled. The tissues were ground between two sterile glass slides to release the lymphocytes. One-half of the resulting lymphocyte suspension was used to fuse with the F0 myeloma cell line (ATCC CRL 1646), the remaining half was fused with the P3 myeloma (both myelomas were from ATCC).

Fusion consisted with adding myeloma cells (⅕ the number of lymphocytes) to the lymphocytes, washing via centrifugation, resuspension in serum-free warm Iscove's modified Dulbecco's media (IMDM), and re-centrifugation. The centrifuge tubes containing the resulting pellets were gently tapped to loosen the cells, then 1 mL of warmed PEG/DMSO solution (Sigma Chemicals) was slowly added with gentle mixing. The cells were kept warm for 1.5 minutes, after which pre-warmed serum-free IMDM was added at the following rates: 1 ml/min, 2 ml/min, 4 ml/min, 10 ml/min, then the tube was filled to 50 ml, sealed and incubated for 15 minutes. The cell suspensions were centrifuged, the supernatant decanted, and IMDM containing 10% fetal calf serum was added. The cells were centrifuged once again, and resuspended in complete cloning medium. This consisted of IMDM, 10% FCS, 10 % Condimed H1 (Roche Molecular Systems), 4 mM Glutamine, 50 μM 2-mercaptoethanol, 40 μM ethanolamine, pen/strep antibiotics. The cells were suspended at a density of $4\times10^5$ lymphocytes/ml, distributed 100 μL/well into sterile 96-well sterile microculture plates and incubated at 37° C., in 5% $CO_2$ for 24 hours. The next day, 100 μL of hypoxanthine-methotrexate-thymidine (HMT) selective medium (cloning medium+1:25 HMT supplement from Sigma Chemicals) was added. On the $6^{th}$ day of incubation, approximately 150 μL of media was drawn from each well using a sterile 8-place manifold connected to a light vacuum source. One hundred fifty microliters of hypoxanthine-thymidine (HT) media was then added. This consists of cloning medium+1:50 HT supplement (Sigma Chemicals). The plates were returned to the incubator and inspected daily for signs of growth. When growth was judged sufficient, wells were screened for antibody production via ELISA.

Microplates were coated with 100 μL saquinavir-BSA conjugate at 1 μg/mL in 0.1 M carbonate buffer, pH 9.5 for 1 hour at 37° C. (humidified). The plates were then emptied and filled with a post-coat solution. The plates were incubated for an additional 1 hour at 37° C. (humidified) after which they were washed with phosphate-buffered saline containing 0.1% TWEEN 20. The plates were then filled with a 2% sucrose solution in 0.15 M Tris, pH 7.2-7.4 briefly, then emptied and allowed to air dry at room temperature. When dried, the plates were packed in zip-lock bags containing several desiccant pillows, sealed and stored at 4° C. until use.

When the growing clones were judged ready for testing, 25 μL of supernatant from the wells were taken and transferred to 96-well flexible plates. Culture medium was added to each well to provide a 1:10 dilution of the media sample. Two saquinavir-BSA coated wells were used for each culture well tested. One well received 50 μL of PBS buffer, the other received 50 μL of PBS containing saquinavir drug at a concentration of 800 ng/ml. Fifty microliters of the diluted sample were transferred to each of two of the coated wells above. The plates were incubated covered for 1 hour at 37° C., then washed with PBS-TWEEN. The wells were then filled with 100 μL of goat anti-mouse IgG-HRP conjugate (Zymed Labs) diluted 1:5,000 in PBS-TWEEN and the plate re-incubated for 1 hour. The plates were then washed again, and 100 μL of K-BLUE SUBSTRATE (Neogen Corp) were added to each well. This was allowed to develop for 5-15 minutes, the reaction being stopped by the addition of 100 μL of 1 N HCl. Color was read via a microplate reader at 450 nm and collected by computer for analysis. Criteria for selection were binding to the saquinavir-BSA conjugate and significant inhibition of binding in the second well due to the free drug.

TABLE 2

Representative portion of the screening of the plates

| Culture well | OD in absence of free drug | OD in presence of free drug |
| --- | --- | --- |
| 1 H12 | 3.568 | 0.504 |
| 37F5 | 0.738 | 0.358 |
| 2B11 | 3.942 | 3.649 |
| 19D5 | 1.152 | 0.225 |
| 24D11 | 3.305 | 1.342 |

Subsequent to the selection of a clone from the fusion culture plates, the cells were subjected to stringent cloning via limiting dilution. Subclones growing from those wells in which single cells had been verified by microscopy were then re-tested by the above method. Stability of antibody expression was judged on the number of wells showing antibody, the level of binding and the presence of any wells showing growth but little or no antibody. If any of the latter were found, a well showing high antibody secretion was then used to repeat stringent subcloning. This was repeated as necessary to obtain 100% of the subclones secreting equivalent quantities of antibody. Cells from selected wells were then expanded in culture, and used to prepare preliminary cell banks. The supernatant from those cultures was then subjected to specificity analysis.

The antibody containing culture supernatants from the expansion cultures were subjected to specificity analysis by the following procedure. First, the titer appropriate for analysis was determined by dilution analysis. A dilution of antibody providing for approximately 50% of maximal binding was selected for proceeding to the next step. Second, binding to the saquinavir-BSA conjugate was examined at the above antibody dilution, in the presence of varying amounts of six HIV protease inhibitor drugs. The data was subjected to analysis by non-linear regression curve fitting to a 4-parameter logistic function. That parameter which describes the concentration of the free drug which corresponds to 50% of the binding in the absence of free drug is termed the $ED_{50}$ for that drug. The specificity of the antibody can thus be described by comparing the $ED_{50}$ of the cognate drug, saquinavir, or saq $ED_{50}$ with the other values for other drugs fitted from those data according to the following equation (using nelfinavir data for this example):

$$\% \text{ cross-reactivity} = \frac{saqED_{50}}{nelED_{50}} \times 100.$$

The four parameter logistic function used is $$ODx = \frac{ODmax}{\left(1 + \left(\frac{ED_{50}}{X}\right)^S\right)} - OD$$

min where S is the curvature parameter, ODmax is the optical density with 0 drug concentration, ODmin is the optical density of the background of the instrument, and ODx is the optical density observed at drug concentration X in moles/liter (M/l).

By this analysis, the cross-reactivities of two anti-saquinavir antibodies are given in Table 3. Murine hybridomas SAQ 10.2.1 and SAQ 14.1.1 were deposited with the American Type Culture Collection (ATCC) on Jan. 18, 2002 and assigned ATCC No. PTA-3973 and ATCC No. PTA-3974, respectively.

EXAMPLE 79

Development of Monoclonal Antibodies to Nelfinavir

The procedures used for the development of monoclonals to nelfinavir were similar to those used for saquinavir. Female Balb/c mice 8 weeks of age, were immunized with 100 μg of conjugate 5F emulsified in Complete Freund's Adjuvant via intraperitoneal injection. Twenty one days later, another immunization of the same dose followed in Incomplete Freund's adjuvant. Four further injections were carried out, using the same dosage and alternating with Ribi adjuvant, at approximately 21 day intervals. All adjuvants were from the Sigma Chemical Co.

Four days following the last injection, a mouse was killed by exsanguination and cervical dislocation. Spleen cells were taken and fused to the F0 myeloma line by the same procedure as for saquinavir. Culturing and feeding were also the same.

Screening of growing hybridomas was as for saquinavir, with the exception that nelfinavir-BSA (5G) and free nelfinavir were substituted for the saquinavir-BSA and free saquinavir, respectively. Table 4 presents a portion of the screening data thus obtained.

TABLE 4

| Culture well | Development of nelfinavir clones | |
|---|---|---|
| | OD w/o free nelfinavir | OD with free nelfinavir |
| 9 D4 | 4.200 | 1.812 |
| 56 A9 | 3.906 | 0.469 |
| 12 G3 | 3.948 | 2.482 |
| 46 B12 | 3.946 | 1.869 |
| 12 A6 | 3.955 | 0.456 |
| 40 E7 | 3.820 | 0.271 |

Further processing to assure stability was by the same methods as for saquinavir monoclonal antibodies. Specificity analysis was using the same panel of drugs, with competitive binding by nelfinavir taken as 100%. Table 5 shows the specificities of subclones of the lines shown in Table 4.

TABLE 3

| | | Specificity of saquinavir 10.2.1 and 14.1.1 antibodies | | | | | |
|---|---|---|---|---|---|---|---|
| Clone | | Saquinavir | Nelfinavir | Indinavir | Amprenavir | Ritonavir | Lopinavir |
| 14.1.1 | % Cross Rx | 100 | 0.003 | 0.100 | 0.053 | 0.134 | 0.075 |
| | $ED_{50}$ (M/l) | $4.9 \times 10^{-8}$ | $1.72 \times 10^{-3}$ | $4.9 \times 10^{-5}$ | $9.35 \times 10^{-5}$ | $3.66\ 10^{-5}$ | $6.52\ 10^{-5}$ |
| 10.2.1 | % Cross Rx | 100 | 0 | 0 | 0 | 0 | 0 |
| | $ED_{50}$ (M/l) | $1.7E^{-8}$ | $<1E^{-4}$ | $<1E^{-4}$ | $<1E^{-4}$ | $<1E^{-4}$ | $<1E^{-4}$ |

TABLE 5

Specificities of selected stabilized subclones of nelfinavir clones

| Clone | | Saquinavir | Nelfinavir | Indinavir | Amprenavir | Ritonavir | Lopinavir |
|---|---|---|---|---|---|---|---|
| 5.4.1 | % Cross Rx | 0 | 100 | 0 | 0 | 0 | 0 |
| | $ED_{50}$ (M/l) | $>4 \times 10^{-4}$ | $1.1 \times 10^{-9}$ | $>4 \times 10^{-4}$ | $>4 \times 10^{-4}$ | $>4 \times 10^{-4}$ | $>4 \times 10^{-4}$ |
| 15.3.1 | % Cross Rx | 0 | 100 | 0 | 0 | 0 | 0 |
| | $ED_{50}$ (M/l) | $>4 \times 10^{-4}$ | $2.4 \times 10^{-8}$ | $>4 \times 10^{-4}$ | $>4 \times 10^{-4}$ | $>4 \times 10^{-4}$ | $>4 \times 10^{-4}$ |
| 21.4 | % Cross Rx | 0.041 | 100 | 0.033 | 0.018 | 0 | 0.07 |
| | $ED_{50}$ (M/l) | $1.3 \times 10^{-6}$ | $5.3 \times 10^{-10}$ | $1.6 \times 10^{-6}$ | $2.9 \times 10^{-6}$ | $>4 \times 10^{-4}$ | $7.7 \times 10^{-8}$ |

Murine hybridoma NEL 5.4.1 was deposited with the American Type Culture Collection (ATCC) on Jun. 25, 2002 and assigned ATCC No. PTA-4475.

EXAMPLE 80

Development of Monoclonal Antibodies to Indinavir 12-week old female Balb/c mice were given a primary intraperitoneal immunization with 100 µg indinavir KLH conjugate 4G together with the adjuvant CFA (complete Freund's adjuvant). This was followed by three further intraperitoneal immunizations after 6 weeks at monthly intervals. In this case each mouse was administered with 100 µg indinavir KLH conjugate 4G together with IFA (incomplete Freund'adjuvant). Subsequently the last immunizations were carried out intravenously with 100 µg indinavir KLH conjugate 4G in PBS buffer on the second day and on the last day before fusion.

The spleen cells of the mice immunized as described above were fused with myeloma cells according to Galfre, Methods in Enzymology, Vol. 73, 3 (1981). Approximately $1 \times 10^8$ spleen cells of the immunized mouse were mixed with $2 \times 10^7$ myeloma cells (P3X63-Ag8-653, ATCC CRL 1580) and centrifuged (10 minutes at 300 G and room temperature). The cells were then washed once with RPMI 1640 medium without fetal calf serum (FCS) and again centrifuged at 400 G in a 50 mL conical tube. Subsequently 1 mL PEG (polyethylene glycol, molecular weight 4000, Merck, Darmstadt) was added, and it was mixed by gentle shaking. After 1 minute in a water bath at 37° C., 5 mL RPMI 1640 without FCS were added dropwise, mixed, made up to 30 mL with medium (RPMI 1640) and subsequently centrifuged. The sedimented cells were taken up in RPMI 1640 medium containing 10% FCS and plated in hypoxanthine-azaserine selection medium (100 mmol/l hypoxanthine, 1 µg/mL azaserine in RPMI 1640+10% FCS). Interleukin 6 from mouse (Roche Diagnostics GmbH, Catalog No. 1 444 581, 50 U/ml) was added to the medium as a growth factor.

After approximately 11 days the primary cultures were tested for specific antibody synthesis. Primary cultures which exhibited a positive reaction with indinavir and no cross-reaction with saquinavir, nelfinavir, ritonavir and amprenavir, were cloned in 96-well cell culture plates by means of a cell sorter.

The deposited cell lines/clones listed in Table 6 were obtained in this manner. Murine hybridomas <INDIN>M 1.003.12 and <INDIN>M 1.158.8 were deposited with the Deutsche Sammlung von Mikroorganismen und Zellkulturen GmbH (DSMZ) on Jun. 18, 2002 and assigned DSM No. ACC2547 and DSM No. ACC2546, respectively.

TABLE 6

| | Immunoglobulin subclass |
|---|---|
| Clone | IgG subclass |
| 1.158.8 | IgG1 kappa |
| 1.003.12 | IgG2a kappa |

For determination of the specificity of the antibodies in the culture supernatant of the hybridoma cells, microtiter plates coated with recombinant streptavidin (MicroCoat Co. Penzberg, Catalog No. 148051001) were coated with 500 ng/mL of indinavir biotin conjugate 4I (100 µL per well diluted in PBS/1.0% CROTEIN C/0.1% TWEEN 20; incubation overnight at 4° C.) and subsequently washed 3 times with 0.9% NaCl/0.1% TWEEN 20. (CROTEIN C is a trademark of Croda Colloids, Ltd. for hydrolyzed collagen protein.)

Free streptavidin binding sites were then blocked by incubation with 100 µg/mL of biotin (1 hour; ambient temperature while shaking) and subsequently washed 3 times with 0.9% NaCl/0.1% TWEEN 20.

Next, 50 µL of the analyte to be tested for cross-reaction was added to a coated well in a concentration series of 0-25 µg/mL (diluted in PBS plus 1.0% CROTEIN C, 0.1% TWEEN 20) and together with 50 µL of the antibody solution (culture supernatant) to be examined and incubated for 1 hour at room temperature while shaking. After washing 3 times with 0.9% sodium chloride/0.1% TWEEN 20, 100 µL of a horseradish peroxidase-labeled Fab fragment of a polyclonal antibody from the sheep against mouse Fc (pab<mouse Fc gamma>S-Fab-POD, Roche; 25 mU/ml) was added to each well to detect bound antibody from the sample, incubated for 1 hour at room temperature while shaking and subsequently washed 3 times with 0.9% sodium chloride/0.1% TWEEN 20.

Finally 100 µL/well ABTS solution (Roche Diagnostics GmbH, cat no. 1684302) was added and the absorbance at 405/492 nm was measured after 30 minutes at room temperature in a SLT Spectra Image microplate reader from TECAN.

Figure 17:
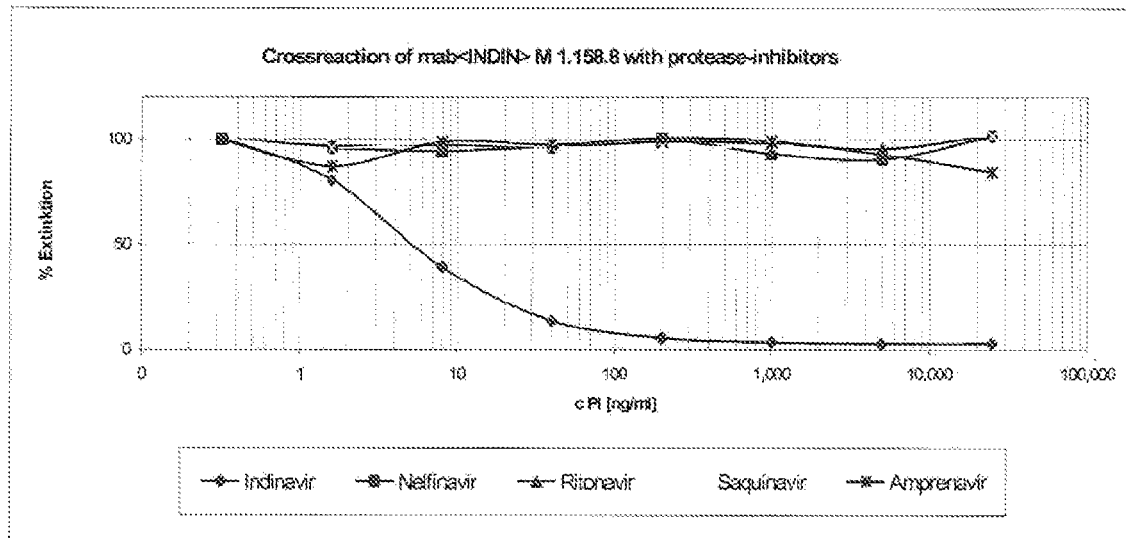
FIG. 17 are graphs showing the cross-reaction of monoclonal antibody <INDIN> M 1.158.8 and monoclonal antibody <INDIN> M 1.003.12 with indinavir, nelfinavir, ritonavir, saquinavir and amprenavir as described in Example 80.
Figure 17:
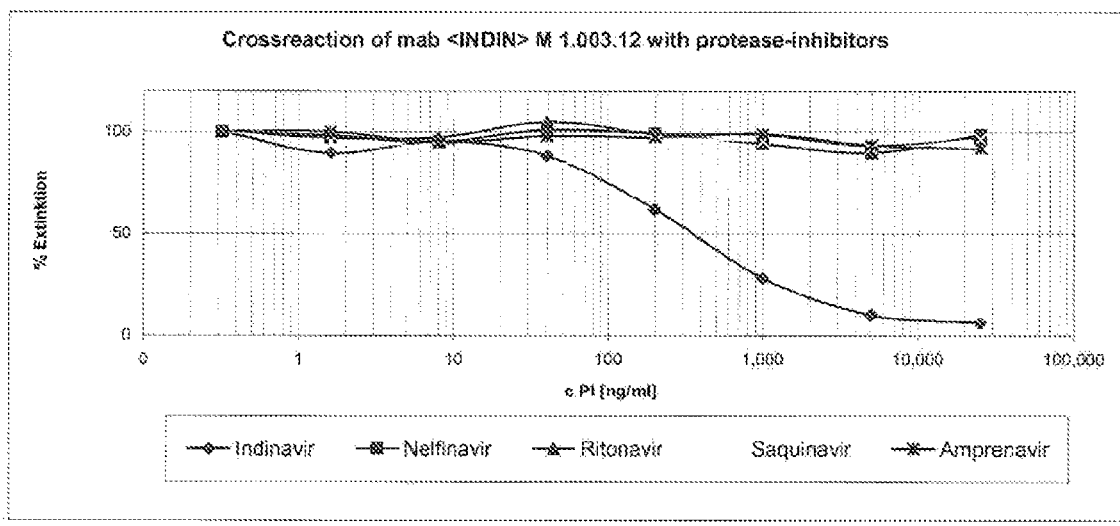
Figure 18:
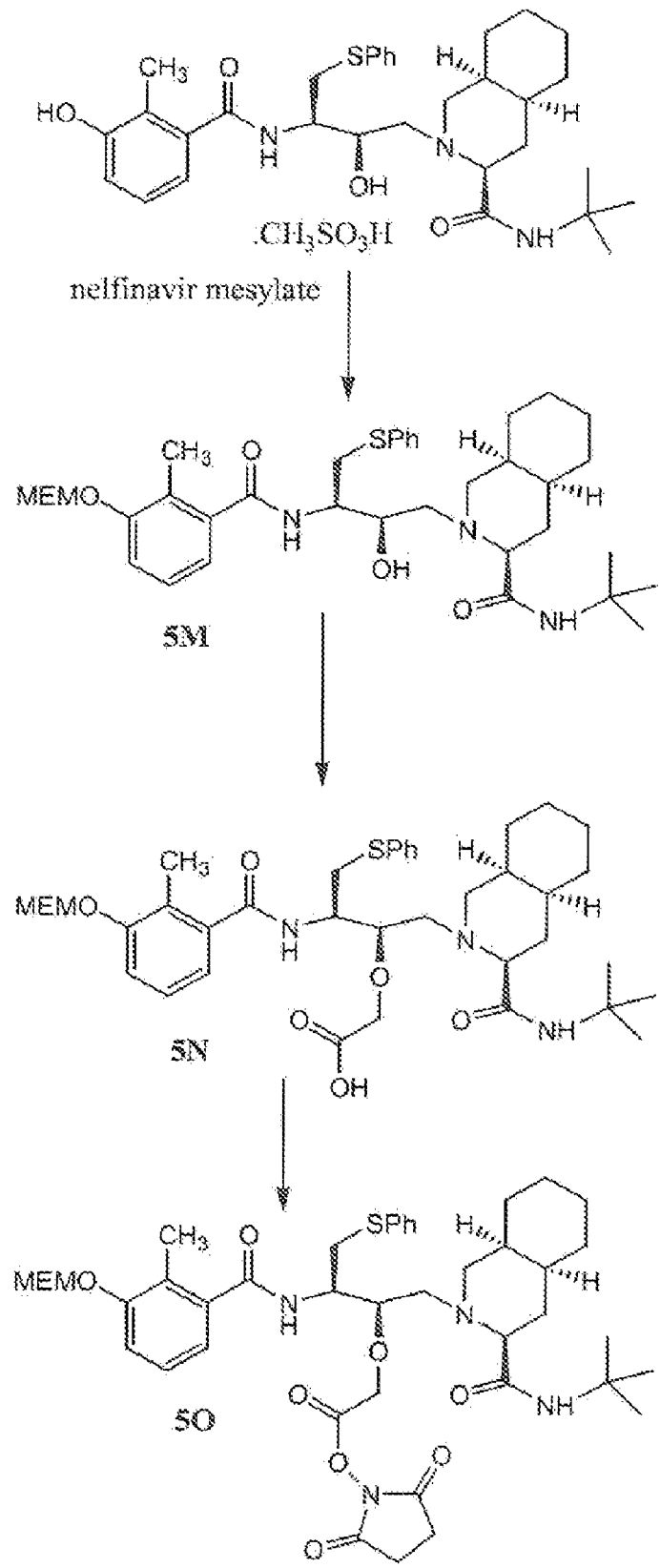
FIG. 18 illustrates a scheme for synthesis of $O^{35}$-MEM $O^c$-succinimido-oxycarbonylmethyl-nelfinavir ether.
Figure 19:
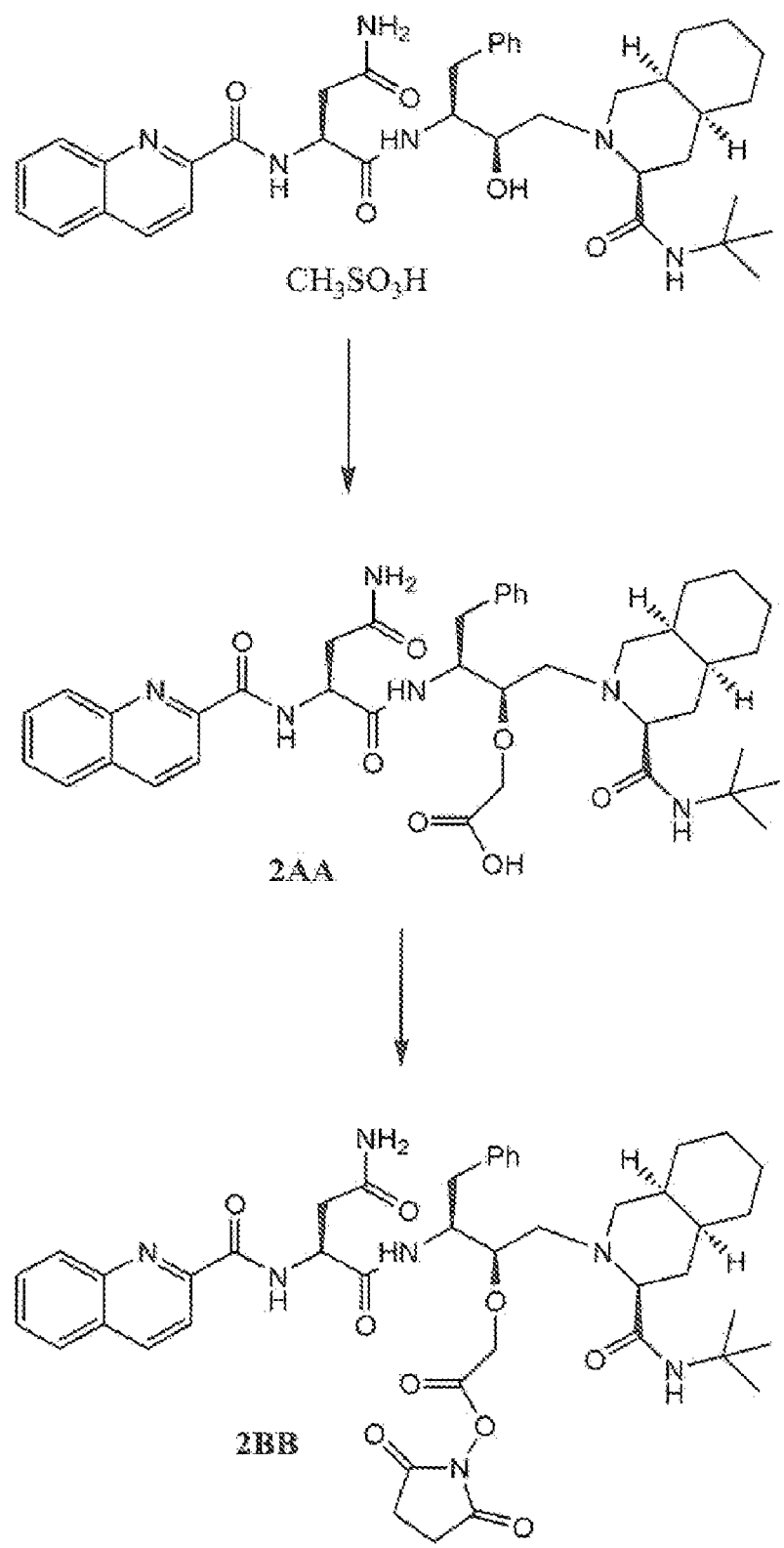
FIG. 19 illustrates a scheme for synthesis of $O^c$-succinimido-oxycarbonylmethyl-saquinavir ether.

Using the test system described above, it was shown that the monoclonal antibodies <INDIN> M 1.158.8 and <INDIN> M 1.003.12 exhibited less than 10% cross-reactivity with indinavir, nelfinavir, ritonavir, saquinavir, and amprenavir. FIG. 17 shows graphs of the cross-reaction of mab <INDIN> M 1.158.8 and mab <INDIN> M 1.003.12 with indinavir, nelfinavir, ritonavir, saquinavir and amprenavir.

EXAMPLE 81

Development of Monoclonal Antibodies to Amprenavir

Monoclonal antibodies to amprenavir were developed using the procedures for immunization, fusion, culture, and cloning as described above in Example 80. $O^c$-(succinimido-oxycarbonyl-butyryl-aminocaproyl)-amprenavir conjugate with KLH (3E) was used as the immunogen.

ELISA screening was accomplished using the amprenavir-biotin conjugate 3J. Murine hybridoma <AMPREN> M 1.1.52 was deposited with the DSMZ on Sep. 16, 2003 and assigned DSM No. ACC 2612.

Figure 20:
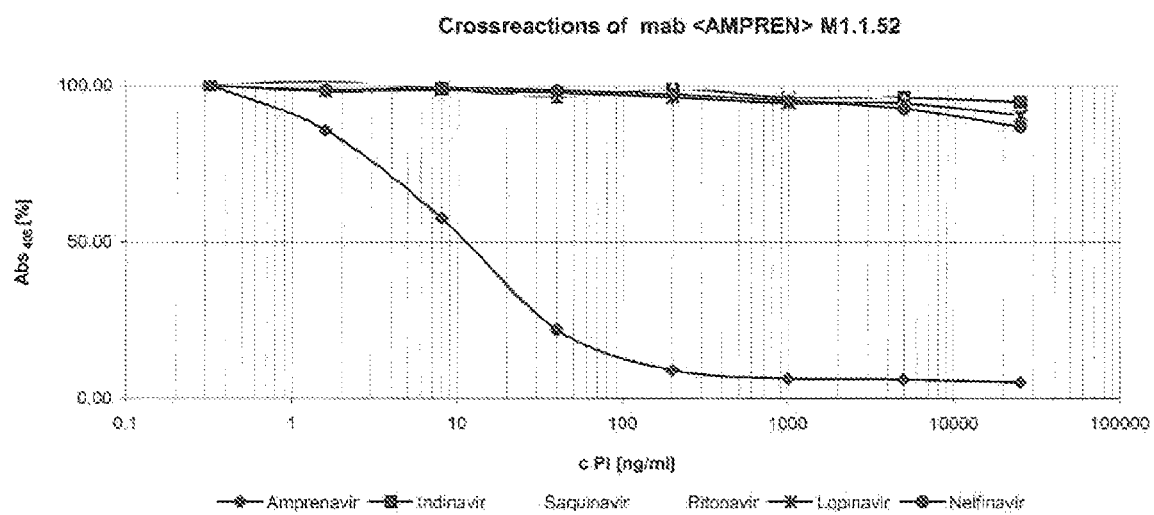
FIG. 20 is a graph showing the cross-reaction of monoclonal antibody <AMPREN> M 1.1.52 with indinavir, saquinavir, ritonavir, lopinavir, and nelfinavir as described in Example 81.

Specificity was determined as described above in Example 80. It was shown that the monoclonal antibody <AMPREN> M 1.1.52 exhibited less than 10% cross-reactivity with indinavir, nelfinavir, ritonavir, saquinavir, and lopinavir. FIG. 20 shows a graph of the cross-reaction of mab <AMPREN> M 1.1.52 with indinavir, nelfinavir, ritonavir, saquinavir and lopinavir.

EXAMPLE 82

Development of Monoclonal Antibodies to Lopinavir

Monoclonal antibodies to lopinavir were developed using the procedures for immunization, fusion, culture, and cloning as described above in Example 80. $O^c$-(succinimido-oxycarbonyl-butyryl-aminocaproyl)-lopinavir conjugate with KLH (6F) was used as the immunogen.

ELISA screening was accomplished using the lopinavir-biotin conjugate 6G. Murine hybridoma <LOPIN> M 1.1.85 was deposited with the DSMZ on Sep. 16, 2003 and assigned DSM No. ACC 2611.

Figure 21:
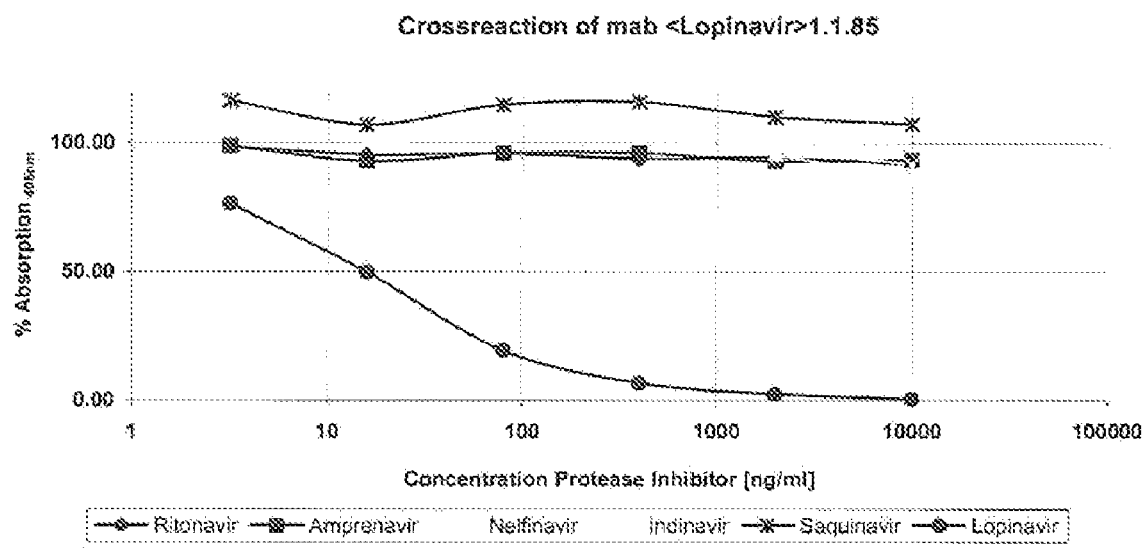
FIG. 21 is a graph showing the cross-reaction of monoclonal antibody <LOPIN> M 1.1.85 with indinavir, saquinavir, ritonavir, amprenavir, and nelfinavir as described in Example 82.

Specificity was determined as described above in Example 80. It was shown that the monoclonal antibody <LOPIN> M 1.1.85 exhibited less than 10% cross-reactivity with indinavir, nelfinavir, ritonavir, saquinavir, and amprenavir. FIG. 21 shows a graph of the cross-reaction of mab <LOPIN> M 1.1.85 with indinavir, nelfinavir, ritonavir, saquinavir and amprenavir.

EXAMPLE 83

Development of Monoclonal Antibodies to Ritonavir

Monoclonal antibodies to ritonavir were developed using the procedures for immunization, fusion, culture, and cloning as described above in Example 80. $O^c$-(succinimido-oxycarbonyl-butyryl-aminocaproyl)-ritonavir conjugate with LPH (1E) was used as the immunogen.

ELISA screening was accomplished using the ritonavir-biotin conjugate 1D. Murine hybridoma <RITON> M 1.5.44 was deposited with the DSMZ on Sep. 16, 2003 and assigned DSM No. ACC 2613.

Figure 22:
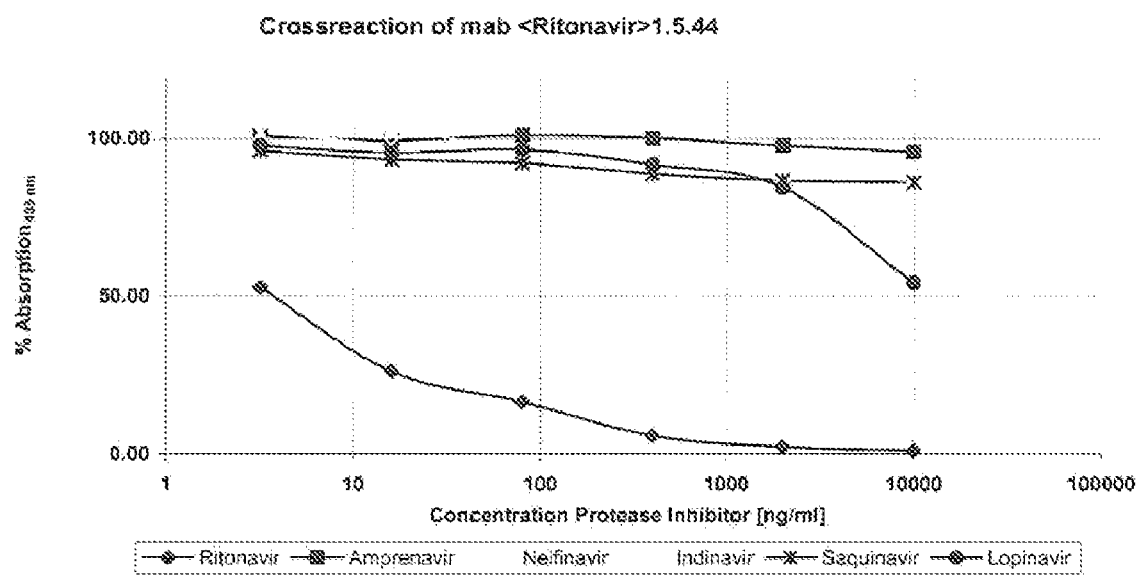
FIG. 22 is a graph showing the cross-reaction of monoclonal antibody <RITON> M 1.5.44 with indinavir, saquinavir, amprenavir, lopinavir, and nelfinavir as described in Example 83.
Figure 23:
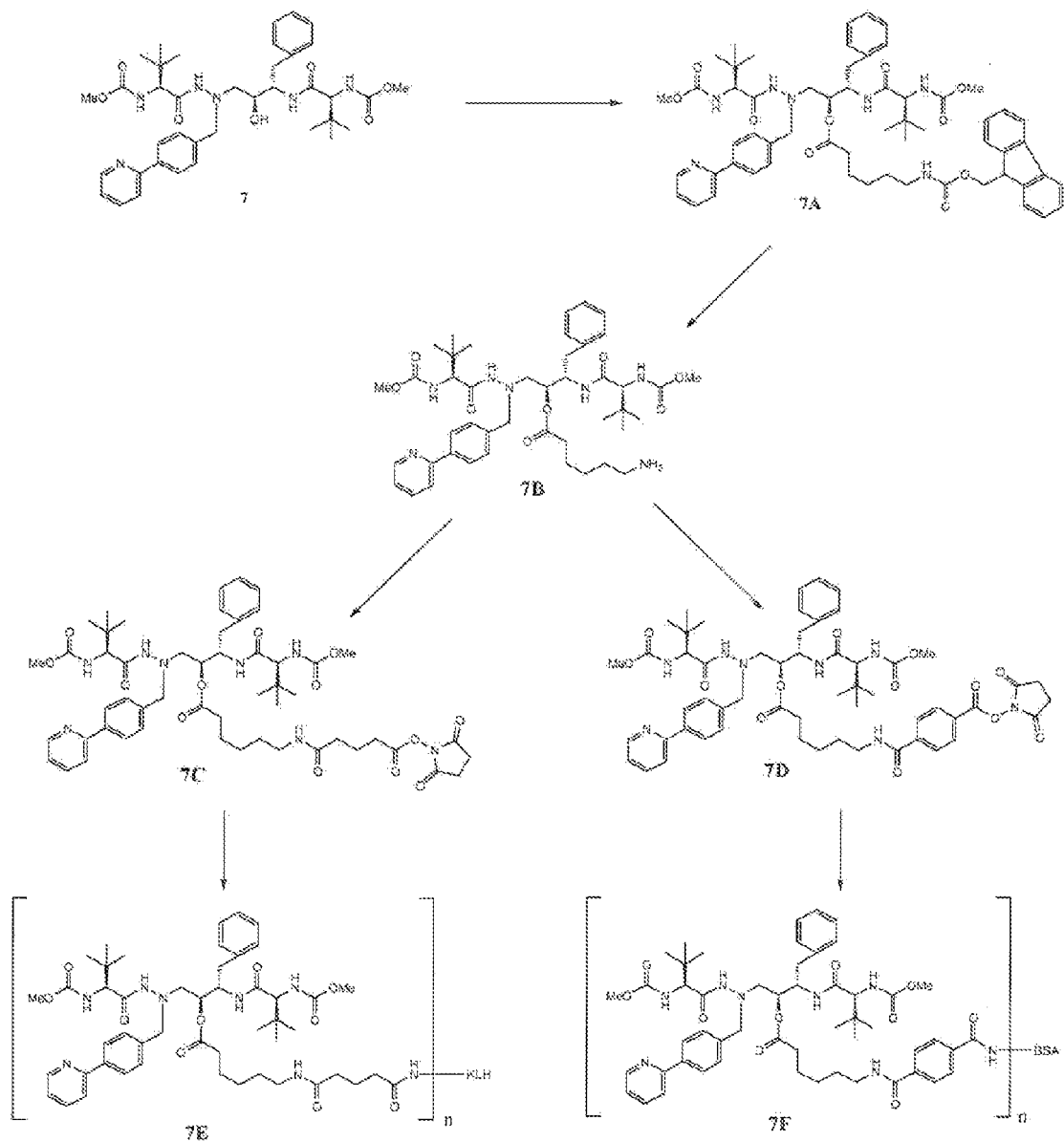
FIG. 23 illustrates a scheme for synthesis of O-acylated atazanavir activated haptens, KLH immunogen, and BSA conjugate.

Specificity was determined as described above in Example 80. It was shown that the monoclonal antibody <RITON> M 1.5.44 exhibited less than 10% cross-reactivity with indinavir, nelfinavir, lopinavir, saquinavir, and amprenavir. FIG. 22 shows a graph of the cross-reaction of mab <RITON> M 1.5.44 with indinavir, nelfinavir, lopinavir, saquinavir and amprenavir.

EXAMPLE 84

Synthesis of $O^c$—(N-FMOC-aminocaproyl)-atazanavir (7A)

$O^c$—(N-FMOC-aminocaproyl)-atazanavir (7A) was prepared by stirring atazanavir (7, 0.20 g) FMOC-aminocaproic acid (0.010 g, 1 eq), DCC (0.059 g, 1 eq); and DMAP (0.038 g, 1 eq) in dry methylene chloride (40 mL) in a similar manner to Example 1, except that after stirring overnight at room temperature, an additional 0.5 eq of FMOC-aminocaproic acid and 0.5 eq of DCC were added, and stirring continued for a further 3 days. Work-up and purification in a similar manner to that given in Example 1 gave the product 7A (210 mg; 71%) as a white solid. M+H 1040.5

EXAMPLE 85

Synthesis of $O^c$-(aminocaproyl)-atazanavir (7B)

$O^c$-(aminocaproyl)-atazanavir (7B) was prepared from $O^c$—(N-FMOC-aminocaproyl)-atazanavir (7A) of Example 84 (0.092 g) following the conditions described in Example 9, except that two silica gel chromatography purifications were performed (first column using 40% methanol in ethyl acetate (EtOAc), second column using 20% methanol in EtOAc) to give the product 7B as a solid (0.070 g, M+H 818.4

In another run, 7B was isolated as the trifluoracetic acid (TFA) salt after purification by preparative RP-HPLC (C18, gradient of 5% to 100% of 0.1% TFA-acetonitrile in 0.1% TFA-water).

EXAMPLE 86

Synthesis of $O^c$-(succinimido-oxycarbonyl-butyryl-aminocaproyl)-atazanavir (7C)

$O^c$-(aminocaproyl)-atazanavir (7B) as the TFA salt (0.070 g), triethylamine (22 µL), and succinimido-oxycarbonyl butyryl chloride (0.0195 g) were stirred for 3 hours in dry THF at about 0° C. (ice-water bath). The reaction was evaporated to dryness, redissolved in 15% THF in ethyl acetate, and purified by silica gel chromatography (elution with 30% THF in EtOAc, column pre-washed with several column volumes of 15% THF in EtOAc). Fractions containing product were combined, evaporated, redissolved in dry methylene chloride ($CH_2C_{12}$) and re-evaporated (repeated several times) to yield $O^c$-(succinimido-oxycarbonyl-butyryl-aminocaproyl)-atazanavir (7C) as a solid (24 mg, 31%). M+H 1029.4

EXAMPLE 87

Synthesis of $O^c$-[4'-(succinimido-oxycarbonyl)-benzoyl-aminocaproyl]-atazanavir (7D)

A solution of $O^c$-(aminocaproyl)-atazanavir (7B, 0.054 g) in 2 mL of dry DMF was added slowly to a stirring, cooled solution (ice-water bath) of disuccinimidyl terephthalic (0.0228 g) in 4.5 mL of dry DMF. After brief stirring, triethylamine (50 µL) was added and the reaction stirred overnight. Analysis by HPLC indicated essential completion of the reaction. Solvent was removed on a rotovap under high vacuum (at less than 25° C.), the residue redissolved in acetonitrile-water and purified by preparative RP-HPLC (C18, gradient of 5% to 100% of 0.1% TFA-acetonitrile in 0.1% TFA-water) to give, from the main peak after evaporation of acetonitrile, freezing and lyophilization, the product $O^c$-[4'-(succinimido-oxycarbonyl)-benzoyl-aminocaproyl]-atazanavir (7D), assigned as the trifluoracetic acid salt, in two cuts (0.036 g and 0.007 g, combined 0.043 g, 55%). M+H 1063.5 (free base)

EXAMPLE 88

Synthesis of $O^\varepsilon$-(succinimido-oxycarbonyl-butyryl-aminocaproyl)-atazanavir conjugate with KLH (7E)

$O^\varepsilon$-(succinimido-oxycarbonyl-butyryl-aminocaproyl)-atazanavir KLH conjugate was prepared from purified keyhole limpet hemocyanin (60 mg) and $O^\varepsilon$-(succinimido-oxycarbonyl-butyryl-aminocaproyl)-atazanavir (7C) from Example 86 (17 mg) following the general conditions described in Example 61, except that the reaction was performed in 40% DMSO. Protein quantification of the retentate by Coomassie Blue Protein Assay showed 10.8 mg/mL, 92% protein recovery (KLH standard/control). Amine quantification by TNBS colorimetric assay showed 56% lysine modification.

EXAMPLE 89

Synthesis of $O^\varepsilon$-[4'-(succinimido-oxycarbonyl)-benzoyl-aminocaproyl]-atazanavir conjugate with BSA (7F)

$O^\varepsilon$-[4'-(succinimido-oxycarbonyl)-benzoyl-aminocaproyl]-atazanavir BSA conjugate was prepared from bovine serum albumin (100 mg) and $O^\varepsilon$-[4'-(succinimido-oxycarbonyl)-benzoyl-aminocaproyl]-atazanavir (7D) as the TFA salt, from Example 87 (3 mg) following the general conditions described in Example 61, except that the reaction was performed in 40% DMSO. Protein quantification by Coomassie Blue protein assay showed quantitative recovery of protein at 10.0 mg/mL (BSA standard/control). UV difference spectroscopy showed the ratio of hapten to BSA to be 1:1.7.

What is claimed is:

1. The compound $O^\varepsilon$-(succinimido-oxycarbonyl-butyryl-aminocaproyl)-saquinavir.
2. The compound of $O^\varepsilon$-[4'-(succinimido-oxycarbonyl)-benzoyl-aminocaproyl]-saquinavir.
3. The compound of $O^\varepsilon$-[4'-(succinimido-oxycarbonyl)-phenyl-aminocaproyl]-saquinavir.
4. The compound of $O^\varepsilon$-(succinimido-oxycarbonyl-methylaminocarbonyl)-saquinavir.
5. The compound of $O^\varepsilon$-[4'-(succinimido-oxycarbonyl)-phenyl-methylamino-$^{\varepsilon\omega}$-glycyl-carbonyl]-saquinavir.
6. The compound $O^\varepsilon$-(succinimido-oxycarbonyl-butyryl-aminocaproyl)-saquinavir conjugate with KLH.
7. The compound $O^\varepsilon$-[4'-(succinimido-oxycarbonyl)-benzoyl-aminocaproyl]-saquinavir conjugate with BSA.
8. Murine hybridoma SAQ 10.2.1 having ATCC No. PTA-3973.
9. Murine hybridoma SAQ 14.1.1 having ATCC No. PTA-3974.

* * * * *